United States Patent
Watanabe et al.

(10) Patent No.: US 7,425,642 B2
(45) Date of Patent: Sep. 16, 2008

(54) HETEROARYL DERIVATIVE

(75) Inventors: Ken-ichi Watanabe, Osaka (JP); Katsunori Maruta, Osaka (JP); Kantaro Ushiroda, Osaka (JP); Ryu Nagata, Osaka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 128 days.

(21) Appl. No.: 10/563,361

(22) PCT Filed: Jul. 13, 2004

(86) PCT No.: PCT/JP2004/010282

§ 371 (c)(1), (2), (4) Date: Jan. 4, 2006

(87) PCT Pub. No.: WO2005/012245

PCT Pub. Date: Feb. 10, 2005

(65) Prior Publication Data

US 2006/0194857 A1 Aug. 31, 2006

(30) Foreign Application Priority Data

Jul. 15, 2003 (JP) .............................. 2003-274684

(51) Int. Cl.
C07D 207/00 (2006.01)
C07D 295/00 (2006.01)
(52) U.S. Cl. .................................... 548/539
(58) Field of Classification Search ............... 548/539
See application file for complete search history.

(56) References Cited

U.S. PATENT DOCUMENTS

| | | |
|---|---|---|
| 6,177,443 B1 | 1/2001 | Madsen et al. |
| 2002/0068746 A1 | 6/2002 | Blumenkopf et al. |
| 2003/0144338 A1 | 7/2003 | Matsumoto et al. |
| 2004/0162331 A1 | 8/2004 | Nagata et al. |

FOREIGN PATENT DOCUMENTS

| | | |
|---|---|---|
| JP | 2001-514631 A | 9/2001 |
| JP | 20015143631 T | 9/2001 |
| JP | 2002-121186 A | 4/2002 |
| JP | 2002121186 | 4/2002 |
| JP | 2003-171275 A | 6/2003 |
| WO | WO 02/00661 A1 | 1/2002 |
| WO | WO-02/00661 A1 | 1/2002 |
| WO | WO 02/085851 | 10/2002 |
| WO | WO 2004/048341 A1 | 6/2004 |

OTHER PUBLICATIONS

M. Guerre-Millo et al., "Peroxisome Proliferator activated Receptor β Activators Improve Insulin Sensitivity and Reduce Adiposity", J.Biol.Chem., vol. 275, No. 22, pp. 16638-16642.
T. M. Willson et al., "The PPARs: From Orphan Receptors to Drug Discovery", J. Medical Chemistry, vol. 43, No. 4, 2000, pp. 527-550.
Guerro-Millo, "Peroxisome Proliferator-activated Receptor β Activators Improve Insulin Sensitivity and Reduce Adiposity", vol. 275, No. 22, Issue of Jun. 2, pp. 16638-16642.
Willson et al., "The PPARs: From Orphan Receptors to Drug Discovery", vol. 43, No. 4, Feb. 24, 2000, pp. 527-542.

*Primary Examiner*—D. Margaret Seaman
*Assistant Examiner*—Niloofar Rahmani
(74) *Attorney, Agent, or Firm*—Birch Stewart Kolasch & Birch LLP

(57) ABSTRACT

A heteroaryl derivative of the formula (1):

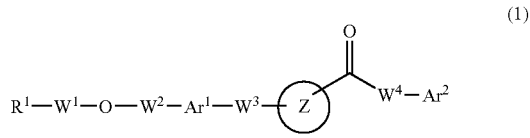

(wherein Ring Z is an optionally substituted heteroaryl, $R^1$ is a carboxyl group or an alkoxycarbonyl group, etc., $W^1$ and $W^2$ are an optionally substituted lower alkylene, $Ar^1$ is an optionally substituted arylene or an optionally substituted heteroarylene, $W^3$ is a single bond, a lower alkylene, a lower alkenylene, etc., $W^4$ is a single bond, $-NR^{10}-$, etc., $Ar^2$ is an optionally substituted aryl or an optionally substituted heteroaryl), or a prodrug thereof, or a pharmaceutically acceptable salt thereof.

9 Claims, No Drawings

HETEROARYL DERIVATIVE

TECHNICAL FIELD

The present invention relates to a novel heteroaryl compound having anti-diabetic activity or a salt thereof. More particularly, the present invention relates to a novel heteroaryl compound having an anti-diabetic activity, which improves insulin resistance and control the blood glucose level more safely. Further particularly, the present invention relates to a novel heteroaryl compound that simulates activity of peroxisome proliferator-activated receptor (PPAR) α, a PPARγ, or PPARα/γ, or that regluates activity of activation of PPARα/γ.

BACKGROUND ART

The number of patients with diabetes mellitus has been increasing steadily owing to the recent change in the lifestyle. According to the research done in 1997 in Japan, it has been speculated that the number of people diagnosed as possibly having diabetic mellitus is 6.9 million, and the number of people who cannot be ruled out the possibility of diabetes mellitus is 6.8 million. Most of the patients with diabetes mellitus in Japan are classified into type 2 diabetes mellitus, wherein the basal pathological conditions thereof are the reduced output of insulin and the insulin resistance, and medicaments against to each condition have been developed.

Sulfonylurea (SU) agents, which have long been known, and widely used for improving the reduced output of insulin, however, have been known to have a risk of hypoglycemia as a serious side effect, and further to maybe cause obesity to patients.

On the other hand, thiazolidinedione agents have been known as an insulin resistance improving agent.

Troglitazone was put on market first as a thiazolidinedione agent, but it induced a serious hepatic damage, by which the selling thereof was discontinued. In Japan, pioglitazone has been used clinically at the present, but the heart failure due to the increase in circulating plasma volume was reported as a serious side effect thereof, and hence, Urgent Safety Information on pioglitazone was issued on October, 2000, which announced that pioglitazone needs careful attention to heart failure and edema. As to rosiglitazone, which has been widely used in the western countries, there are reported side effects such as infection of upper respiratory tract, anemia, edema, weight gain, etc., and a thiazolidinedione agent having no concern regarding hepatitis damage or side effects on the cardiovascular system has not been put on the market yet.

Thiazolidinedione agents have been thought to exhibit anti-diabetic activity by activating PPARγ. It is known that PPAR has subtypes such as α, γ, δ (β), etc., and fibrate agents (e.g., clofibrate, fenofibrate, etc.), which have been used as antidyslipidemic agent, have been considered to exhibit their pharmacological activities by activating PPARα. It has recently been reported that the insulin resistance is improved by administering a PPARα activator to animal models (cf., Journal of Biological Chemistry, vol. 275, p 16638, 2000), and there is a growing possibility where PPARα activators may show an effectiveness against not only hyperlipidemia but also diabetes mellitus.

Many of compounds activating PPARγ or both PPARα and PPARγ such as isoxazolidediones are reported other than thiazolidinedione agents (cf., Journal of Medicinal Chemistry, 43, p. 527, 2000), but the efficacy and safety thereof in the clinical field are not confirmed yet. At the present, PPARα agonists, PPARγ agonists, PPARα/γ agonists or PPARα/γ activation regulators having a good antidiabetic activity and high safety have been desired.

In addition, diabetic medicines having a pyrrole group have been known (cf., JP-A-2002-121186, WO 02/085851, WO 2004/048341), but the efficacy and safety thereof in the clinical field are not reported yet.

DISCLOSURE OF INVENTION

An object of the present invention is to provide an agent for preventing or treating diabetes mellitus, which shows PPARα activating activity, PPARγ activating activity, or PPARα/γ activating activity, and improves insulin resistance and further shows a high safety.

The present inventors have intensively studied, and have found that a novel heteroaryl derivative improves hyperglycemia by activating PPARα, PPARγ, or PPARα/γ by improving insulin resistance and hyperlipidemia condition, and further shows a good safety, and are useful in the prophylaxis or treatment of diabetes mellitus, and finally they have accomplished the present invention.

Namely, the present invention provides the following.

[1] A heteroaryl derivative of the formula (1):

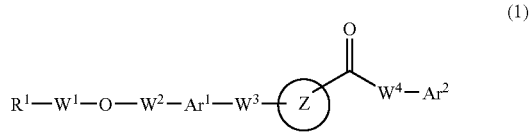

(wherein Ring Z is an optionally substituted heteroaryl;

$R^1$ is a carboxyl group, an alkoxycarbonyl group, an optionally substituted carbamoyl group, an optionally substituted cyclic aminocarbonyl group, an optionally substituted alkylsulfonylcarbamoyl group, an optionally substituted arylsulfonylcarbamoyl group, or a tetrazolyl group;

$W^1$ and $W^2$ are an optionally substituted lower alkylene;

$Ar^1$ is an optionally substituted arylene or an optionally substituted heteroarylene;

$W^3$ is a single bond, a lower alkylene, a lower alkenylene, or —$Y^1$—$W^5$— (in which $Y^1$ is an oxygen atom, a sulfur atom, —S(O)— or —S(O)$_2$—, and $W^5$ is a lower alkylene or a lower alkenylene);

$W^4$ is a single bond, —$NR^{10}$—, —$NR^{10}$—$W^6$— (in which $R^{10}$ is a hydrogen atom, or an optionally substituted lower alkyl, and $W^6$ is a lower alkylene), a lower alkylene, or a lower alkenylene;

$Ar^2$ is an optionally substituted aryl or an optionally substituted heteroaryl), or a prodrug thereof, or a pharmaceutically acceptable salt thereof.

[2] The heteroaryl derivative according to the above [1], wherein $W^3$ is a lower alkylene, a lower alkenylene, or —$Y^1$—$W^5$— (in which $Y^1$ is an oxygen atom, a sulfur atom, —S(O)— or —S(O)$_2$—, and $W^5$ is a lower alkylene or a lower alkenylene), or a prodrug thereof, or a pharmaceutically acceptable salt thereof.

[3] The heteroaryl derivative according to the above [1], wherein Ring Z is an optionally substituted pyrrole ring, an optionally substituted pyrazole ring, an optionally substituted imidazole ring, an optionally substituted triazole ring, an optionally substituted indole ring, an optionally substituted indazole ring, or an optionally substituted benzimidazole ring, $W^3$ is a $C_1$-$C_5$ alkylene, a $C_2$-$C_5$ alkenylene, or —Y$^{1'}$—W$^{5'}$— (in which Y$^{1'}$ is an oxygen atom or a sulfur atom, and W$^{5'}$ is a C$_1$-C$_5$ alkylene, or a C$_2$-C$_5$ alkenylene), W$^4$ is a single bond, —NR$^{10}$—, a C$_1$-C$_4$ alkylene, or a C$_2$-C$_4$ alkenylene, or a prodrug thereof, or a pharmaceutically acceptable salt thereof.

[4] The heteroaryl compound according to the above [1], wherein Ring Z is selected from the following formulae (2):

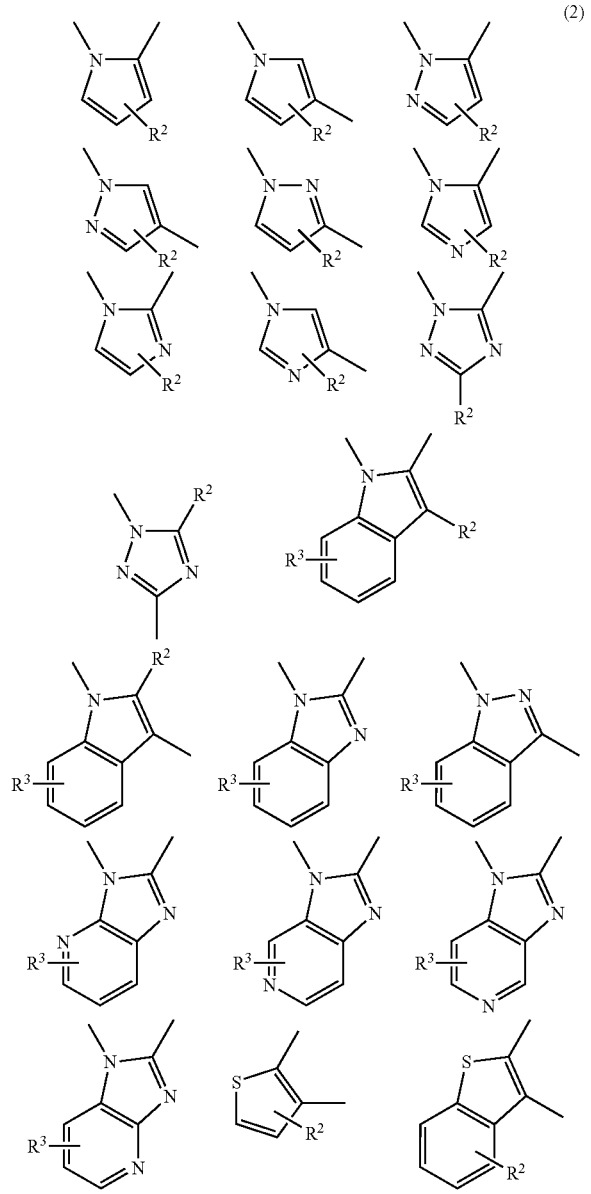

(2)

(in which the number of R$^2$ may be one or more, and each is independently selected from a hydrogen atom, a halogen atom, an optionally substituted alkyl, an optionally substituted aryl, an optionally substituted heteroaryl, and an optionally substituted thiol, the number of R$^3$ may be one or more, and each is independently selected from a hydrogen atom, a halogen atom, an optionally substituted alkyl, an optionally substituted aryl, an optionally substituted heteroaryl, an optionally substituted thiol, an optionally substituted hydroxy, an optionally substituted non-aromatic heterocyclic group, an optionally substituted amino, an optionally substituted acyl, and an alkylsulfonyl, and either of the binding direction of these groups may be applicable), or a prodrug thereof, or a pharmaceutically acceptable salt thereof.

[5] The heteroaryl compound according to the above [1] or [2], wherein Ring Z is an optionally substituted pyrrole ring, an optionally substituted imidazole ring, or an optionally substituted benzimidazole ring, or a prodrug thereof, or a pharmaceutically acceptable salt thereof.

[6] The heteroaryl compound according to any one of the above [1] to [3], wherein W$^1$ and W$^2$ are an optionally substituted straight chain C$_1$-C$_3$ alkylene group, or an optionally substituted C$_3$-C$_6$ alkylene group containing a cyclic structure, or a prodrug thereof, or a pharmaceutically acceptable salt thereof.

[7] The heteroaryl compound according to any one of the above [1] to [3], wherein W$^1$ and W$^2$ are an optionally substituted methylene or ethylene, W$^3$ is a straight chain C$_2$-C$_4$ alkylene, C$_3$-C$_4$ alkenylene, or —Y$^{1''}$—W$^{5''}$— (in which Y$^{1''}$ is an oxygen atom and W$^{5''}$ is a straight chain C$_2$-C$_4$ alkylene), W$^4$ is a single bond, —NR$^{10}$—, methylene, or transvinylene, or a prodrug thereof, or a pharmaceutically acceptable salt thereof.

[8] The heteroaryl compound according to any one of the above [1] to [6], wherein Ar$^1$ is an optionally substituted phenylene, and the binding position of W$^2$ is at meta-position or para-position with respect to the binding position of W$^3$, or a prodrug thereof, or a pharmaceutically acceptable salt thereof.

[9] The heteroaryl derivative according to the above [1], wherein Ring Z is a group of the formula (3):

(3)

(in which the number of R$^{2'}$ may be one or more, and each is independently selected from a hydrogen atom, methyl, an optionally substituted phenyl, and an optionally substituted heteroaryl), R$^1$ is a carboxyl group, an optionally substituted alkylsulfonylcarbamoyl group, or a tetrazolyl group, W$^1$ and W$^2$ are an optionally substituted methylene or ethylene, Ar$^1$ is an optionally substituted phenylene, W$^3$ is a straight chain C$_2$-C$_4$ alkylene or C$_3$-C$_4$ alkenylene, Ar$^2$ is an optionally substituted phenyl, or a prodrug thereof, or a pharmaceutically acceptable salt thereof.

[10] The heteroaryl derivative according to the above [1], wherein Ring Z is a group of the formula (4):

(4)

(in which the number of R$^{2'}$ may be one or more, and each is independently selected from a hydrogen atom, methyl, an optionally substituted phenyl, and an optionally substituted heteroaryl), R$^1$ is a carboxyl group, an optionally substituted alkylsulfonylcarbamoyl group, or a tetrazolyl group, W$^1$ and $W^2$ are an optionally substituted methylene or ethylene, $Ar^1$ is an optionally substituted phenylene, $W^3$ is a straight chain $C_2$-$C_4$ alkylene or $C_3$-$C_4$ alkenylene, $Ar^2$ is an optionally substituted phenyl, or a prodrug thereof, or a pharmaceutically acceptable salt thereof.

[11] The heteroaryl derivative according to the above [1], wherein Ring Z is selected from the following formulae (5):

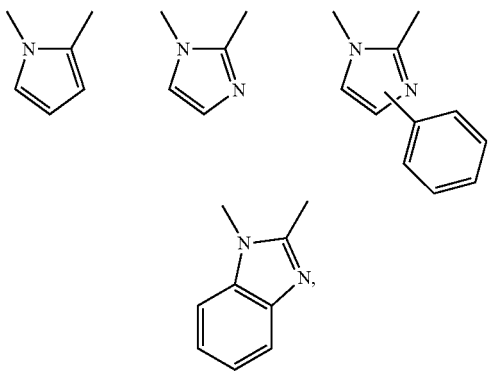

(5)

$R^1$ is a carboxyl group, $W^1$ is an optionally substituted methylene or ethylene, $W^2$ is methylene, $Ar^1$ is phenylene, $W^3$ is propenylene or propylene, $Ar^2$ is an optionally substituted phenyl, or a prodrug thereof, or a pharmaceutically acceptable salt thereof.

[12] The heteroaryl derivative according to the above [1], wherein Ring Z is selected from the following formulae (6):

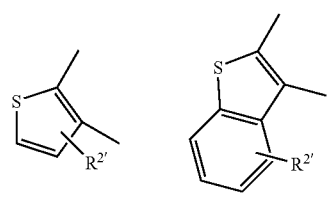

(6)

(in which the number of $R^{2'}$ may be one or more, and each is independently selected from a hydrogen atom, methyl, an optionally substituted phenyl, and an optionally substituted heteroaryl), $R^1$ is a carboxyl group, $W^1$ is an optionally substituted methylene or ethylene, $W^2$ is methylene, $Ar^1$ is phenylene, $W^3$ is propenylene or propylene, $Ar^2$ is an optionally substituted phenyl, or a prodrug thereof, or a pharmaceutically acceptable salt thereof.

[13] The heteroaryl derivative according to the above [1], wherein Ring Z is a group of the formula (7):

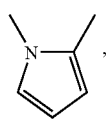

(7)

$R^1$ is a carboxyl group, $W^1$ is an optionally substituted methylene, $W^2$ is methylene, $Ar^1$ is phenylene, $W^3$ is propenylene or propylene, $Ar^2$ is an optionally substituted phenyl, or a prodrug thereof, or a pharmaceutically acceptable salt thereof.

[14] The heteroaryl derivative according to the above [1], wherein Ring Z is a group of the formula (7):

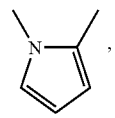

(7)

$R^1$ is a carboxyl group, $W^1$ is a methylene optionally substituted by an alkyl having 1 to 3 carbon atoms, $W^2$ is methylene, $Ar^1$ is phenylene, $W^3$ is propenylene or propylene, $Ar^2$ is a phenyl optionally substituted by an alkyl having 1 to 3 carbon atoms or an alkoxy having 1 to 3 carbon atoms, or a prodrug thereof, or a pharmaceutically acceptable salt thereof.

[15] The heteroaryl derivative according to the above [1], wherein Ring Z is selected from the following formulae (8):

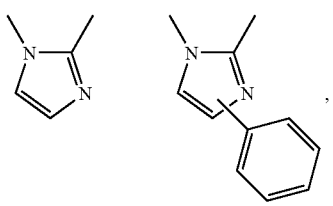

(8)

$R^1$ is a carboxyl group, $W^1$ is a methylene optionally substituted by an alkyl group having 1 to 3 carbon atoms, $W^2$ is methylene, $Ar^1$ is phenylene, $W^3$ is propenylene or propylene, $Ar^2$ is a phenyl optionally substituted by an alkyl having 1 to 3 carbon atoms or an alkoxy having 1 to 3 carbon atoms, or a prodrug thereof, or a pharmaceutically acceptable salt thereof.

[16] The heteroaryl derivative according to the above [1], wherein Ring Z is a group of the formula (9):

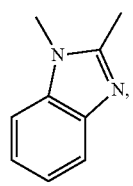

(9)

$R^1$ is a carboxyl group, $W^1$ is a methylene optionally substituted by an alkyl group having 1 to 3 carbon atoms, $W^2$ is methylene, $Ar^1$ is phenylene, $W^3$ is propenylene, $Ar^2$ is a phenyl optionally substituted by an alkyl group having 1 to 3 carbon atoms or an alkoxy group having 1 to 3 carbon atoms, or a prodrug thereof, or a pharmaceutically acceptable salt thereof.

[17] The heteroaryl derivative according to the above [1], which is a compound selected from the following formulae (10):

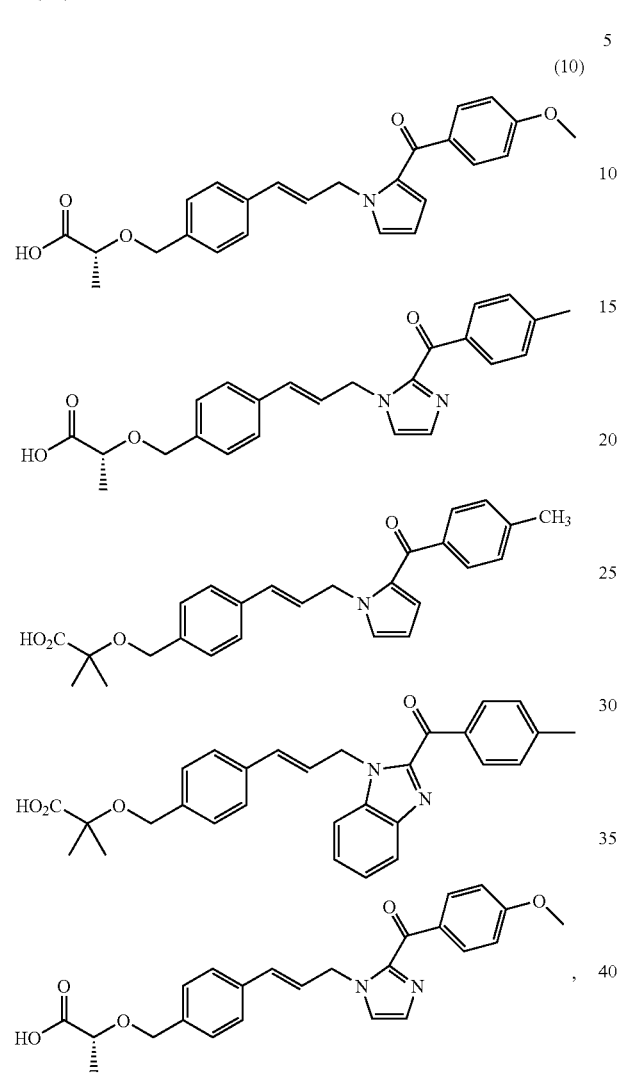

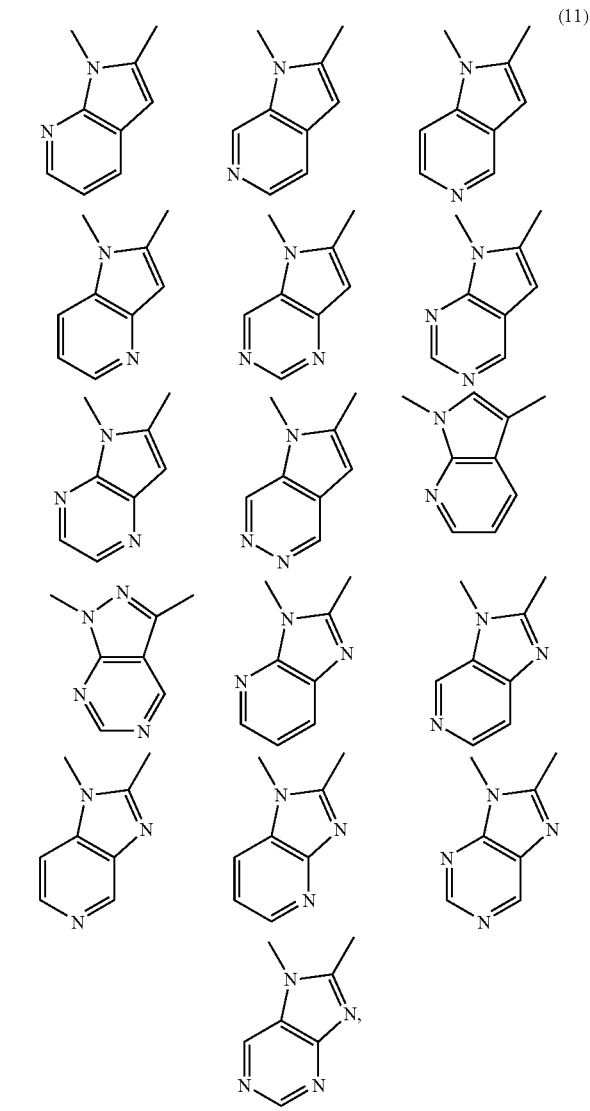

or a prodrug thereof, or a pharmaceutically acceptable salt thereof.

By the present invention, it may become possible to provide a novel heteroaryl derivative or a salt thereof, which improves and controls more safety insulin resistance, and is useful as an agent for prophylaxis or treatment of diabetic mellitus.

BEST MODE FOR CARRYING OUT THE INVENTION

The present invention relates to the following novel heteroaryl derivative and a salt thereof, etc.

With respect to the heteroaryl derivative of the formula (1) of the present invention, the definitions in said formula are explained in more detail below.

The heteroaryl for Ring Z includes, for example, a pyrrole ring, a pyrazole ring, an imidazole ring, a triazole ring, an indole ring, an indazole ring, a benzimidazole ring, and a group of the following formulae (11):

and these groups may have 1 to 3 substituents at any possible position.

The pyrrole ring includes, for example, a pyrrole-1,2-diyl, a pyrrole-1,3-diyl, a pyrrole-3,4-diyl, etc., the pyrazole ring includes, for example, a pyrazole-1,5-diyl, a pyrazole-1,4-diyl, a pyrazole-1,3-diyl, etc., the imidazole ring includes, for example, an imidazole-1,2-diyl, an imidazole-1,5-diyl, an imidazole-1,4-diyl, an imidazole-4,5-diyl, etc., the triazole ring includes, for example, 1,2,4-triazole-1,5-diyl, a 1,2,4-triazole-1,3-diyl, a 1,3,4-triazole-1,2-diyl, etc., the indole ring includes, for example, an indole-1,2-diyl, an indole-1,3-diyl, an indole-1,6-diyl, etc., the indazole ring includes, for example, an indazole-1,3-diyl, etc., and the benzimidazole ring includes, for example, a benzimidazole-1,2-diyl, etc. Preferable ones are a pyrrole-1,2-diyl, a pyrrole-1,3-diyl, imidazole-1,2-diyl, imidazole-1,5-diyl, 1,2,4-triazole-1,5-diyl, indole-1,2-diyl, indole-1,3-diyl, benzimidazole-1,2-diyl.

The aryl of the "optionally substituted aryl" for $Ar^2$ includes, for example, a phenyl, a 1-naphthyl, a 2-naphthyl, etc. Preferable one is a phenyl.

The heteroaryl of the "optionally substituted heteroaryl" for $Ar^2$ includes, for example, a heteromonocyclic aryl or heterobicyclic aryl having 1 to 3 heteroatoms selected from a nitrogen atom, an oxygen atom and a sulfur atom, such as a 5-membered monocyclic heteroaryl (e.g., thiophen, furan, imidazole, pyrazole, thiazole, oxazole, isothiazole, isoxazole, etc.), a 6-membered monocyclic heteroaryl (e.g., pyridine, pyrimidine, pyrazine, pyridazine, triazine, etc.), a bicyclic heteroaryl (e.g., indole, isoindole, indolidine, indazole, purine, 4-H-quinolidine, quinoline, isoquinoline, phtharazine, naphthyridine, quinoxaline, quinazoline, benzimidazole, benzothiazole, benzoxazole, benzofuran, benzothiophene, etc.), and the more preferable ones are thiophene, furan, pyrrole, pyridine, indole, benzothiazole, benzoxazole, benzofuran, benzothiophene, etc.

The arylene of the "optionally substituted arylene" for $Ar^1$ includes, for example, a $C_6$-$C_{10}$ arylene such as 1,3-phenylene 1,4-phenylene, naphthalene-1,3-diyl, naphthalene-1,4-diyl, etc., and the preferable one is 1,3-phenylene, and 1,4-phenylene.

The heteroarylene of the "optionally substituted heteroarylene" for $Ar^1$ includes, for example, a monocyclic or bicyclic heteroarylene group having optionally 1 to 3 heteroatoms selected from a nitrogen atom, an oxygen atom, and a sulfur atom, such as a 6-membered monocyclic heteroarylene (e.g., pyridine-diyl, pyrimidine-diyl, pyrazine-diyl, pyridazine-diyl, triazine-diyl, etc.), a 5-membered monocyclic heteroarylene (e.g., thiophene-diyl, furan-diyl, pyrrole-diyl, imidazole-diyl, pyrazole-diyl, thiazole-diyl, oxazole-diyl, isothiazole-diyl, isoxazole-diyl, etc.), a bicyclic heteroarylene (e.g., indole-diyl, isoindole-diyl, indolidine-diyl, indazole-diyl, purine-diyl, 4-H-quinolidine-diyl, quinoline-diyl, isoquinoline-diyl, phthalazine-diyl, naphthyridine-diyl, quinoxaline-diyl, quinazoline-diyl, benzimidazole-diyl, benzothiazole-diyl, benzoxazole-diyl, benzofuran-diyl, benzothiophene-diyl, etc.), and more preferable ones are pyridine-diyl, thiophene-diyl, pyrrole-diyl, furan-diyl, indole-diyl.

The "optionally substituted aryl", the "optionally substituted heteroaryl" for $Ar^2$, and the "optionally substituted arylene", the "optionally substituted heteroarylene" for $Ar^1$ may have 1 to 5 substituents, preferably 1 to 3 substituents, at any substitution available position. Said substituent includes, for example, an optionally substituted lower alkyl, a lower alkenyl, an aryl, a substituted aryl, a heteroaryl, a substituted heteroaryl, an optionally substituted non-aromatic heterocylic group, a halogen atom, an optionally substituted amino, an optionally substituted acyl, an optionally substituted hydroxy, an optionally substituted thiol, an alkylsulfonyl, cyano, nitro, a carbamoyl group optionally substituted by an alkyl.

The lower alkyl of the "optionally substituted lower alkyl" includes, for example, a straight chain or a branched chain $C_1$-$C_8$ alkyl, or a $C_1$-$C_8$ alkyl having a cyclic structure, such as methyl, ethyl, 1-propyl, 2-propyl, 1-butyl, 2-butyl, t-butyl. The alkyl having a cyclic structure includes, for example, cyclopropyl, cyclopropylmethyl, cyclobutyl, cyclobutylmethyl, cyclopentyl, cyclopentylmethyl, cyclohexyl, cyclohexylmethyl, cyclohexylethyl, etc. Preferable one is methyl, ethyl, 2-propyl, cyclopropyl.

The substituent of said "optionally substituted lower alkyl" includes, for example, hydroxy group, oxo, amino, a $C_1$-$C_8$ monoalkylamino (e.g., methyl-amino, ethylamino, propylamino, etc.), a $C_2$-$C_{12}$ dialkylamino (e.g., dimethyl-amino, ethylmethylamino, diethylamino, etc.), a $C_1$-$C_8$ alkoxy (e.g., methoxy, ethoxy, 1-propyloxy, 2-propyloxy, etc.), a halogen atom (e.g., fluorine, chlorine, bromine, etc.), a $C_1$-$C_8$ haloalkoxy (e.g., trifluoromethoxy, etc.), a non-aromatic heterocyclic group (e.g., morpholino, piperidino, pyrrolidino, 4-methyl-1-piperazino, etc.), an aryl (e.g., phenyl, 1-naphthyl, etc.), or a heteroaryl (e.g., pyridiyl, thienyl, furanyl, etc.), and preferable ones are methylamino, ethylamino, dimethylamino, diethylamino, methoxy, ethoxy, 2-propyloxy, fluorine, chlorine, trifluoromethoxy, morpholino, piperidino, pyrrolidino, phenyl, pyridiyl, etc.

The "lower alkenyl" includes a straight chain or a branched chain $C_2$-$C_8$ alkenyl or a $C_2$-$C_8$ alkenyl having a cyclic structure, for example, vinyl, 1-propenyl, 2-propenyl, 2-methyl-1-propenyl, etc., and preferable ones are vinyl, and 2-propenyl.

The aryl of the "aryl, substituted aryl" includes, for example, phenyl, 1-naphthyl, 2-naphthyl, etc., and preferable one is phenyl.

The heteroaryl of "heteroaryl, substituted heteroaryl" is the same as those for the heteroaryl for $Ar^2$, and preferable ones are thiophene, furan, pyrrole, pyridine, etc.

The non-aromatic heterocyclic group of the "optionally substituted non-aromatic heterocyclic group" includes one having 2 to 6 carbon atoms, and as a ring-forming ring, 1 to 3 heteroatoms selected from an oxygen atom, a sulfur atom and a nitrogen atom in addition to the carbon atoms, for example, morpholino, thiomorpholino, piperidino, pyrrolidino, 4-methyl-1-piperazino, etc. The preferable ones are morpholino, piperidino, pyrrolidino, etc.

The substituents of said "substituted aryl, substituted heteroaryl, optionally substituted non-aromatic heterocyclic group" includes, for example, a $C_1$-$C_8$ alkyl (e.g., methyl, ethyl, 1-propyl, 2-propyl, 1-butyl, 2-butyl, t-butyl, etc.), a $C_1$-$C_8$ alkoxy (e.g., methoxy, ethoxy, 1-propyloxy, 2-propyloxy, etc. ), a halogen atom (e.g., fluorine, chlorine, bromine, etc.), a $C_1$-$C_8$ haloalkoxy (e.g., trifluoro-methoxy, etc.), a $C_1$-$C_8$ haloalkyl (e.g., trifluoromethyl, etc.), and the preferable ones are methyl, ethyl, 2-propyl, methoxy, ethoxy, fluorine, chlorine, trifluoro-methoxy, trifluoromethyl.

The halogen atom is fluorine, chlorine, bromine, iodine, and preferable one is fluorine, chlorine.

The "optionally substituted amino" includes, for example, amino, and an amino optionally substituted by one or two groups selected from a $C_1$-$C_8$ alkyl (e.g., methyl, ethyl, propyl, etc.), a $C_1$-$C_8$ acyl (e.g., acetyl, propionyl, etc.), an aryl (e.g., phenyl, etc.), and a heteroaryl, and preferable ones are methylamino, dimethylamino, ethylamino, diethylamino, cyclohexylamino, acetylamino, benzoylamino, phenylamino, etc.

The acyl of the "optionally substituted acyl" includes, in addition to formyl, a group combining a carbonyl group and a $C_1$-$C_8$ alkyl (e.g., methyl, ethyl, 1-propyl, 2-propyl, 1-butyl, 2-butyl, t-butyl, etc.), an aryl (e.g., phenyl, etc.), or a heteroaryl (e.g., thienyl, pyridyl, etc.), and preferable ones are acetyl, propionyl, cyclobutanecarbonyl, cyclohexanecarbonyl, benzoyl, etc.

Said acyl group may have 1 to 3 substituents at any substitution possible position, and in these cases, the substituent includes a $C_1$-$C_3$ straight chain or branched chain alkyl (preferably methyl, ethyl, 2-propyl, etc.), a $C_1$-$C_3$ straight chain or branched chain alkoxy (preferably methoxy, ethoxy, 2-propoxy, etc.), a halogen (preferably fluorine, chlorine), hydroxy, amino, etc.

The "optionally substituted hydroxy group" includes a hydroxy, an optionally substituted alkoxy, an optionally substituted aralkyloxy, an optionally substituted aryloxy, and an optionally substituted acyloxy, etc.

The alkoxy of the "optionally substituted alkoxy" includes a $C_1$-$C_8$ alkoxy (e.g., methoxy, ethoxy, 2-propoxy, cyclopentyloxy, etc.), and preferable ones are methoxy, ethoxy, 2-propyloxy. When an alkyl or an alkoxy exists adjacently, then said group may combine together with an adjacent group to form a ring having a substituent, for example, methylenedioxy, ethylenedioxy, 2-methyl-methylenedioxy, 2-methyl-ethylenedioxy, 1-oxy-2-ethylene, 1-oxy-2-propylene, etc., and preferable ones are methylenedioxy, ethylenedioxy.

The aralkyloxy of the "optionally substituted aralkyloxy" includes, for example, a phenyl-($C_1$-$C_4$alkyl)oxy, and preferable ones are benzyloxy, phenethyloxy.

The aryloxy of the "optionally substituted aryloxy" includes, for example, phenyloxy, 1-naphthyloxy, etc., and preferable one is phenyloxy.

The acyloxy of the "optionally substituted acyloxy" includes, for example, acetyloxy, propionyloxy, etc.

The substituent of the above-mentioned "optionally substituted alkoxy, optionally substituted aralkyloxy, optionally substituted aryloxy, or optionally substituted acyloxy" includes, for example, a halogen (preferably fluorine, chlorine), a $C_1$-$C_3$ straight chain or branched chain alkoxy (preferably methoxy, ethoxy, 2-propoxy), a $C_1$-$C_3$ straight chain or branched chain alkyl (preferably methyl, ethyl, 2-propyl, etc.), trifluoromethyl, trifluoromethoxy, etc.

The "optionally substituted thiol" includes thiol, an alkylthio, an aralkylthio, an arylthio, or a heteroarylthio, etc.

The alkylthio includes, for example, methylthio, ethylthio, 2-propylthio, or cyclopentylthio, etc., and preferable ones are methylthio, ethylthio.

The aralkylthio includes, for example, a phenyl-($C_1$-$C_8$ alkyl)thio, and preferable ones are benzylthio, phenethylthio.

The arylthio includes, for example, phenylthio, 1-naphthylthio, etc., and preferable one is phenylthio.

The heteroarylthio is preferably pyridylthio, imidazolylthio, etc.

The alkylsulfonyl includes a straight chain or branched chain $C_1$-$C_8$ alkylsulfonyl, and preferable ones are methanesulfonyl, ethanesulfonyl, 2-propylsulfonyl, etc.

The "carbamoyl group optionally substituted by an alkyl" includes, for example, carbamoyl, a straight chain or branched chain $C_1$-$C_6$ monoalkyl-aminocarbonyl, or a straight chain or branched chain $C_2$-$C_{12}$ dialkylaminocarbonyl. The straight chain or branched chain $C_1$-$C_6$ alkylaminocarbonyl is preferably methylaminocarbonyl, ethylaminocarbonyl, propylaminocarbonyl, 2-propylaminocarbonyl. The straight chain or branched chain $C_2$-$C_{12}$ dialkyl-aminocarbonyl includes, for example, a carbamoyl substituted by the same or different alkyl groups, and preferable one is dimethylaminocarbonyl, diethyl-aminocarbonyl, ethylmethylaminocarbonyl, methylpropylaminocarbonyl, dicyclohexylaminocarbonyl.

The lower alkylene for $W^4$ and $W^6$ includes, for example, a straight chain or branched chain $C_1$-$C_{10}$ alkylene and a $C_3$-$C_{10}$ alkylene having a cyclic structure, and preferable one is a straight chain or branched chain $C_1$-$C_4$ alkylene or a $C_3$-$C_4$ alkylene having a cyclic structure. The straight chain or branched chain $C_1$-$C_4$ alkylene includes, for example, methylene, ethylene, trimethylene, 1-methylmethylene, 1-ethylmethylene, 1-propylmethylene, 1-methylethylene, 2-methylethylene, 1-ethylethylene, etc., and preferable one is methylene and ethylene. The $C_3$-$C_4$ alkylene having a cyclic structure is an alkylene of the following formulae (12):

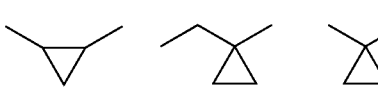

(12)

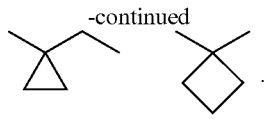

-continued

The lower alkenylene for $W^4$ includes, for example, a $C_2$-$C_8$ alkenylene, and preferable one is a $C_2$-$C_4$ alkenylene. The $C_2$-$C_4$ alkenylene includes, for example, a straight chain or branched chain $C_2$-$C_4$ alkenylene, such as cis- or trans-vinylene, cis- or trans-i-propenylene, cis- or trans-2-propenylene, cis- or trans-1-butenylene, cis- or trans-2-butenylene, trans-1-methyl-vinylene, trans-1-ethyl-vinylene, trans-1-methyl-1-propenylene, trans-2-methyl-1-propenylene, etc., and preferable one is cis- or trans-vinylene.

The lower alkylene for $W^3$ and $W^5$ includes, for example, a straight chain or branched chain $C_1$-$C_{10}$ alkylene, or a $C_3$-$C_{10}$ alkylene having a cyclic structure, and preferable one is a straight chain or branched chain $C_1$-$C_5$ alkylene or a $C_3$-$C_5$ alkylene having a cyclic structure. The straight chain or branched chain $C_1$-$C_5$ alkylene is, for example, methylene, ethylene, trimethylene, tetramethylene, 1-methyl-ethylene, 1,1-dimethyl-ethylene, 1-methyl-propylene, 1,1-dimethyl-propylene, etc., and the $C_3$-$C_5$ alkylene having a cyclic structure is an alkylene of the following formulae (13):

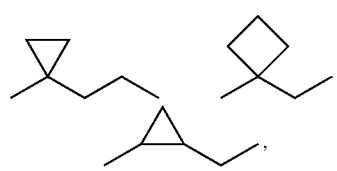

(13)

and preferable one is ethylene, trimethylene, tetramethylene.

The lower alkenylene for $W^3$ and $W^5$ includes, for example, a $C_2$-$C_8$ alkenylene, and preferable one is a $C_2$-$C_5$ alkenylene. The $C_2$-$C_5$ alkenylene includes, for example, a straight chain or branched chain $C_2$-$C_5$ alkenylene, such as cis- or trans-vinylene, cis- or trans-1-propenylene, cis- or trans-2-propenylene, cis- or trans-1-butenylene, cis- or trans-2-butenylene, cis- or trans-3-butenylene, cis- or trans-1-methyl-2-propenylene, cis- or trans-3-methyl-2-propenylene, cis- or trans-2-methyl-2-propenylene, cis- or trans-1-methyl-2-propenylene, etc., and more preferable one is trans-1-propenylene, trans-1-butenylene.

The lower alkylene of the "optionally substituted lower alkylene" for $W^1$ and $W^2$ includes, for example, a straight chain $C_1$-$C_{10}$ alkylene or a $C_3$-$C_{10}$ alkylene having a cyclic structure, and preferable one is a straight chain $C_1$-$C_4$ alkylene or a $C_3$-$C_8$ alkylene having a cyclic structure. The straight chain $C_1$-$C_4$ alkylene is methylene, ethylene, trimethylene, etc., and more preferable one is methylene, ethylene. The $C_3$-$C_8$ alkylene containing a cyclic structure includes an alkylene of the following formulae (14):

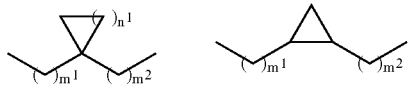

(14)

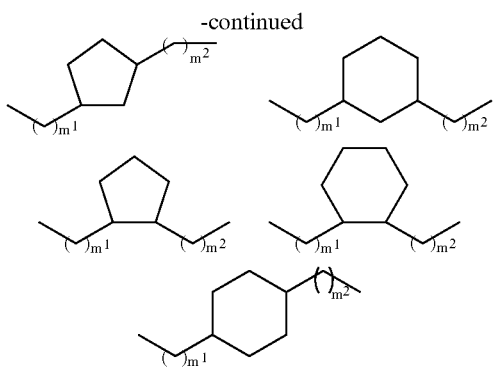

(wherein $m^1$, $m^2$ are integer of 0 to 2, and $n^1$ is an integer of 1 to 4), etc.

The substituent of the "optionally substituted lower alkylene" for $W^1$ and $W^2$ includes, for example, an optionally substituted alkyl, an optionally substituted aryl, an optionally substituted heteroaryl, a halogen atom, an optionally substituted amino, an optionally substituted acyl, an optionally substituted thiol, and an optionally substituted hydroxy, etc., and further an oxo, etc. may be exemplified, provided that when the substituent is an oxo, then a benzoic acid ester is not included. The number of said substituent may be 1 to 5, preferably 1 to 2, at any substitution possible position.

The substituents of said "optionally substituted lower alkyl", "optionally substituted aryl", "optionally substituted heteroaryl", a halogen atom, an optionally substituted amino, an optionally substituted acyl, "optionally substituted hydroxy group" and "optionally substituted thiol" are the same as those as defined in the "optionally substituted aryl", the "optionally substituted heteroaryl" for $Ar^2$, and the "optionally substituted arylene" or the "optionally substituted heteroarylene" for $Ar^1$.

The substituent of the "optionally substituted lower alkylene" for $W^1$ and $W^2$ is preferably methyl, ethyl, 1-propyl, 2-propyl, cyclopropyl, cyclobutyl, cyclopentyl, benzyl, phenethyl, pyridylmethyl, trifluoromethyl, phenyl, pyrrole, thiophene, pyridine, fluorine, methylamino, dimethylamino, acethylamino, acetyl, benzoyl, methylthio, ethylthio, methoxy, ethoxy, 1-propyloxy, 2-propyloxy, oxo, etc.

The alkoxycarbonyl for $R^1$ includes, for example, a carbonyl having a straight chain or branched chain $C_1$-$C_8$ alkoxy such as methoxy, ethoxy, propoxy, 2-propoxy, 2-methylpropoxy, butoxy, 2-methyl-2-propoxy, etc., and preferable one is methoxycarbonyl, ethoxycarbonyl, propoxycarbonyl, 2-propoxycarbonyl.

The optionally substituted carbamoyl for $R^1$ includes, for example, a straight chain or branched chain $C_1$-$C_8$ alkylaminocarbonyl or a straight chain or branched chain $C_2$-$C_{12}$ dialkylaminocarbonyl. The straight chain or branched chain $C_1$-$C_8$ alkylaminocarbonyl includes, for example, methylaminocarbonyl, ethylaminocarbonyl, propylaminocarbonyl, 2-propylaminocarbonyl, butylaminocarbonyl, etc., and preferable one is a straight chain or branched chain $C_1$-$C_4$ alkylaminocarbonyl. The straight chain or branched chain $C_2$-$C_{12}$ dialkylaminocarbonyl includes, for example, a carbamoyl substituted by the same or different alkyl groups, such as dimethylaminocarbonyl, diethylaminocarbonyl, dipropylaminocarbonyl, diisopropylaminocarbonyl, dibutylaminocarbonyl, ethylmethylaminocarbonyl, methylpropylaminocarbonyl, butylmethylaminocarbonyl, ethylbutylaminocarbonyl, dicyclohexylaminocarbonyl, etc., and preferable one is a straight chain or branched chain $C_2$-$C_8$ dialkylaminocarbonyl.

The optionally substituted cyclic aminocarbonyl for $R^1$ includes, for example, a 5- to 7-membered cyclic amino group optionally containing an oxygen atom, a sulfur atom, or a nitrogen atom as a ring-forming atom, which may be further optionally substituted by a $C_1$-$C_8$ alkyl, a hydroxy group, etc., such as pyrrolidino, piperidino, piperazinyl, 4-methylpiperazinyl, morpholino, thiomorpholino, 4-hydroxypiperidino, etc., and preferable one is pyrrolidino, morpholino, 4-hydroxypiperidino, 4-methylpiperazinyl.

The optionally substituted alkylsulfonylcarbamoyl for $R^1$ includes, for example, ones having an optionally substituted straight chain or branched chain $C_1$-$C_8$ alkylsulfonyl, such as methanesulfony, ethanesulfonyl, 1-propane-sulfonyl, 2-propanesulfonyl, butanesulfonyl, trifluoromethanesulfonyl, phenyl-methylsulfonyl, pyridylmethylsulfonyl, etc., and preferable one is methane-sulfonyl, ethanesulfonyl, 2-propanesulfonyl.

The optionally substituted arylsulfonylcarbamoyl for $R^1$ includes, for example, benzenesulfonyl, 4-methylbenzenesulfonyl, 4-chlorobenzenesulfonyl, 4-trifluoromethylbenzenesulfonyl, 3-methylbenzenesulfonyl, 1-naphthylsulfonyl, 2-naphthylsulfonyl, etc., and preferable one is benzenesulfonyl.

The lower alkyl of the "optionally substituted lower alkyl" for $R^{10}$ includes, for example, a straight chain $C_1$-$C_{10}$ alkyl or a $C_3$-$C_{10}$ alkyl having a cyclic structure, and preferable one is a straight chain $C_1$-$C_5$ alkyl or a $C_3$-$C_5$ alkyl containing a cyclic structure, such as methyl, ethyl, 2-propyl, etc.

The substituent of said "optionally substituted $C_1$-$C_8$ alkyl for $R^{10}$" includes, for example, a halogen, a $C_1$-$C_3$ straight chain or branched chain alkoxy, a $C_1$-$C_3$ straight chain or branched chain alkyl, trifluoromethyl, trifluoromethoxy, phenyl, pyridyl, etc., and preferable one is fluorine, chlorine, methoxy, ethoxy, 2-propoxy, methyl, ethyl, 2-propyl, trifluoromethyl, trifluoro-methoxy, phenyl, pyridyl.

The halogen atom for R2 is, for example, fluorine, chlorine, bromine, iodine, and preferable ones are fluorine, chlorine.

The alkyl of the "optionally substituted alkyl" for $R^2$ is, for example, a $C_1$-$C_8$ straight chain, branched chain or an alkyl having a cyclic structure, and preferable one is methyl, ethyl, 2-propyl, cyclopropyl, cyclopropylmethyl, etc.

The aryl of the "optionally substituted aryl" for $R^2$ is, for example, phenyl, 1-naphthyl, 2-naphthyl, etc., and preferable one is phenyl.

The heteroaryl of the "optionally substituted heteroaryl" for $R^2$ is the same ones as defined above for the "heteroaryl of the optionally substituted heteroaryl for $Ar^2$", and preferable one is thiophene, furan, pyrrole, pyridine, etc.

The optionally substituted thiol for $R^2$ is the same as those as defined above for the "substituent of the aryl or heteroaryl for $Ar^2$", and preferable one is methylthio, ethylthio, 2-propylthio, benzylthio, phenylthio, pyridylthio, imidazolylthio, etc.

The substituent of the "optionally substituted alkyl, optionally substituted aryl, optionally substituted heteroaryl" for $R^2$ includes, for example, a halogen, a $C_1$-$C_3$ straight chain or branched chain alkoxy, a $C_1$-$C_3$ straight chain or branched chain alkyl, trifluoromethyl, trifluoromethoxy, etc., and preferable one is fluorine, chlorine, methoxy, ethoxy, 2-propoxy, methyl, ethyl, 2-propyl, trifluoromethyl, trifluoromethoxy, etc.

The halogen atom, the "optionally substituted alkyl", the "optionally substituted aryl", the "optionally substituted heteroaryl", the "optionally substituted thiol" for $R^3$ are the same as those as defined for $R^2$.

The "optionally substituted hydroxy, optionally substituted non-aromatic heterocyclic group, optionally substituted amino, optionally substituted acyl, or alkylsulfonyl" for $R^3$ are the same as those defined above for the "substituents of the aryl or heteroaryl for $Ar^2$", and preferable one is methoxy, ethoxy, 2-propoxy, trifluoromethoxy, methanesulfonyl, etc.

The substituent of the heteroaryl of the formula (7) includes, for example, a halogen atom, an optionally substituted alkyl, an optionally substituted aryl, an optionally substituted heteroaryl, an optionally substituted thiol, an optionally substituted hydroxy, an optionally substituted non-aromatic heterocyclic group, an optionally substituted amino, an optionally substituted acyl, and an alkylsulfonyl, and preferable one is the same as exemplified for $R^3$, respectively.

The "prodrug" means a compound, which can be hydrolyzed chemically or biochemically in the living body and converted into the compound of the present invention. For example, when the heteroaryl compound of the present invention has a carboxyl group, then a compound wherein said carboxyl group is converted into a suitable ester group is a prodrug thereof. Preferable examples of the ester are methyl ester, ethyl ester, 1-propyl ester, 2-propyl ester, pivaloyloxymethyl ester, acetyloxymethyl ester, cyclohexylacetyloxymethyl ester, 1-methylcylohexylcarbonyloxymethyl ester, ethyloxycarbonyloxy-1-ethyl ester, cyclohexyloxycarbonyloxy-1-ethyl ester, etc.

The "pharmaceutically acceptable salt" includes, for example, an alkali metal salt such as sodium salt, potassium salt, etc., an alkaline earth metal salt such as calcium salt, magnesium salt, etc., an inorganic metal salt such as zinc salt, a salt with an organic base such as triethylamine, triethanolamine, trihydroxymethylaminomethane, amino acid, etc., when the heteroaryl compound of the present invention or a pharmaceutically acceptable salt thereof has an acidic group. When the heteroaryl compound of the present invention or a pharmaceutically acceptable salt thereof has a basic group, the pharmaceutically acceptable salt includes, for example, a salt with an inorganic acid such as hydrochloride, hydrobromide, sulfate, phosphate, nitrate, etc., a salt with an organic acid such as acetate, propionate, succinate, lactate, malate, tartrate, citrate, maleate, fumarate, methanesulfonate, p-toluenesulfonate, benzenesulfonate, ascorbate, etc.

The present invention includes a prodrug of the heteroaryl compound of the formula (1). Besides, the present invention also includes hydrates and solvates such as ethanolates of the heteroaryl compounds of the formula (1), a prodrug thereof, and a pharmaceutically acceptable salt thereof.

The heteroaryl compound of the present invention may be prepared, for example, by the methods disclosed hereinafter in detail, or a modified method of those methods.

The compounds to be used as a starting compound may be used in the form of a salt thereof.

The heteroaryl moiety of the heteroaryl compound of the present invention may be prepared by a conventional method, for example, methods disclosed in The Chemistry of Heterocyclic Compounds (cf., pyrrole derivatives vol. 48 part 1, part 2; pyrazole derivatives: vol. 22; imidazole derivatives: vol. 6 part 1; triazole derivatives: vol. 6 part 1; indole derivatives: vol. 25 part II, part III, part 4; indazole derivatives: vol. 22; benzimidazole derivatives: vol. 40 part 1, part 2, etc.), Methoden der Organischen Chemie (Houben-Weyl) (cf., pyrrole derivatives: Hetarene I, TEIL 1, E6a, p 556-798; pyrazole derivatives: Hetarene III, TEIL 2, E8b, p 399-710; imidazole derivatives: Hetarene III, TEIL 3, E8c, p 1-215; triazole derivatives: Hetarene II, TEIL 2, E7b, p 286-686; indole derivatives: Hetarene I, TEIL 2a, E6b1, p 546-848, E6b2, p 849-1336; indazole derivatives: Hetarene III, TEIL 2, E8b, p764-856; benzimidazole derivatives: Hetarene III, TEIL 3, E8c, p 216-391, etc.), Comprehensive Heterocyclic Chemistry (cf., pyrrole derivatives, indole derivatives: vol. 4; pyrazole derivatives, indazole derivatives: vol. 5; imidazole derivatives, benzimidazole derivatives: vol. 5; triazole derivatives: vol.5; thiophene derivatives: vol. 5; benzthiophene derivatives: vol. 6, etc.), Comprehensive Heterocyclic Chemistry II (cf., pyrrole derivatives, indole derivatives: vol. 2; pyrazole derivatives, indazole derivatives: vol. 3; imidazole derivatives, benzimidazole derivatives: vol. 3; triazole derivatives: vol. 4, etc.), Chemistry of heterocyclic compounds (Kodansha, published in 1988), Shin-Jikken-Kagaku Koza, vol. 14 [IV] (Maruzen, published in 1977), WO 02/085851, WO 02/10131-A1, WO 03/91211-A1, WO 04/048341, etc., or a modified method thereof.

The reactions as disclosed in the above are merely exemplified for illustrative purpose, and the present compounds can be suitably prepared by methods other than the above, based on the knowledge of persons who may well know the organic chemistry.

In each reaction as mentioned below, a functional group can be protected if necessary. The protecting groups to be employed and the techniques for protection or deprotection thereof are disclosed in detail in the literature of T. W. Greene and P. G. M. Wuts, "Protecting Groups in Organic Synthesis", the 3rd edition, JOHN WILEY & SONS, INC., New York (1999).

Process (1)

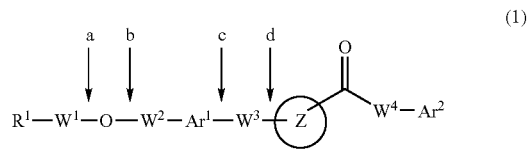

The heteroaryl derivative of the formula (1) may be prepared by forming the bond at the parts of a-d. The method for forming a bond at the parts of a-d can be illustrated as shown in Process (1-1)-(1-3). The order of the forming a bond at the parts of a-d may be appropriately changed. The starting compounds in each Process may be prepared from conventional starting materials by combining the methods for bond-forming at the parts of a-d.

Process (1-1): Synthesis of the Parts a, b

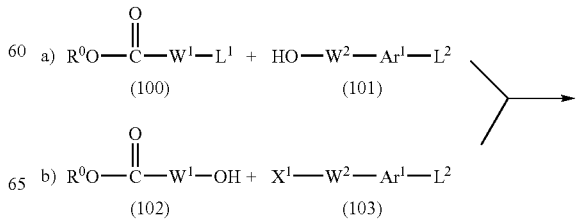

-continued

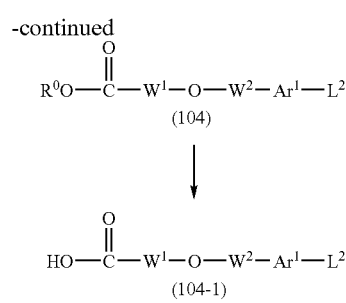
(104)

↓

(104-1)

(wherein $R^0$ is an alkyl such as methyl, ethyl, t-butyl, etc.; $L^1$, $L^2$ are independently chlorine, bromine, iodine; $X^1$ is a leaving groups such as chlorine, bromine, iodine, triflate, etc., and the other symbols are as defined above)

Compound (100), Compound (101), Compound (102), and Compound (103) may be prepared by the methods disclosed in Shin-Jikken-Kagaku Koza, vol. 14 (Maruzen, published in 1977), Jikken-Kagaku Koza vol. 19 to 26 (Maruzen, published in 1992), Fine Organic Synthesis (Nankodo, published in 1983), Fundamentals and Experiments of Peptide synthesis (Maruzen, published in 1985), Compendium of Organic Synthetic Methods, Vol. 1-9 (John Wiley & Sons), Comprehensive Organic Synthesis, Vol. 1-9 (1991, Pergamon Press), Comprehensive Organic Transformations (1989, VCH Publishers), etc., or a modified method thereof.

Compound (104) may be prepared by reacting Compound (100) and Compound (101), or Compound (102) and Compound (103), in an inert solvent in the presence of a base. Namely, Compound (104) may be prepared by O-alkylation reaction disclosed in Jikken Kagaku Koza, vol. 20 (Maruzen, published in 1992), J. Org. Chem, 56, 1321 (1991), Heterocycles, 31, 1745 (1990), etc., or a modified method thereof.

The inert solvent includes, for example, ethers (e.g., ether, tetrahydrofuran (THF), dioxane, etc.), hydrocarbons (e.g., toluene, benzene, xylene, etc.), halogenated hydrocarbons (e.g., dichloromethane, chloroform, dichloroethane, carbon tetrachloride, etc.), aprotic solvents (e.g., dimethylsulfoxide, N,N-dimethylformamide, acetonitrile, etc.). These solvents may be used by mixing two or more thereof at an appropriate ratio.

The base includes, for example, alkali metal hydrides (e.g., sodium hydride, potassium hydride, etc.), alkali metal carbonates (e.g., potassium carbonate, sodium carbonate, sodium hydrogen carbonate, cesium carbonate, etc.), alkylamines (e.g., triethylamine, ethyldiisopropylamine, etc.), alkali metal alkoxides (e.g., sodium methoxide, potassium t-butoxide, etc.).

The reaction temperature may be selected from a range of about −20° C. to a boiling point of the solvent, and preferably from a range of about 0° C. to a boiling point of the solvent.

Compound (104-1) may be prepared by de-protecting Compound (104) by a conventional method. For example, Compound (104-1) may be prepared by subjecting Compound (104) to hydrolysis in the presence of an acid or a base.

The acid includes, for example, hydrochloric acid, sulfuric acid, acetic acid, hydrobromic acid, trifluoroacetic acid, methanesulfonic acid, etc.

The solvent includes, for example, ethers (e.g., ether, THF, dioxane, etc.), aprotic solvents (e.g., acetone, dimethylsulfoxide, N,N-dimethylformamide, acetonitrile, etc.), alcohols (e.g., methanol, ethanol, etc.), and these solvents may be used by mixing one or more thereof with water at an appropriate ratio. The reaction can be carried out without a solvent.

The reaction temperature is selected from a range of about −20° C. to a boiling point of the solvent, and preferably from a range of about −10° C. to a boiling point of the solvent.

The base includes, for example, an alkali metal hydroxide (e.g., sodium hydroxide, potassium hydroxide, lithium hydroxide, etc.), an alkali metal carbonate (e.g., potassium carbonate, sodium carbonate, potassium hydrogen carbonate, sodium hydrogen carbonate, etc.), and the reaction is carried out in an aqueous solvent.

The aqueous solvent is a mixed solvent of water and one or more solvents selected from ethers (e.g., ether, THF, dioxane, etc.), aprotic solvents (e.g., acetone, dimethylsulfoxide, N,N-dimethylformamide, acetonitrile, etc.), alcohols (e.g., methanol, ethanol, etc.) at an appropriate ratio.

The reaction temperature is selected from a range of about −20° C. to a boiling point of the solvent, and preferably from a range of about −10° C. to a boiling point of the solvent.

Process (1-2): Synthesis of the Parts c, d

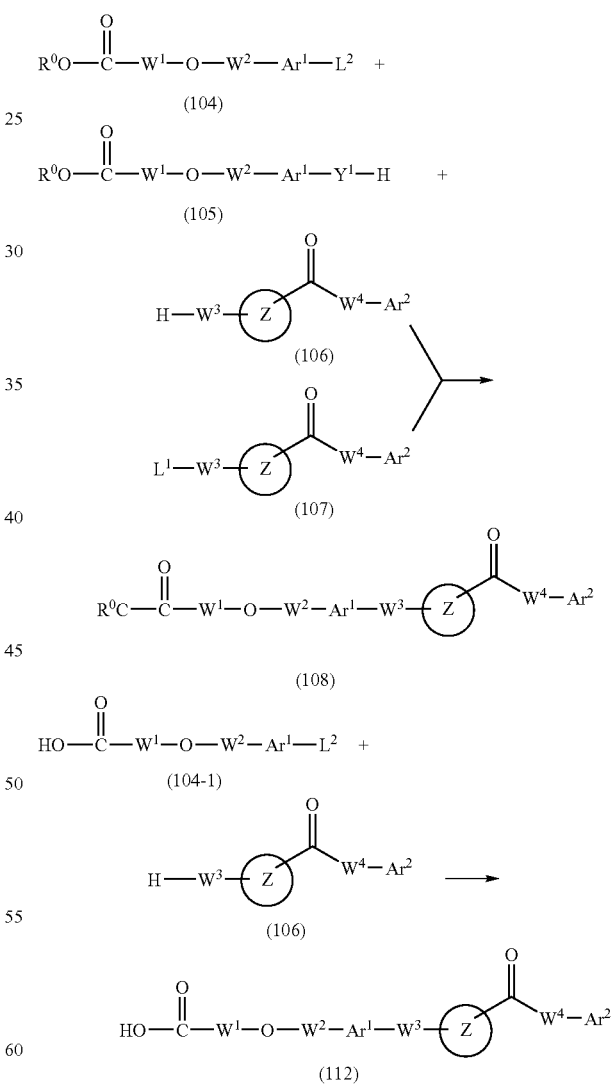

(wherein all of the symbols are as defined above)

The method for bond-forming at the part c, the method for bond-forming at the part d, and the process for preparing Compounds (106), (107) are carried out by the methods disclosed in WO 02/085851, WO 02/10131-A1, WO 03/91211-A1, WO 04/048341, Organic Letters, 4, 973 (2002), Tetrahedron Letters, 40, 2657 (1997), Chemical Communications, 188 (2004), or a modified method thereof.

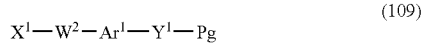  (109)

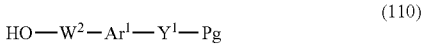  (110)

  (111)

(wherein Pg is a protecting group, and the other symbols are as defined above)

Compound (109) and Compound (110) are prepared, for example, by the method disclosed in Shin-Jikken Kagaku Koza, vol. 14 (Maruzen, published in 1977), Jikken Kagaku Koza, vol. 19-26 (Maruzen, published in 1992), Fine Organic Synthesis (Nankodo, published in 1983), Compendium of Organic Synthetic Methods, Vol. 1-9 (John Wiley & Sons), etc., or a modified method thereof.

Process (1-3)

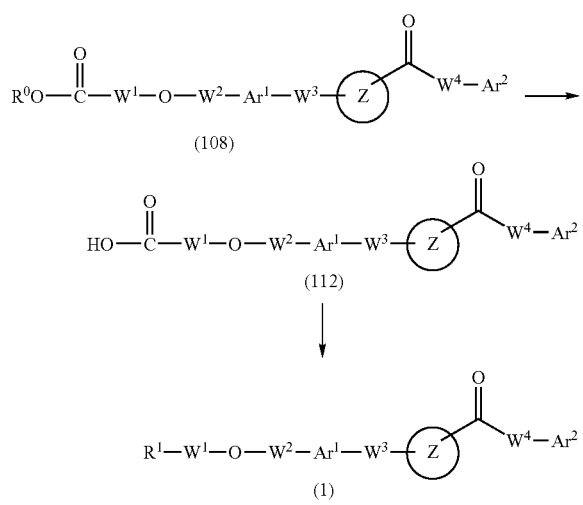

(wherein $R^1$ is an alkoxycarbonyl group, an optionally substituted carbamoyl group, an optionally substituted cyclic aminocarbonyl group, an optionally substituted alkylsulfonylcarbamoyl group, an optionally substituted arylsulfonylcarbamoyl group, or a tetrazolyl group among the definitions as defined above, and the other symbols are as defined above)

Compound (112) may be prepared from Compound (108) by using a conventional deprotection technique, for example, by hydrolysis in the presence of an acid or a base.

The acid includes, for example, hydrochloric acid, sulfuric acid, acetic acid, hydrobromic acid, trifluoroacetic acid, methansulfonic acid, etc.

The solvent includes, for example, ethers (e.g., ether, THF, dioxane, etc.), aprotic solvents (e.g., acetone, dimethylsulfoxide, N,N-dimethylformamide, acetonitrile, etc.), alcohols (e.g., methanol, ethanol, etc.), and these solvents may be used by mixing one or more thereof with water at an appropriate ratio. The reaction may also be carried out without a solvent.

The reaction temperature is selected from a range of about −20° C. to a boiling point of the solvent, preferably from a range of about −10° C. to a boiling point of the solvent.

The base includes, for example, an alkali metal hydroxide (e.g., sodium hydroxide, potassium hydroxide, lithium hydroxide, etc.), an alkali metal carbonate (e.g., potassium carbonate, sodium carbonate, potassium hydrogen carbonate, sodium hydrogen carbonate, etc.), and the reaction is carried out in an aqueous solvent.

The aqueous solvent is a mixed solvent of water and one or more solvents selected from ethers (e.g., ether, THF, dioxane, etc.), aprotic solvents (e.g., acetone, dimethylsulfoxide, N,N-dimethylformamide, acetonitrile, etc.), alcohols (e.g., methanol, ethanol, etc.) at an appropriate ratio.

The reaction temperature is selected from a range of about −20° C. to a boiling point of the solvent, and preferably from a range of about −10° C. to a boiling point of the solvent.

Compound (1) may be prepared from Compound (112) by a conventional method such as the methods disclosed in Shin-Jikken Kagaku Koza, vol. 14 (Maruzen, published in 1977), Jikken Kagaku Koza, vol. 19 to 26 (Maruzen, published in 1992), Fine Organic Synthesis (Nankodo, published in 1983), Fundamentals and Experiments of Peptide Synthesis (Maruzen, published in 1985), Compendium of Organic Synthetic Methods, Vol. 1-9 (John Wiley & Sons), Comprehensive Organic Synthesis, Vol. 1-9 (1991, Pergamon Press), Comprehensive Organic Transformations (1989, VCH Publishers), J. Org. Chem., 56, 2395 (1991), Org. Synth. 3, 646 (1955), Org. Synth. 29, 75 (1949), Org. Synth. 50, 18 (1970), Org. Synth. 50, 52 (1970), J. Org. Chem., 64, 2322 (1999), Tetrahedron Lett., 41, 6981 (2000), Org. Lett., 2, 2789 (2000), Org. Lett., 3, 193 (2001), J. Org. Chem., 57, 5285 (1992), J. Org. Chem., 66, 7945 (2001), etc. or a modified method thereof.

This reaction shows a conversion reaction from —$CO_2H$ to an alkoxycarbonyl group, an optionally substituted carbamoyl group, an optionally substituted cyclic aminocarbonyl group, an optionally substituted alkylsulfonylcarbamoyl group, an optionally substituted arylsulfonylcarbamoyl group, a tetrazolyl group, or a conversion reaction from —$CO_2H$ to a cyano group and a conversion reaction from a cyano group to a tetrazolyl group.

Process (2) Method for Construction of Ring Z

Process (2-1)

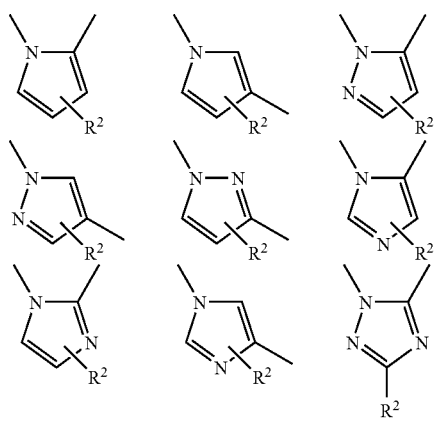

-continued

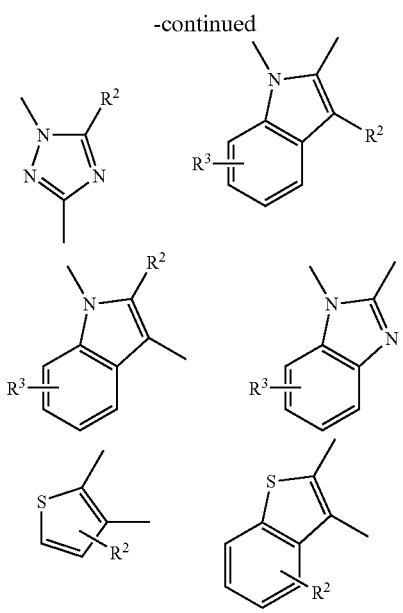

When Ring Z having a substituent R² is needed, it is prepared, for example, by the method disclosed in the above-mentioned Comprehensive Heterocyclic Chemistry (cf., pyrrole derivatives, indole derivatives: vol. 4; pyrazole derivatives, indazole derivatives: vol. 5; imidazole derivatives, benzimidazole derivatives: vol. 5; triazole derivatives: vol. 5; thiophene derivatives: vol. 5; benzothiophene derivatives: vol. 6, etc.), Comprehensive Heterocyclic Chemistry II (cf., pyrrole derivatives, indole derivatives: vol. 2; pyrazole derivatives, indazole derivatives: vol. 3; imidazole derivatives, benzimidazole derivatives: vol. 3; triazole derivatives: vol. 4, etc.), etc. or a modified method thereof.

For example, when Ring Z is an imidazole, then Compound (117) is prepared, for example, by heating Compound (115) or Compound (116) with formamide at a temperature of 150 to 200° C.

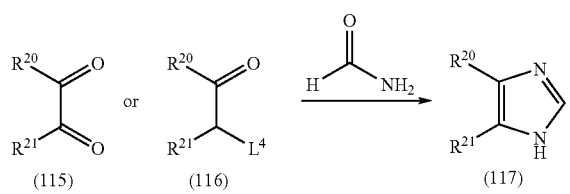

(wherein R²⁰ and R²¹ are independently a hydrogen atom, a halogen atom, an optionally substituted alkyl, an optionally substituted aryl, an optionally substituted heteroaryl, or an optionally substituted thiol, and L⁴ is a hydroxy group, an amino, bromine, chlorine, etc.)

In addition, when bromine or iodine exists for R² and R³ as a substituent on Ring Z, an aryl or a heteroaryl can be introduced into R² or R³ by Suzuki Coupling Reaction with an aryl boronate or a heteroaryl boronate (by the method disclosed in J. Organomet. Chem, 576, 147 (1999), J. Am. Chem. Soc, 122, 4020 (2000), J. Am. Chem. Soc, 124, 6343 (2002), or a modified method thereof, Stille Coupling Reaction with an aryl-tin compound or a heteroaryl-tin compound (by the method disclosed in Angew. Chem. Int. Ed. Engl, 25, 508 (1986) or a modified method thereof, etc.

Process (2-2)

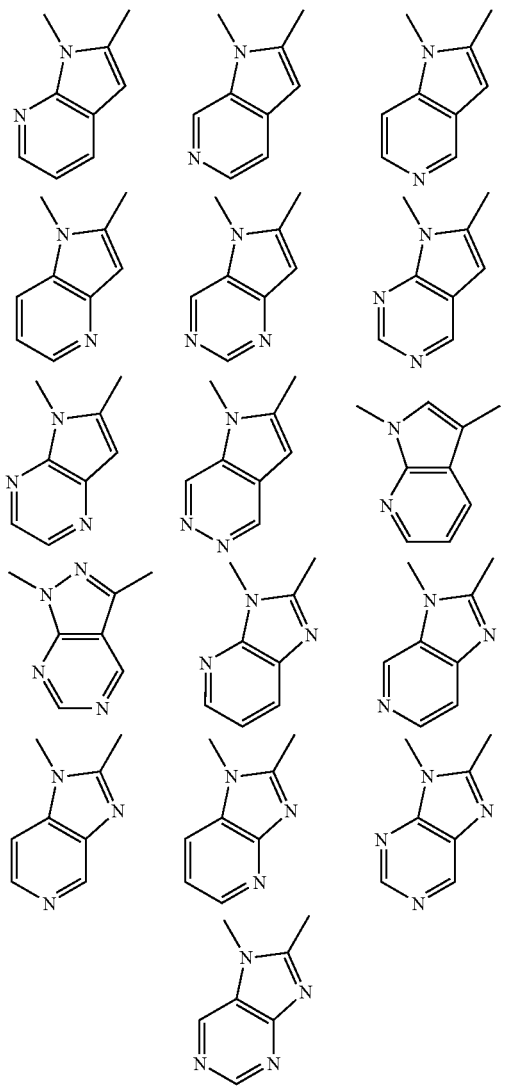

The heteroaryl ring of the formula (7) may be prepared, for-example, by the method disclosed in Tetrahedron, 53, 3637 (1997), Tetrahedron Lett., 39, 5159 (1998), Tetrahedron, 49, 2885 (1993), Synthesis, 877 (1996), J. Heterocycl. Chem., 6, 775 (1969), Heterocycles, 34, 2379 (1992), Bioorg. Med. Chem. Lett., 10, 2171 (2000), Bioorg. Med. Chem. Lett., 10, 2167 (2000), Angew. Chem. Int. Ed., 39, 2488 (2000), Tetrahedron, 54, 2931 (1998), J. Org. Chem., 48, 1060 (1983), J. Org. Chem., 30, 1528 (1965), J. Org. Chem., 65, 7825 (2000), J. Med. Chem., 16, 1296 (1973), Tetrahedron, 48, 10549 (1992), Heterocycles, 41, 161 (1995), etc. or a modified method thereof.

The heteroaryl derivative of the present invention or a prodrug thereof may exist in an asymmetric form or may have a substituent having an asymmetric carbon atom, and in those cases, the present compounds may exist in the form of an optical isomer. The present compounds also include a mixture of these isomers or each isolated isomer. Such optical isomers may be purely isolated, for example, by optical resolution.

The optical resolution may be carried out, for example, by forming a salt with an optically active acid (e.g., monocarboxylic acids such as mandelic acid, N-benzyloxyalanine, lactic acid, etc., dicarboxylic acids such as tartaric acid, o-diisopropyridentartaric acid, malic acid, etc., sulfonic acids such as camphersulfonic acid, bromocamphorsulfonic acid, etc.) in an inert solvent (e.g., alcohols such as methanol, ethanol, 2-propanol, etc., ethers such as diethyl ether, etc., ester solvents such as ethyl acetate, etc., aromatic hydrocarbons such as toluene, etc., acetonitrile, or a mixture of these solvents).

When the heteroaryl derivative of the present invention or a prodrug thereof or an intermediate thereof has an acidic substituent such as carboxyl group, then it can be made to form a salt with an optically active amine (e.g., organic amines such as α-phenethylamine, 1,2-diphenyl-ethanolamine, (1R,2R)-(−)-2-amino-1,2-diphenylethanol, (1S,2R)-(+)-2-amino-1,2-diphenylethanol, quinine, quinidine, cinchonidine, cinchonine, strychnine, etc.).

The temperature for forming a salt may be in the range of room temperature to a boiling point of the solvent. In order to improve the optical purity, it is preferable to raise the reaction temperature to a temperature around the boiling point once. The precipitated salt is cooled, if necessary, prior to collection by filtration, and the yield thereof can be improved. The amount of the optically active acid or amine is in the range of about 0.5 to about 2.0 equivalents, preferably about 1 equivalent to the substrate. If necessary, the precipitated crystals are recrystallized in an inert solvent (e.g., alcohols such as methanol, ethanol, 2-propanol, etc., ethers such as diethyl ether, ester solvents such as ethyl acetate, etc., aromatic hydrocarbons such as toluene, etc., acetonitrile, etc., or a mixture thereof to give an optically active salt in high purity. If necessary, the obtained salt is treated with an acid or a base by a conventional method to give a free compound.

The heteroaryl derivative of the present invention or a salt thereof can be administered either orally or parenterally. When administered orally, it can be administered in a conventional dosage form. When administered parenterally, it can be administered in the form of topical administration formulations, injections, transdermal preparations, intranasal formulations, etc. The pharmaceutical composition for oral administration or rectal formulations are, for example, capsules, tablets, pills, powders, cachets, suppositories, liquids, etc. The injection preparations are, for example, aseptic solutions or suspensions. The pharmaceutical composition for topical administration is, for example, creams, ointments, lotions, transdermal preparations such as conventional patches, matrixes, etc.

The above formulations are prepared by a conventional method with pharmaceutically acceptable excipients and additives. The pharmaceutically acceptable excipients or additives are, for example, carriers, binders, flavors, buffering agents, thickening agents, coloring agents, stabilizers, emulsifiers, dispersing agents, suspending agents, antiseptic agents, etc.

The pharmaceutically acceptable carriers are, for example, magnesium carbonate, magnesium stearate, talc, sugar, lactose, pectin, dextrin, starch, gelatin, tragacanth, methyl cellulose, sodium carboxymethyl cellulose, wax of low melting point, cacao butter, etc. Capsules can be prepared by putting the present compound together with a pharmaceutically acceptable carrier into capsules. The present compound can be put into capsules without any excipient or by mixing with a pharmaceutically acceptable carrier. The cache formulations may also be prepared likewise.

The liquid preparations for injection are, for example, solutions, suspensions, emulsions, etc. For example, aqueous solutions, a solution of water and propylene glycol solution are exemplified. The liquid preparation may be prepared in the form of a solution of polyethyleneglycol or/and propyleneglycol which may contain moisture. The liquid preparation suitable for oral administration may be prepared by adding the present compound into water, and further adding thereto a coloring agent, a flavor, a stabilizer, a sweetening agent, a solubilizer, a thickening agent, etc. Further the liquid preparation suitable for oral administration may also be prepared by adding the present compound together with a dispersing agent into water and thickening the solution. The thickening agent is, for example, pharmaceutically acceptable naturally occurring or synthetic gum, resin, methyl cellulose, sodium carboxymethyl cellulose, or a conventional suspending agent.

The formulation for topical administration includes, for example, the above-mentioned liquid preparations, creams, aerosol, sprays, powders, lotions, ointments, etc. The abovementioned formulations for topical administration may be prepared by mixing the present compound with a conventional pharmaceutically acceptable diluent or carrier. The ointment and cream preparations are prepared by adding a thickening agent and/or gelatinizing agent into an aqueous or oily base, and formulating the resultant. The base includes, for example, water, parafin liquid, vegetable oils (e.g., peanut oil, castor oil, etc.), etc. The thickening agent includes, for example, soft paraffin, aluminum stearate, cetostearyl alcohol, propylene glycol, polyethylene glycol, lanoline, hydrogenated lanoline, bee wax, etc.

The lotion preparations may be prepared, for example, by adding one or more kinds of pharmaceutically acceptable stabilizers, suspending agents, emulsifiers, diffusing agents, thickening agents, coloring agents, flavors, etc. into an aqueous or oily base The powder preparations may be prepared by formulating together with a pharmaceutically acceptable base. The base includes, for example, talc, lactose, starch, etc. The drop preparations may be prepared by formulating together with an aqueous or non-aqueous base and one, or more kinds of pharmaceutically acceptable diffusing agents, suspending agents, solubilizers, etc.

The formulations for topical administration may optionally contain, if necessary, antiseptic agents and bacterial growth inhibitors such as methyl hydroxybenzoate, propyl hydroxybenzoate, chlorocresol, benzalkonium chloride, etc.

The heteroaryl derivative of the present invention or a salt thereof may be administered to a patient with diabetic mellitus, especially to a patient with type 2 diabetic mellitus or insulin-independent diabetes mellitus. Besides, the heteroaryl derivative of the present invention or a salt thereof can control the blood glucose level of a patient with diabetic mellitus. On such occasions, the dose, administration frequency may vary according to the conditions, ages, body weights of patients, or administration form, etc. When administered orally, then the dose of the present compound is in the range of about 1 to about 500 mg per day in adult, preferably in the range of about 5 to about 100 mg per day in adult, which is administered once a day or divided into several dosage units. When administered in the form of an injection, the dosage of the present invention is in the range of about 0.1 to about 300 mg per day in adult, preferably in the range of about 1 to about 100 mg per day in adult, which is administered once a day or divided into several dosage units.

The concrete examples of the compound of the formula (1) which is obtained by the present invention are compounds as listed in the following Table 1 to Table 6.

TABLE 1
| Comp. No. | Structure |
|---|---|
| 1 | 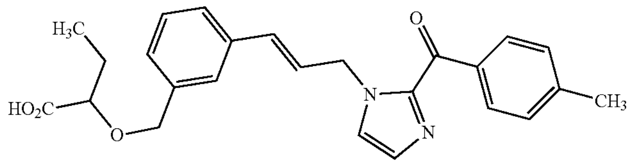 |
| 2 | 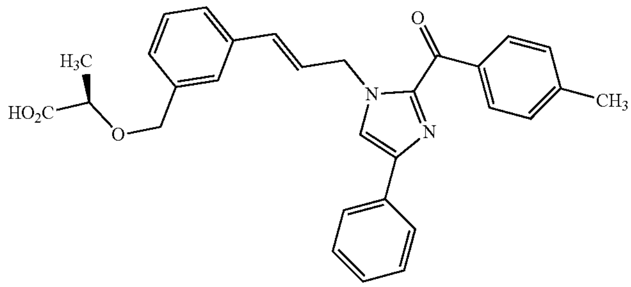 |
| 3 | 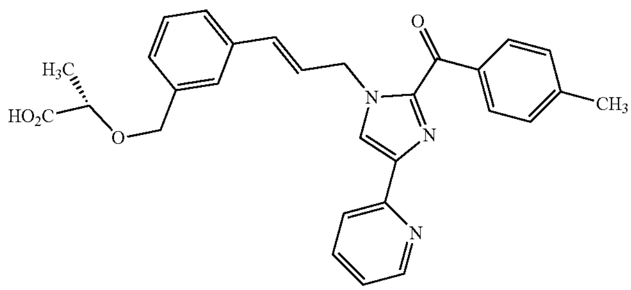 |
| 4 | 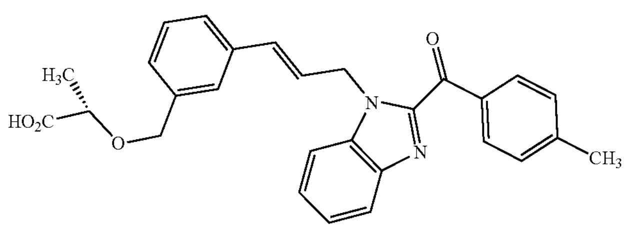 |
| 5 | 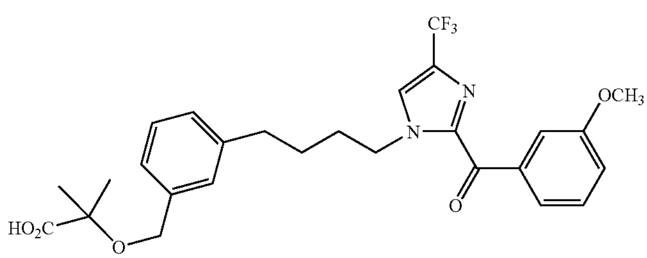 |
| 6 | 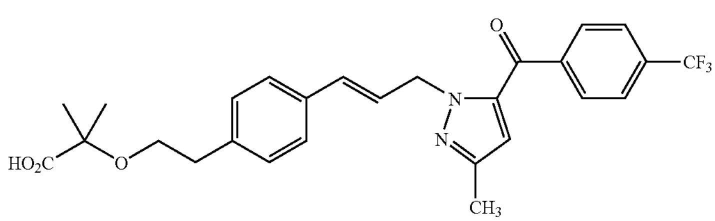 |
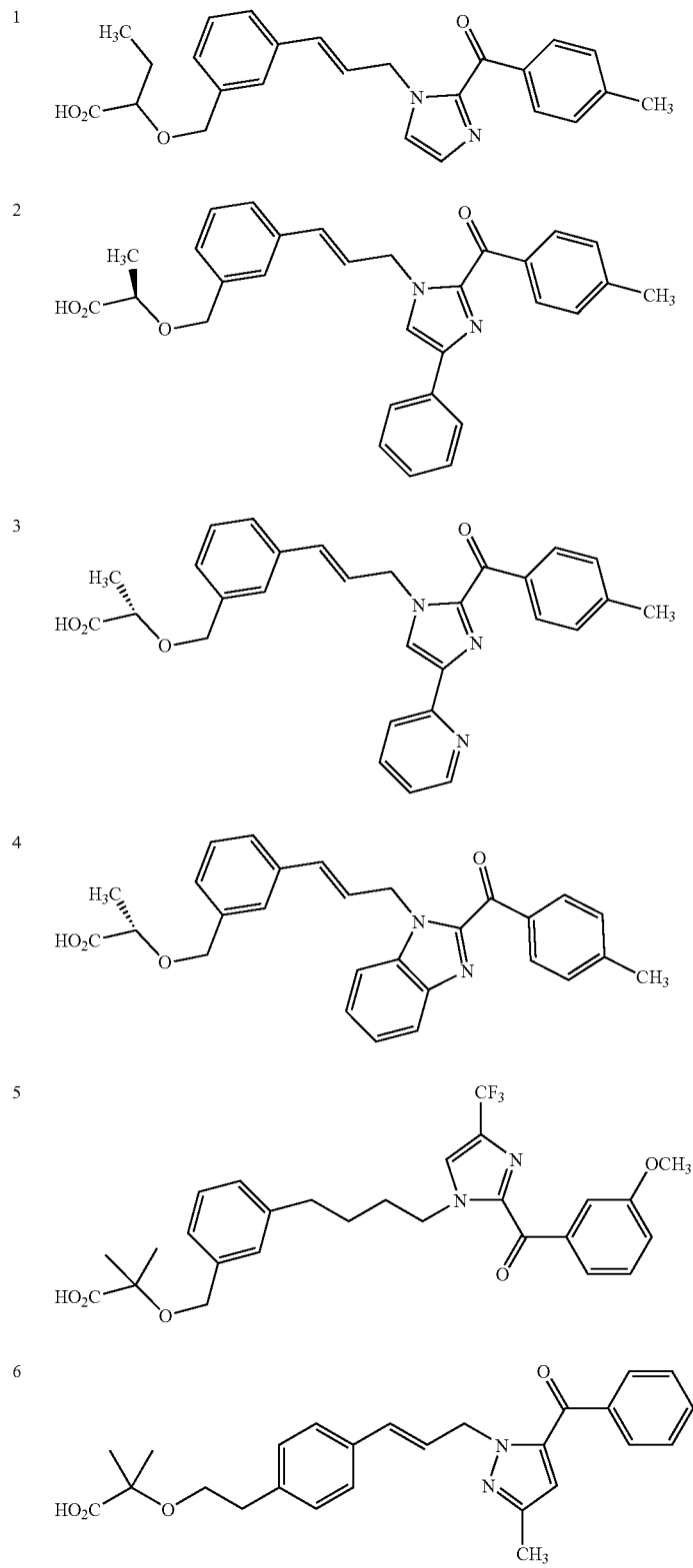

TABLE 1-continued

| Comp. No. | Structure |
|---|---|
| 7 | 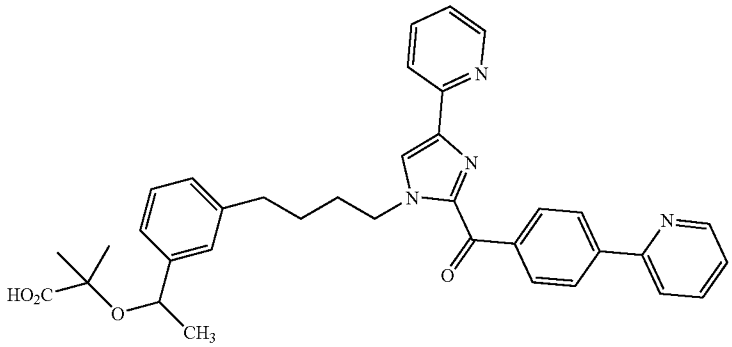 |
| 8 | 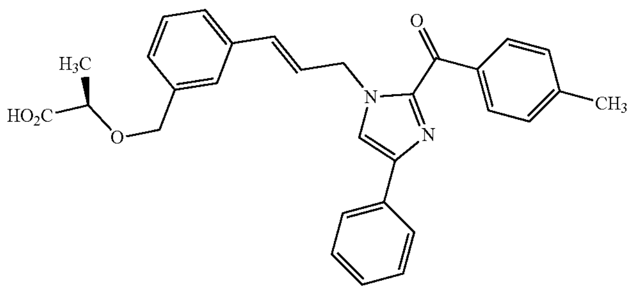 |
| 9 | 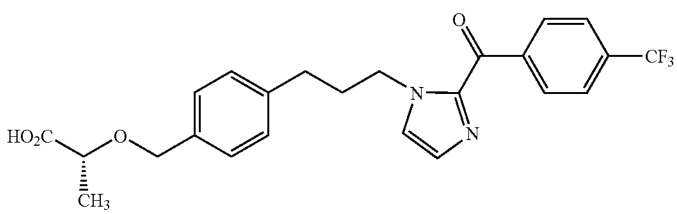 |
| 10 | 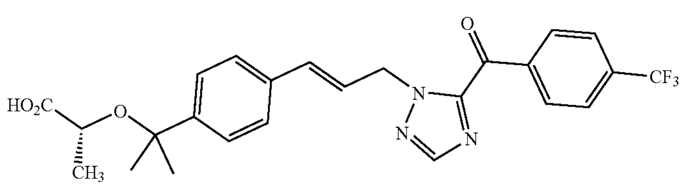 |
| 11 | 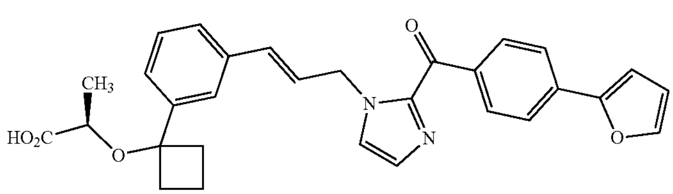 |
| 12 | 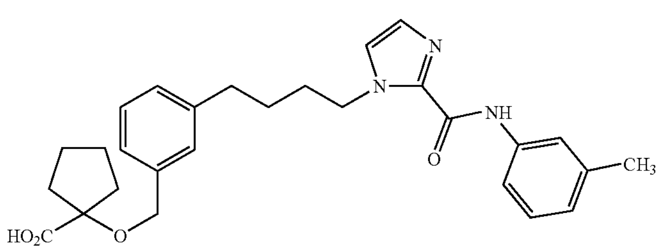 |

TABLE 2

| Comp. No. | Structure |
|---|---|
| 13 | 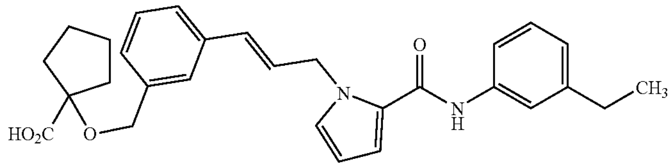 |
| 14 | 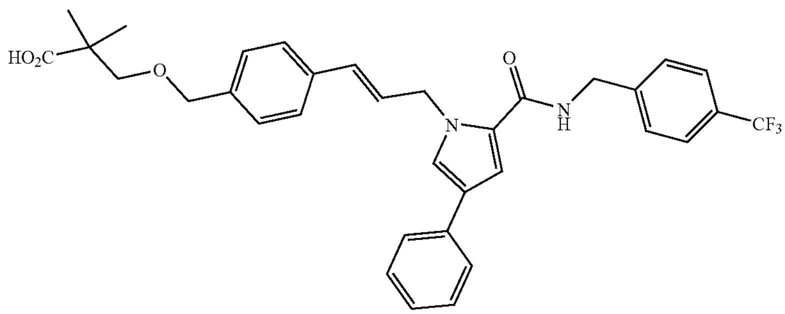 |
| 15 | 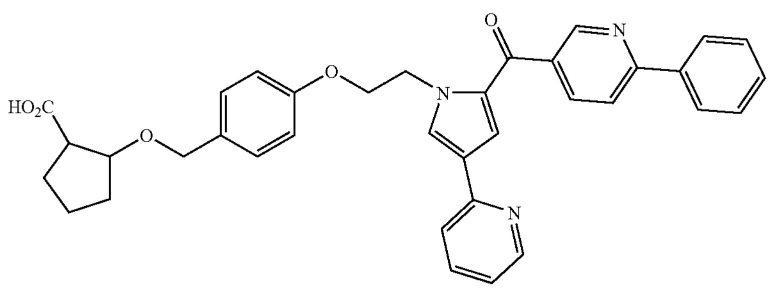 |
| 16 | 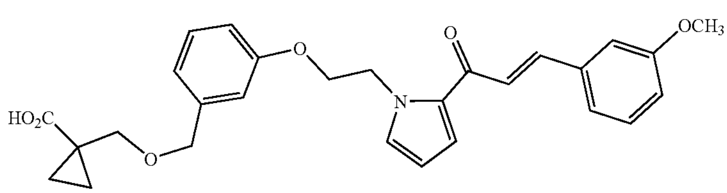 |
| 17 | 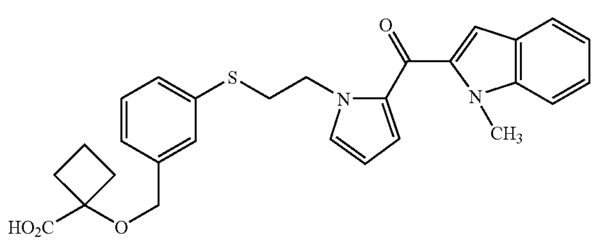 |
| 18 | 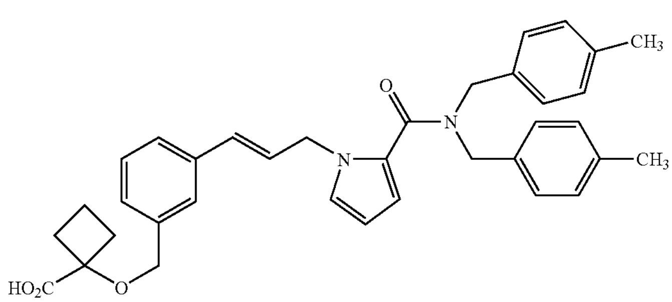 |

TABLE 2-continued

| Comp. No. | Structure |
|---|---|
| 19 | 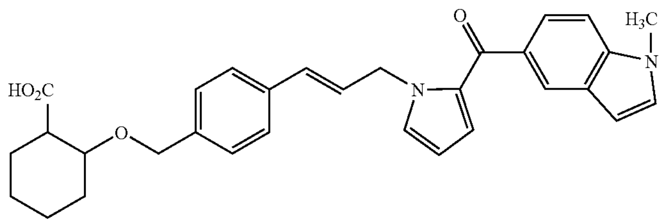 |
| 20 | 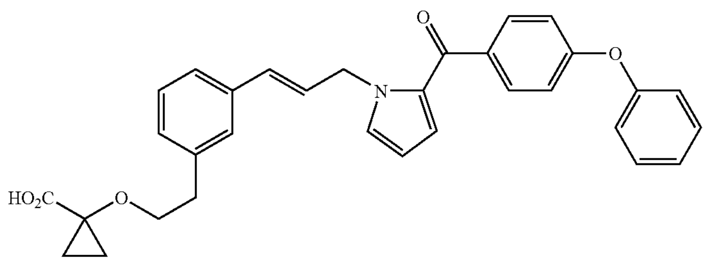 |
| 21 | 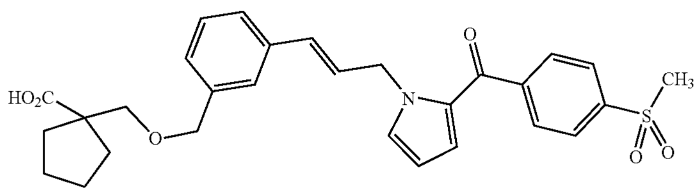 |
| 22 | 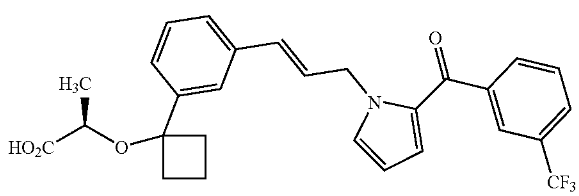 |
| 23 | 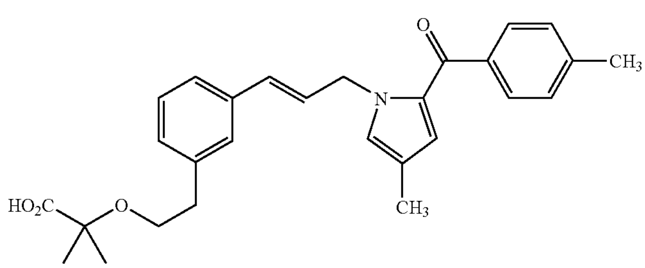 |
| 24 | 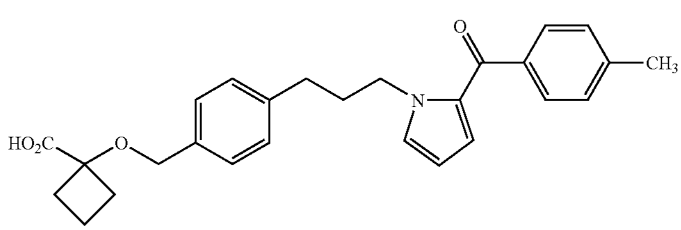 |

TABLE 3

| Comp. No. | Structure |
|---|---|
| 25 | 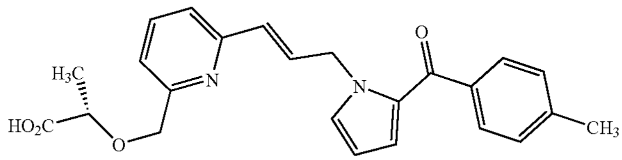 |
| 26 | 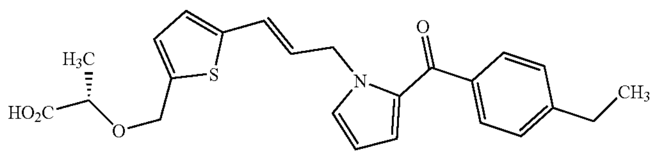 |
| 27 | 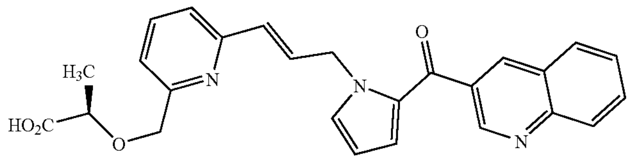 |
| 28 | 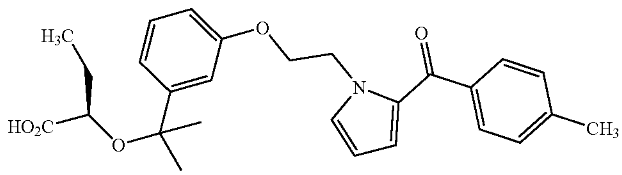 |
| 29 | 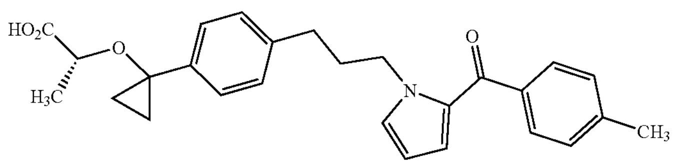 |
| 30 | 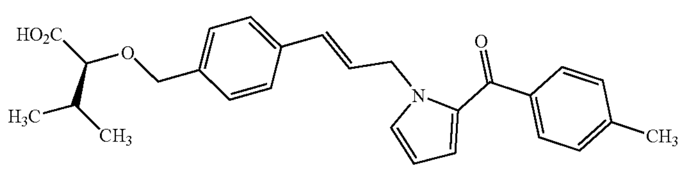 |
| 31 | 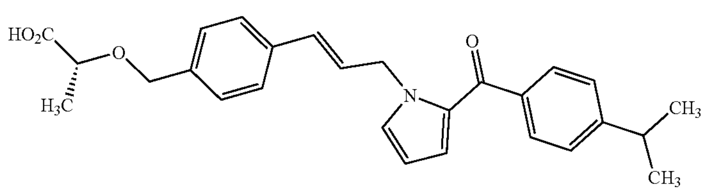 |
| 32 | 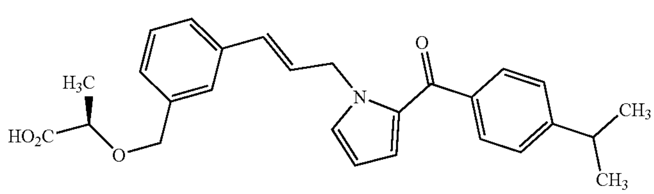 |

TABLE 3-continued
| Comp. No. | Structure |
|---|---|
| 33 | 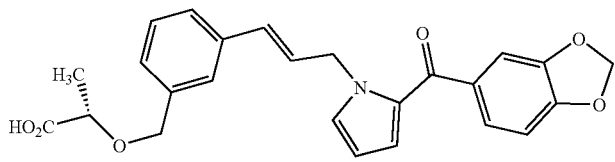 |
| 34 | 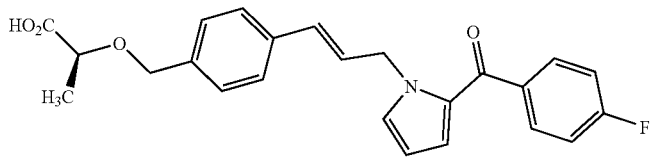 |
| 35 | 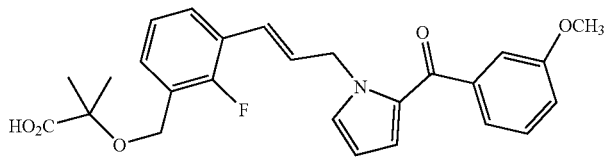 |
| 36 | 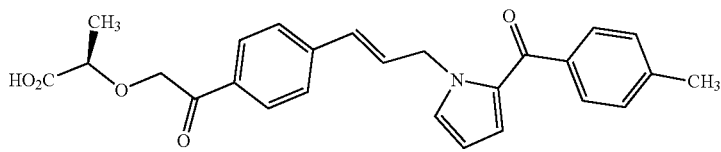 |
TABLE 4
| Comp. No. | Structure |
|---|---|
| 37 | 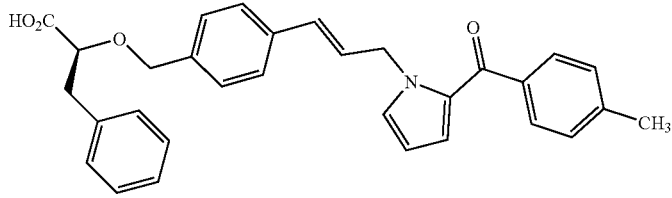 |
| 38 | 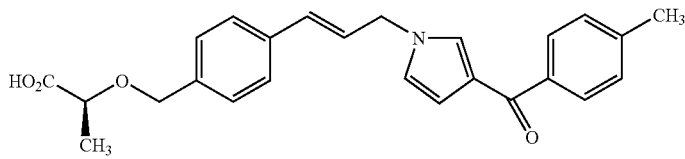 |
| 39 | 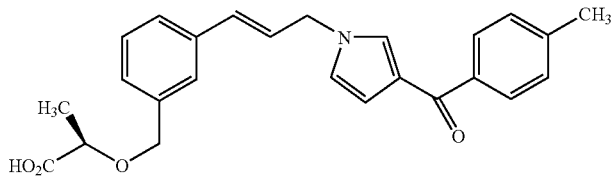 |

TABLE 4-continued

| Comp. No. | Structure |
|---|---|
| 40 | 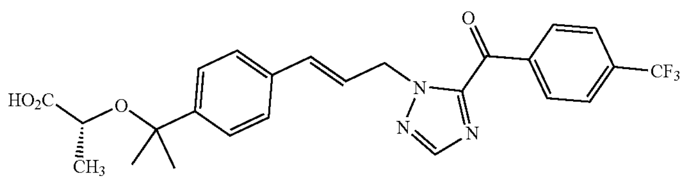 |
| 41 | 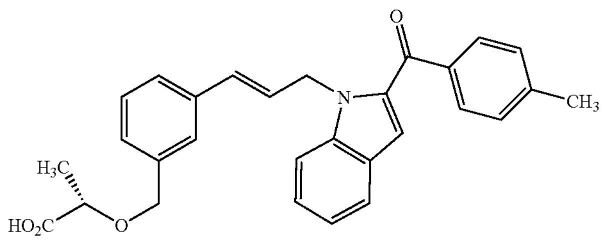 |
| 42 | 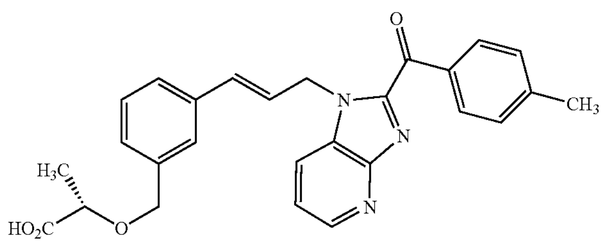 |
| 43 | 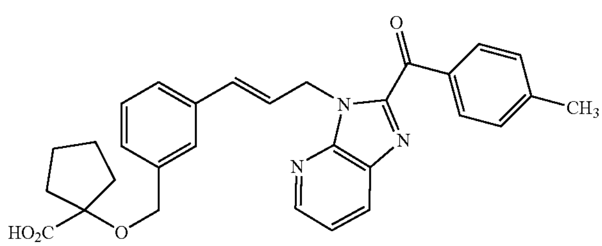 |
| 44 | 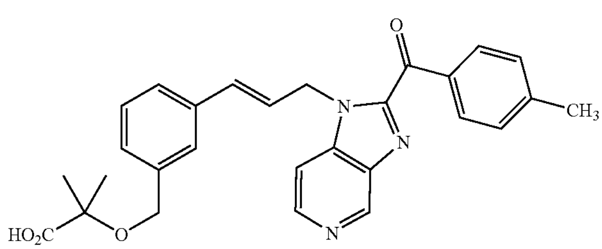 |
| 45 | 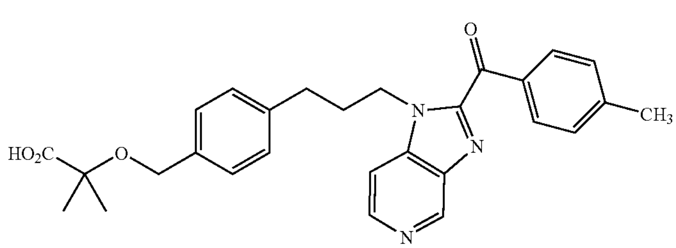 |

TABLE 4-continued
| Comp. No. | Structure |
|---|---|
| 46 | 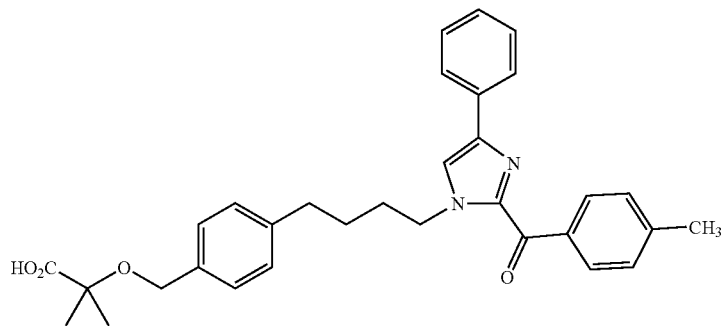 |
| 47 | 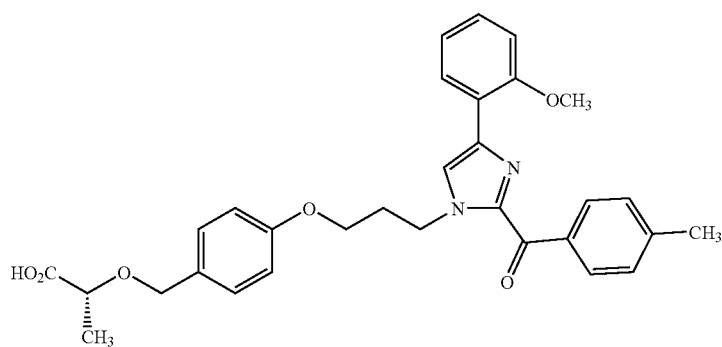 |
| 48 | 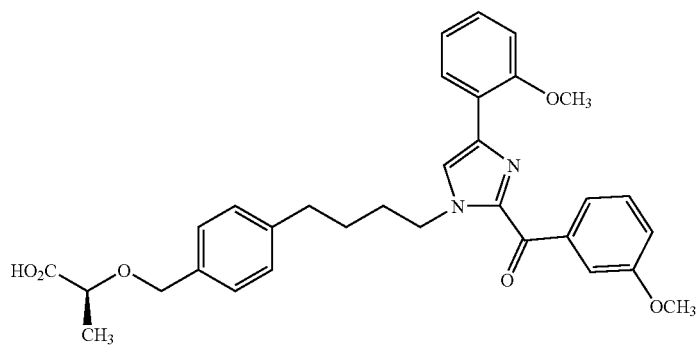 |
TABLE 5
| Comp. No. | Structure |
|---|---|
| 49 | 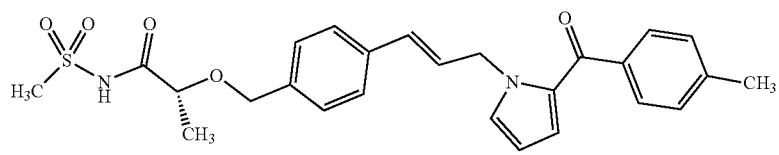 |
| 50 | 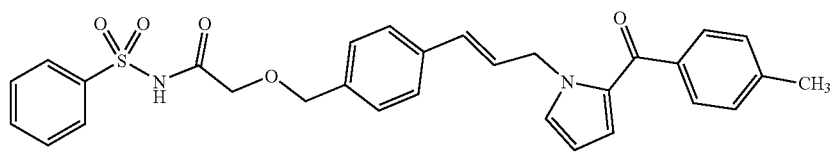 |

TABLE 5-continued
| Comp. No. | Structure |
| --- | --- |
| 51 | 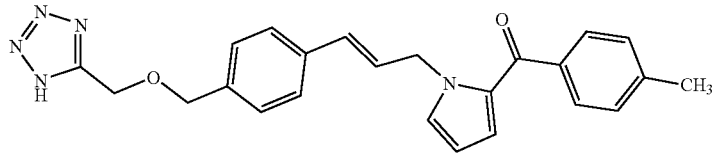 |
| 52 | 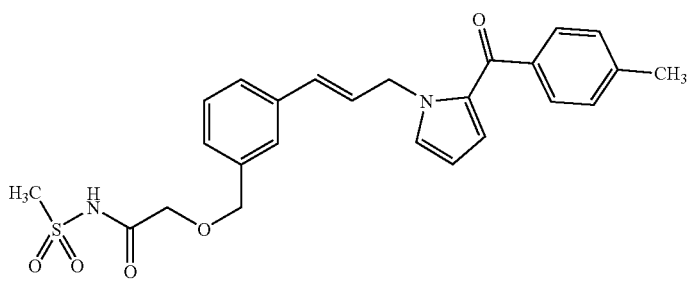 |
| 53 | 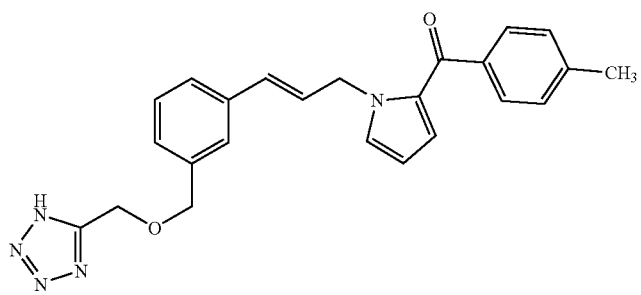 |
| 54 | 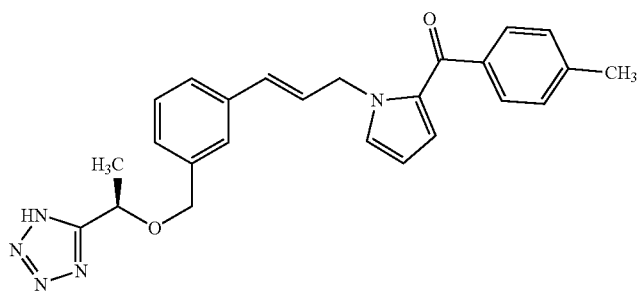 |
| 55 | 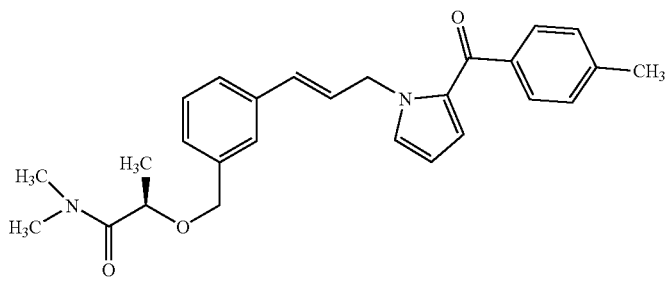 |

TABLE 5-continued
| Comp. No. | Structure |
|---|---|
| 56 | 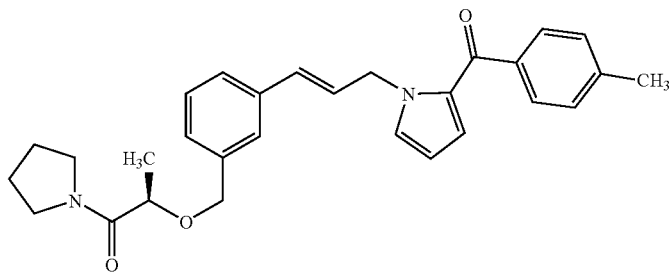 |
| 57 | 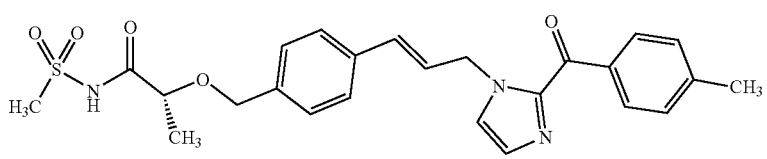 |
| 58 | 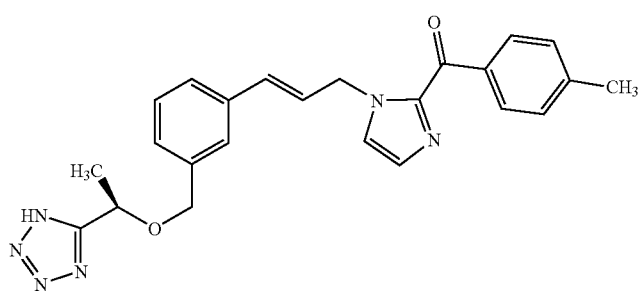 |
| 59 | 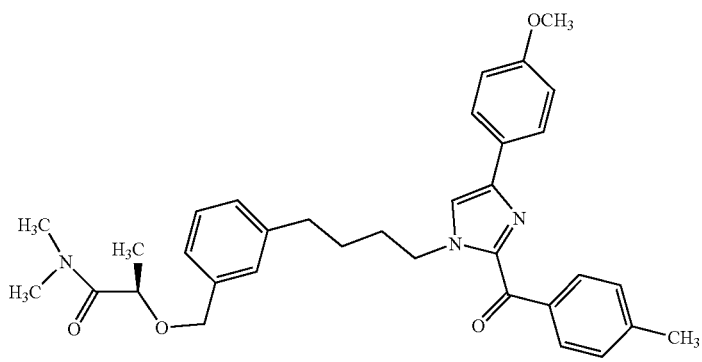 |
| 60 | 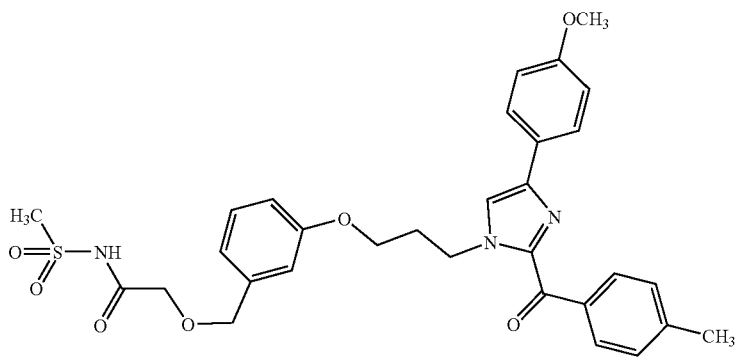 |

TABLE 6
| Comp. No. | Structure |
|---|---|
| 61 | 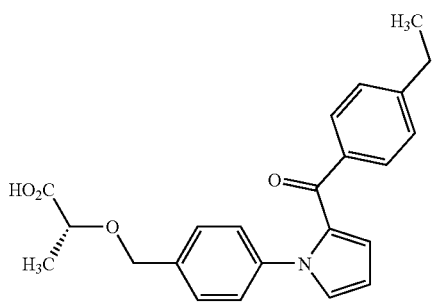 |
| 62 | 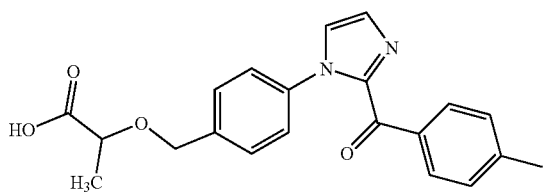 |
| 63 | 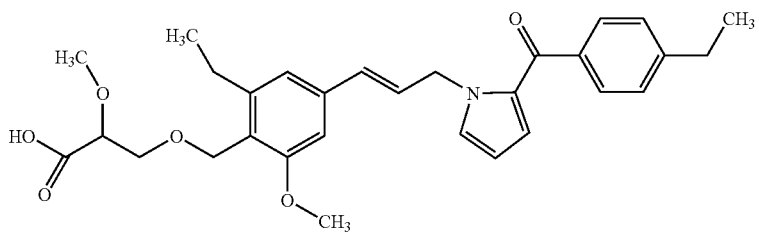 |
| 64 | 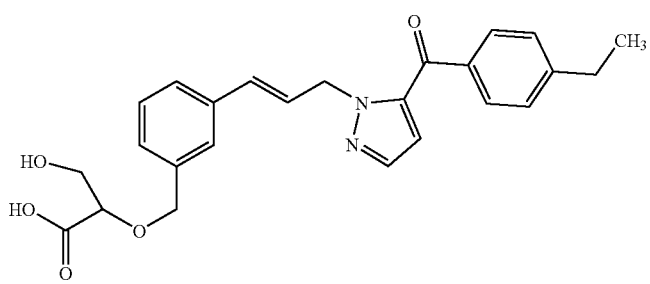 |
| 65 | 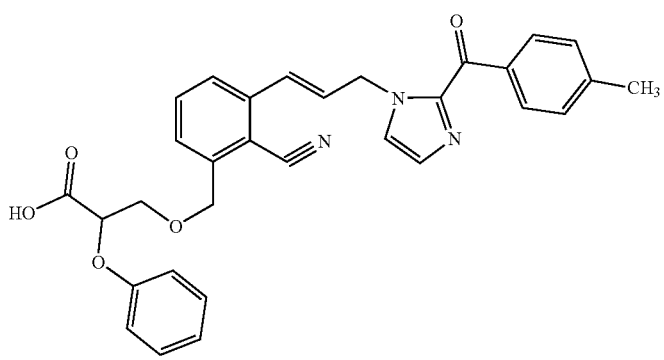 |

TABLE 6-continued
| Comp. No. | Structure |
|---|---|
| 66 | 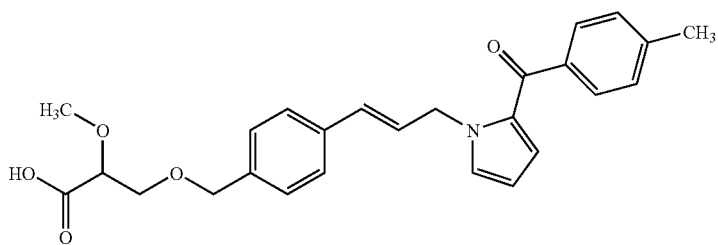 |
| 67 | 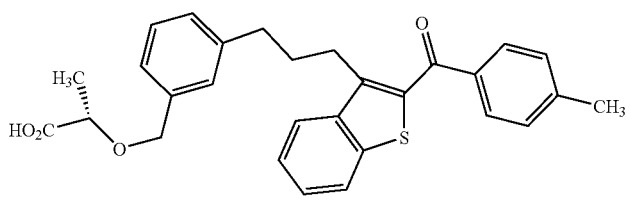 |
| 68 | 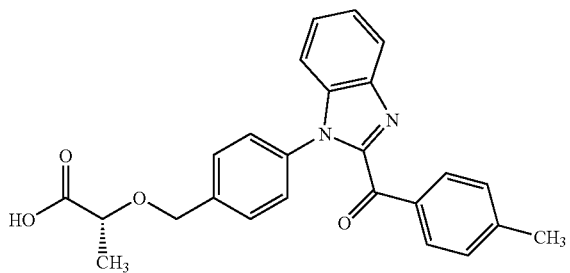 |
| 69 | 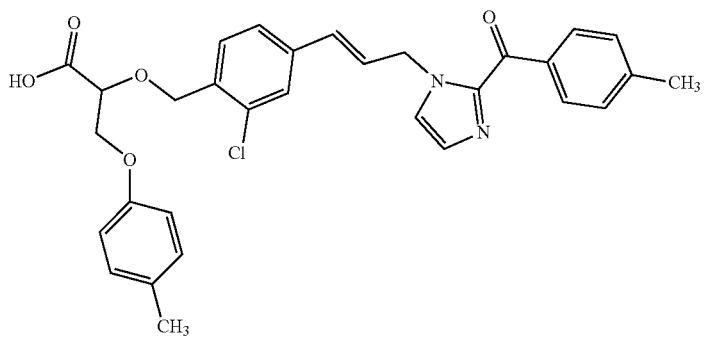 |
| 70 | 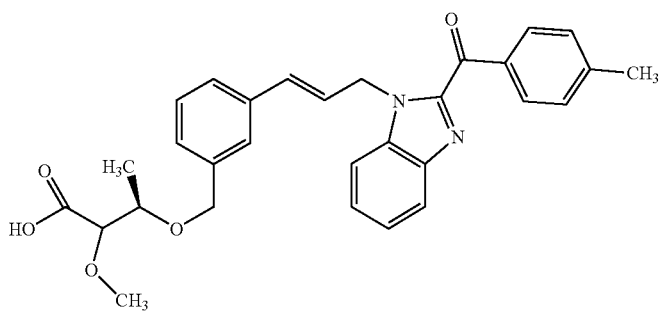 |

TABLE 6-continued

| Comp. No. | Structure |
|---|---|
| 71 | (structure) |
| 72 | (structure) |

EXAMPLES

The present invention is illustrated in more detail by Reference Examples and Examples, but the present invention should not be construed to be limited thereto. In addition, the nomenclature of compounds as indicated in the following Reference Examples and Examples was done according to ACD Labs 7.0 Name.

(Method A)

Conditions for LC-MS Analysis:
Machine body: ZQ 2000 (Waters Inc.), ionization method: ESI
Column: XTerra MS $C_{18}$ 2.5 μm (2.1×20 mm) (Waters Inc.)
Solution A: $H_2O$, Solution B: acetonitrile, Flow rate: 1 ml/min Conditions for Analysis:
0.0 min→0.5 min: Solution A 95% constant (Solution B 5%)
0.5 min→2.5 min: Solution A 95% →1% (Solution B 5%→99%)
2.5 min→3.5 min: Solution A 1% constant (Solution B 99%)

In the period from 0 min to 3.5 min, the analysis was carried out in the presence of 0.06% formic acid to the volume of Solution A +Solution B (=total volume)

(Method B)

Machine body: API 150EX (PE SCIEX Inc.), ionization method: ESI
Column: CombiScreen Hydrosphere C18 S-5 μm (4.6×50 mm) (YMC Inc.)

Solution A: 0.05% aqueous trifluoroacetic acid solution
Solution B: Acetonitrile containing 0.035% trifluoroacetic acid
Flow rate: 3.5 ml/min.

Conditions for Analysis:
0.0 min→0.5 min: Solution A 90% constant (Solution B 10%)
0.5 min→4.2 min: Solution A 90%→1% (Solution B 10%, 99%)
4.2 min→4.4 min: Solution A 1% constant (Solution B 99%)
R.T. =Retention Time Reference Example 1

(1-Allyl-1H-pyrrol-2-yl)(4-methylphenyl)methanone

Reference Example 1-1

(4-Methylphenyl)[1-(phenylsulfonyl)-1H-pyrrol-2-yl]methanone

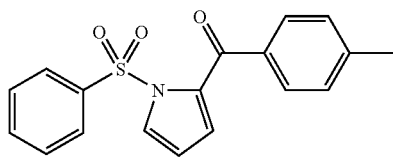

Under nitrogen atmosphere, to a solution of 1-benzene-sulfonyl-1H-pyrrole (284 g, 1.37 mol) in dichloromethane (1.0 L) were added p-toluoyl chloride (318 g, 2.06 mol) and boron trifluoride ether complex (350 g, 2.47 mol), and the mixture was allowed to stand at room temperature for 7 days. The reaction solution was washed successively with 1N aqueous hydrochloric acid solution (750 mL×2), 1N aqueous sodium hydroxide solution (750 mL) and saturated saline (100 mL), dried, and filtered. The filtrate was concentrated under atmospheric pressure until about 500 ml, and thereto was added hexane (500 mL). The reaction mixture was further concentrated until about 500 ml, cooled to 10° C., and the resulting crystals were collected by filtration. The obtained crystals were washed successively with hexane and toluene to give the title compound (315 g, 71%).

$^1$H NMR (CDCl$_3$, 300 MHz) δ 8.12 (d, 2H, J=8.3 Hz), 7.75-7.78 (m, 1H), 7.72 (brd, 2H, J=7.9 Hz), 7.65 (brt, 1H, J=7.9 Hz), 7.58 (brt, 2H, J=7.9 Hz), 7.25 (d, 2H, J=8.3 Hz), 6.69-6.72 (m, 1H), 6.35 (dd, 1H, J=3.1, 0.5 Hz), 2.42 (s, 3H).

Reference Example 1-2

(4-Methylphenyl)(1H-pyrrol-2-yl)methanone

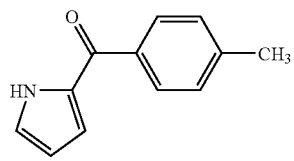

The compound of Reference Example 1-1 (145 g, 446 mmol) was suspended in methanol (1.0 L), and thereto was added a 5N aqueous sodium hydroxide solution (1.1 kg), and the mixture was refluxed for 30 minutes. This solution was cooled to 0° C., and the precipitated crystals were collected by filtration, and dried to give the title compound (80 g, 97%).

$^1$H NMR (CDCl$_3$, 300 MHz) δ 9.52 (brs, 1H), 8.25 (d, 2H, J=8.3 Hz), 7.29 (d, 2 H, J=8.3 Hz), 7.12 (brs, 1H), 6.88-6.91 (m, 1H), 6.32-6.36 (m, 1H), 2.44 (s, 3H).

Reference Example 1-3

(1-Allyl-1H-pyrrol-2-yl)(4-methylphenyl)methanone

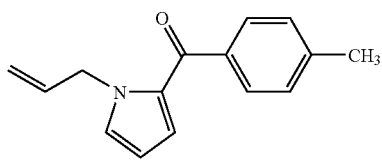

Potassium t-butoxide (1.05 g, 9.36 mmol) was dissolved in tetrahydrofuran (THF) (10 mL), and thereto was added the compound of Reference Example 1-2 (1.65 g, 8.91 mmol). The mixture was stirred at room temperature for 30 minutes, and thereto was added allyl bromide (1.62 g, 13.4 mmol). The mixture was stirred for 2 hours, and thereto was added water, and the mixture was extracted with ethyl acetate. The organic layer was concentrated, and the residue was purified by silica gel column chromatography to give the title compound (1.61 g, 80%).

$^1$H NMR (CDCl$_3$, 400 MHz) δ 7.71 (d, 2H, J=8.1 Hz), 7.25 (d, 2H, J=8.1 Hz), 6.98 (dd, 1H, J=1.6,2.5 Hz), 6.74 (dd, 1H, J=1.6, 4.0 Hz), 6.19 (dd, 1H, J=2.5, 4.0 Hz), 6.07 (ddt, 1H, J=10.3, 16.7, 5.6 Hz), 5.16 (dq, 1H, J=10.3, 1.3 Hz), 5.07 (dq, 1H, J=16.7, 1.3 Hz), 5.05 (dt, 2H, J=5.6, 1.3 Hz), 2.42 (brs, 3 H).

Reference Example 2

(1-Allyl-1H-pyrrol-2-yl)(4-methoxyphenyl)methanone

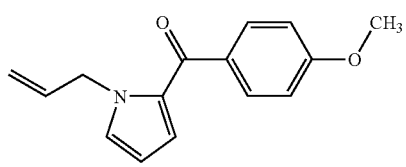

The title compound was synthesized in a similar manner to Reference Example 1.

LC-MS (Method B): R.T. 3.65 min., m/z 242 (M+1)

Reference Example 3

(1-Allyl-1H-pyrrol-2-yl)(4-ethylphenyl)methanone

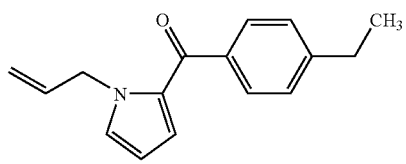

The title compound was synthesized in a similar manner to Reference Example 1.

LC-MS (Method B): R.T. 4.05 min., m/z 240 (M+1)

Reference Example 4

(1-Allyl-1H-pyrrol-2-yl)(3,5-dimethylphenyl)methanone

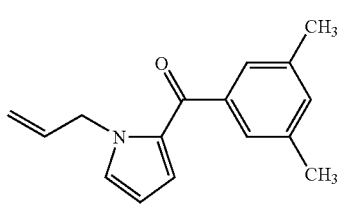

The title compound was synthesized in a similar manner to Reference Example 1.

LC-MS (Method A): R.T. 2.47 min., m/z 240 (M+1)

Reference Example 5

(1-Allyl-4-methyl-1H-pyrrol-2-yl)(4-methoxyphenyl)methanone

Reference Example 5-1

5-(4-Methoxybenzoyl)-1H-pyrrole-3-carbaldehyde

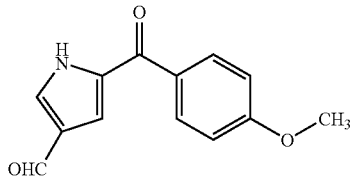

(4-Methoxyphenyl)(1H-pyrrol-2-yl)methanone (1.50 g, 7.45 mmol), which was synthesized in a similar manner to Reference Example 1-2, was dissolved in nitromethane (8.0 g) and ethylene chloride (8.0 g), and the mixture was cooled to 10° C., and thereto was added aluminum chloride (3.99 g, 29.8 mmol). To the mixture was added dropwise a solution of dichloromethyl methyl ether (1.88 g, 16.4 mmol) in ethylene chloride (3.0 g), and the mixture was stirred for one hour. To the mixture was added an aqueous hydrochloric acid solution, and the mixture was extracted with chloroform. The organic layer was treated with magnesium sulfate and activated carbon, filtered, and concentrated. The residue was washed with toluene to give the title compound (1.2 g, 70%).

$^1$H NMR (CDCl$_3$, 400 MHz) δ 10.20 (brs, 1H), 9.90 (s, 1H), 7.98 (d, 2H, J=8.9 Hz), 7.72 (dd, 1H, J=3.3, 1.4 Hz), 7.33 (dd, 1H, J=2.3, 1.4 Hz), 7.01 (d, 2H, J=8.9 Hz), 3.91 (s, 3H).

Reference Example 5-2

(4-Methoxyphenyl)(4-methyl-1H-pyrrol-2-yl)methanone

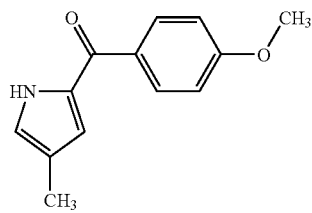

The compound of Reference Example 5-1 (230 mg, 1.00 mmol) was stirred with 10% palladium-carbon (230 mg) in THF (3.0 mL) under hydrogen atmosphere for 8 hours. The mixture was filtered, and the filtrate was concentrated. The residue was purified by silica gel column chromatography to give the title compound (130 mg, 60%).

$^1$H NMR (CDCl$_3$, 400 MHz) δ 9.38 (brs, 1H), 7.92 (d, 2H, J=8.9 Hz), 6.97 (d, 2H, J=8.9 Hz), 6.89-6.90 (m, 1H), 6.70 (dd, 1H, J=1.2, 2.0 Hz), 3.88 (s, 3H), 2.15 (s, 3H).

Reference Example 5-3

(1-Allyl-4-methyl-1H-pyrrol-2-yl)(4-methoxyphenyl)methanone

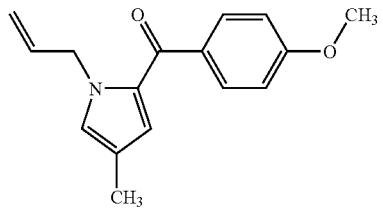

The title compound was synthesized in a similar manner to Reference Example 1-3.

LC-MS (Method A): R.T. 2.34 min., m/z 256 (M+1)

Reference Example 6

(1-Allyl-1H-pyrrol-3-yl)(4-methylphenyl)

Reference Example 6-1

(1-Benzenesulfonyl-1H-pyrrol-3-yl)(4-methylphenyl)ketone

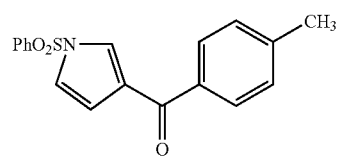

Under nitrogen atmosphere, to a suspension of aluminum chloride (4.62 g, 34.7 mmol) in ethylene chloride (50 mL) was added a solution of p-toluoyl chloride (4.91 g, 31.8 mmol) in ethylene chloride (5 mL) at room temperature over a period of 10 minutes. The mixture was stirred for 30 minutes, and thereto was added a solution of 1-benzenesulfonyl-1H-pyrrole (6.00 g, 28.9 mmol) in ethylene chloride (10 mL) over a period of 10 minutes. The mixture was stirred at room temperature for 2 hours. The reaction mixture was poured into ice-water, and the aqueous layer was extracted twice with dichloromethane. The organic layers were combined, dried, and filtered. The filtrate was concentrated, and the residue was purified by silica gel column chromatography to give the title compound (9.9 g, 100%).

$^1$H NMR (CDCl$_3$, 300 MHz) δ 7.89 (brd, 2H, J=7.9 Hz), 7.73 (d, 2H, J=8.0 Hz), 7.65 (brt, 1H, J=7.9 Hz), 7.65 (brs, 1H), 7.34 (brt, 2H, J=7.9 Hz), 7.29 (d, 2 H, J=8.0 Hz), 7.22 (dd, 1H, J=2.2, 2.8 Hz), 6.80 (dd, 1H, J=1.5, 2.8 Hz), 2.44 (s, 3H).

Example 6-2

(1H-Pyrrol-3-yl)(4-methylphenyl)ketone

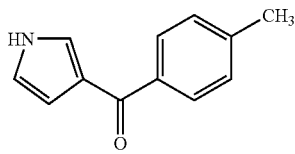

A mixture of the compound of Reference Example 6-1 (6.50 g, 20.0 mmol) and 5N aqueous sodium hydroxide solution (70 mL) and THF (70 mL) was stirred at 45° C. for 6 hours. The organic layer was separated, and the solvent was concentrated until 5 mL, and the mixture was allowed to stand at room temperature for 2 days. The precipitated crystals were collected by filtration, washed with cold THF to give the title compound (3.1 g, 84%).

$^1$H NMR (CDCl$_3$, 300 MHz) δ 7.76 (d, 2H, J=8.1 Hz), 7.35 (brquint., 1H, J=1.5 Hz), 7.26 (d, 2H, J=8.1 Hz), 6.84 (brq, 1H, J=1.5 Hz), 6.76 (brs, 1H), 2.43 (s, 3H).

Example 6-3

(1-Allyl-1H-pyrrol-3-yl)(4-methylphenyl)methanone

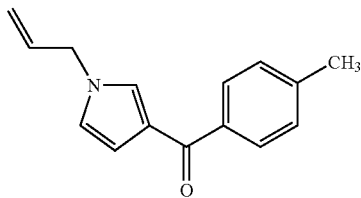

The title compound was obtained in a similar manner to Reference Example 1-3.

LC-MS (Method A): R.T. 2.34 min., m/z 226(M+1)

Reference Example 7

(1-Allyl-1H-imidazol-2-yl)[4-(trifluoromethyl)phenyl]methanone

Reference Example 7-1

N,N-Dimethyl-1H-imidazole-1-sulfonamide

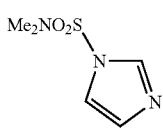

Imidazole (5.00 g, 73.6 mmol) was dissolved in toluene (80 ml), and thereto were added triethylamine (9.52 ml, 68.4 mmol) and dimethylsulfamoyl chloride (6.77 ml, 63.3 mmol), and the mixture was stirred at room temperature for 8 hours. The precipitates were removed by filtration, and the filtrate was concentrated under reduced pressure. The resulting residue was subjected to azeotropic distillation with hexane to give the title compound (10.9 g, 98%).

$^1$H NMR (CDCl$_3$, 400 MHz) δ 7.87 (s, 1H), 7.23 (d, 1H, J=1.4 Hz), 7.11 (d, 1H, J=1.4 Hz), 2.82 (s, 6H).

Reference Example 7-2

1H-Imidazol-2-yl[4-(trifluoromethyl)phenyl]methanone

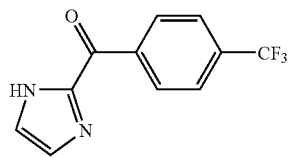

The compound of Reference Example 7-1 (1.00 g, 5.71 mmol) was dissolved in THF (30 ml), and the mixture was stirred at −78° C. To this solution was added n-butyl lithium (1.57 M hexane solution, 3.9 ml, 6.3 mmol), and the mixture was stirred at −78° C. for 30 minutes. Then, thereto was added a solution of 4-(trifluoromethyl)benzaldehyde (1.49 g, 8.57 mmol) in THF (5 ml), and the mixture was warmed to room temperature and stirred overnight. To the reaction solution were added a 2.5N diluted hydrochloric acid and a mixture of hexane and ethyl acetate (3:1), and the aqueous layer was separated. The aqueous layer was basified with a 4N aqueous sodium hydroxide solution, and the mixture was extracted with ethyl acetate. The organic layer was washed with water and saturated saline, and dried over anhydrous magnesium sulfate. The solvent was concentrated under reduced pressure, and the resulting residue was dissolved in chloroform (150 ml). Manganese dioxide (20.0 g, 23.0 mmol) was added to the mixture, and the mixture was stirred at 70° C. for 2 hours. The reaction mixture was filtered through Celite, and the solvent in the filtrate was evaporated under reduced pressure. The resulting residue was dissolved in THF (20 ml), and thereto was added a 4N diluted hydrochloric acid (50 ml), and the mixture was refluxed for 4 hours. The mixture was neutralized by adding dropwise a 4N aqueous sodium hydroxide solution under ice-cooling with stirred, and the mixture was extracted with ethyl acetate. The organic layer was washed with water and saturated saline, and dried over anhydrous magnesium sulfate. The solvent was concentrated under reduced pressure, and the resulting residue was purified by silica gel column chromatography to give the title compound (320 mg, 23%).

$^1$H NMR (CDCl$_3$, 400 MHz) δ 10.61 (brs, 1H), 8.69 (d, 2H, J=8.2 Hz), 7.78 (d, 2H, J=8.2 Hz), 7.42 (d, 1H, J=0.9 Hz), 7.34 (d, 1H, J=0.9 Hz).

Reference Example 7-3

(1-Allyl-1H-imidazol-2-yl)[4-(trifluoromethyl)phenyl]methanone

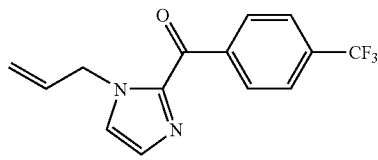

The compound of Reference Example 7-2 (320 mg, 1.33 mmol) was dissolved in THF (5 ml), and thereto was added potassium t-butoxide (164 mg, 1.46 mmol). The mixture was stirred at room temperature for 30 minutes, and thereto was added allyl bromide (213 mg, 2.00 mmol). The mixture was stirred at 40° C. for 4 hours, and to the reaction solution was added water, and the mixture was extracted with ethyl acetate. The organic layer was washed with water and saturated saline, and dried over anhydrous magnesium sulfate. The solvent was evaporated under reduced pressure, and the resultant was subjected to azeotropic distillation with hexane to give the title compound (368 mg, 99%).

$^1$H NMR (CDCl$_3$, 400 MHz) δ 8.34 (d, 2H, J=8.2 Hz), 7.74 (d, 2H, J=8.2 Hz), 7.28 (d, 1H, J=0.8 Hz), 7.22 (d, 1H, J=0.8 Hz), 6.08 (ddt, 1H, J=10.3, 17.0, 5.8 Hz), 5.28 (d, 1H, J=10.3 Hz), 5.16 (d, 1H, J=17.0 Hz), 5.13 (d, 2H, J=5.8 Hz).

Reference Example 8

(1-Allyl-1H-imidazol-2-yl)[4-(methyl)phenyl]methanone

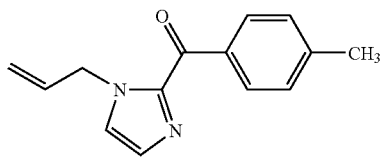

The title compound was obtained in a similar manner to Reference Example 7.

LC-MS (Method B): R.T. 3.42 min., m/z 227 (M+1)

Reference Example 9

(1-Allyl-1H-imidazol-2-yl)[4-(methoxy)phenyl]methanone

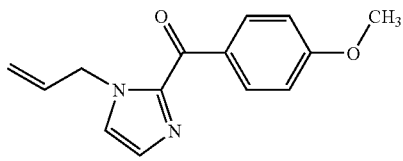

The title compound was obtained in a similar manner to Reference Example 7.

LC-MS (Method B): R.T. 3.42 min., m/z 227 (M+1)

Reference Example 10

(1-Allyl-1H-1,2,4-triazol-5-yl)[4-(trifluoromethyl)phenyl]methanone

Reference Example 10-1

N,N-Dimethyl-1H-1,2,4-triazole-1-sulfonamide

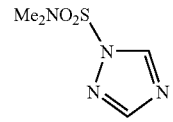

Triazole (5.08 g, 73.6 mmol) was dissolved in toluene (80 ml), and thereto were added triethylamine (9.52 ml, 68.4 mmol) and dimethylsulfamoyl chloride (10.6 ml, 73.6 mmol), and the mixture was stirred at 50° C. for 2 hours. The precipitates were removed by filtration, and the filtrate was concentrated under reduced pressure. The resulting residue was purified by silica gel column chromatography to give the title compound (4.52 g, 38%).

$^1$H NMR (CDCl$_3$, 400 MHz) δ 8.58 (s, 1H), 8.06 (s, 1H), 2.99 (s, 6H).

Reference Example 10-2

1H-1,2,4-Triazol-5-yl[4-(trifluoromethyl)phenyl]methanone

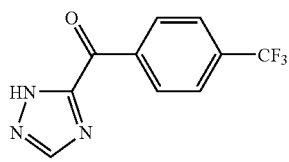

The compound of Reference Example 10-1 (2.00 g, 11.4 mmol) was dissolved in THF (60 ml), and the mixture was stirred at −78° C. To this solution was added n-butyl lithium (1.57 M hexane solution, 8.0 ml, 13 mmol), and the mixture was stirred at −78° C. for 1 hour. Then, thereto was added a solution of 4-(trifluoromethyl)benzaldehyde (2.98 g, 17.1 mmol) in THF (20 ml), and the mixture was warmed to room temperature and stirred overnight. To the reaction solution was added an aqueous ammonium chloride solution, and the mixture was extracted with ethyl acetate. The organic layer was washed with water and saturated saline, and dried over anhydrous magnesium sulfate. The solvent was evaporated under reduced pressure, and the resulting residue was dissolved in chloroform (150 ml), and further thereto was added manganese dioxide (12.0 g, 13.8 mmol). The mixture was stirred at 70° C. for 2 hours, and filtered through Celite. The solvent in the filtrate was evaporated under reduced pressure. The resulting residue was dissolved in THF (40 ml), and thereto was added a 4N diluted hydrochloric acid (100 ml), and the mixture was refluxed for 4 hours. The mixture was neutralized by adding dropwise a 4N aqueous sodium hydroxide solution under ice-cooling with stirring, and the mixture was extracted with ethyl acetate. The organic layer was washed with water and saturated saline, and dried over anhydrous magnesium sulfate. The solvent was evaporated under reduced pressure, and the resulting residue was recrystallized from ethyl acetate to give the title compound (1.54 g, 56%).

$^1$H NMR (DMSO-d$_6$, 400 MHz) δ 14.96 (brs, 1H), 8.80 (s, 1H), 8.43 (d, 2H, J=8.3 Hz), 7.96 (d, 2H, J=8.3 Hz).

Reference Example 10-3

(1-Allyl-1H-1,2,4-triazol-5-yl)[4-(trifluoromethyl)phenyl]methanone

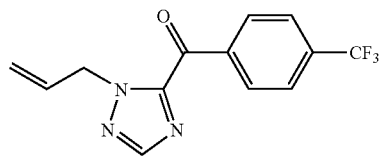

The compound of Reference Example 10-2 (241 mg, 1.00 mmol) was dissolved in DMF (3 ml), and the mixture was stirred under ice-cooling. To the mixture was added sodium hydroxide (60% in parafin liquid) (44.0 mg, 1.10 mmol), and the mixture was stirred at 50° C. for one hour. Then, to the reaction solution was added a solution of allyl bromide (107 mg, 1.00 mmol) in DMF (1 ml) at 50° C. The mixture was stirred at 50° C. for 2 hours, and cooled to room temperature, and thereto was added water, and the mixture was extracted with ethyl acetate. The organic layer was washed with water and saturated saline, and dried over anhydrous magnesium sulfate. The solvent was evaporated under reduced pressure, and the resulting residue was purified by silica gel column chromatography to give the title compound (41.8 mg, 15%).

$^1$H NMR (CDCl$_3$, 400 MHz) δ 8.47 (d, 2 H, J=8.2 Hz), 8.07 (s, 1H), 7.78 (d, 2 H, J=8.2 Hz), 6.07 (ddt, 1H, J=10.3, 17.0, 5.8 Hz), 5.28 (d, 1H, J=10.3 Hz), 5.26 (d, 2 H, J=5.8 Hz), 5.24 (d, 1H, J=17.0 Hz).

Reference Example 10-4

(1-Allyl-1H-1,2,4-triazol-3-yl)[4-(trifluoromethyl)phenyl]methanone

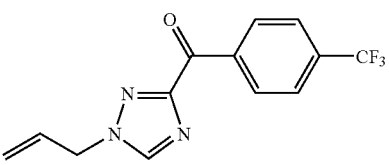

When the compound of Reference Example 10-3 was purified by silica gel column chromatography, the compound of Reference Example 10-4 was also obtained.

LC-MS (Method B): R.T. 3.90 min., m/z 282 (M+1)

Reference Example 11

(1-allyl-1H-pyrazol-5-yl)(4-propylphenyl)methanone

Reference Example 11-1

1-Allyl-1H-pyrazole-5-carbaldehyde

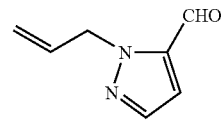

Pyrazole-3-carbaldehyde (3.00 g, 31.2 mmol) was dissolved in DMF (20 ml), and thereto were added potassium carbonate (6.47 g, 46.8 mmol) and allyl bromide (3.50 g, 32.8 mmol) with stirring. The mixture was stirred at room temperature for 6 hours, and thereto was added water, and the mixture was extracted with ethyl acetate. The organic layer was washed with water and saturated saline, and dried over anhydrous magnesium sulfate. The solvent was evaporated under reduced pressure, and the resulting residue was purified by silica gel column chromatography to give the title compound (429 mg, 10%).

$^1$H NMR (CDCl$_3$, 400 MHz) δ 9.86 (s, 1H), 7.59 (d, 1H, J=2.0 Hz), 6.93 (d, 1H, J=2.0 Hz), 6.04-5.94 (ddt, 1H, J=10.3, 17.1, 5.7 Hz), 5.19 (dd, 1H, J=1.2, 10.3 Hz), 5.16 (d, 2H, J=5.7 Hz), 5.09 (dd, 1H, J=1.2, 17.1 Hz).

Reference Example 11-2

(1-Allyl-1H-pyrazol-5-yl)(4-propylphenyl)methanone

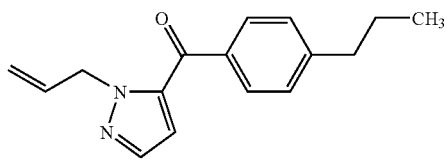

To magnesium powder (26.7 mg, 1.10 mmol) was added dropwise 1-n-propyl-4-bromobenzene (220 mg, 1.10 mmol) at room temperature. The reaction solution was further stirred at 50° C. for one hour, and cooled to −78° C. To the mixture was added a solution of the compound of Reference Example 11-1 (75.0 mg, 0.551 mmol) in THF (1 ml), and the mixture was stirred at room temperature for 2 hours. To the mixture was added a saturated aqueous ammonium chloride solution, and the mixture was extracted with ethyl acetate. The organic layer was washed with water and a saturated saline, and dried over anhydrous magnesium sulfate. The solvent was evaporated under reduced pressure, and the resulting residue was dissolved in chloroform (50 ml), and thereto was added manganese dioxide (5.00 g, 5.75 mmol). The mixture was stirred at 60° C. for 3 hours, and cooled to room temperature. The mixture was filtered through Celite, and the solvent in the filtrate was evaporated under reduced pressure. The resulting residue was purified by silica gel column chromatography to give the title compound (64.0 mg, 46%).

$^1$H NMR (CDCl$_3$, 400 MHz) δ 7.81 (d, 2H, J=8.2 Hz), 7.56 (d, 1H, J=2.0 Hz), 7.29 (d, 2H, J=8.2 Hz), 6.67 (d, 1H, J=2.0 Hz), 6.06 (ddt, 1H, J=10.3, 17.1, 5.7 Hz), 5.19 (d, 1H, J=10.3 Hz), 5.17 (d, 2H, J 5.7 Hz), 5.13 (d, 1H, J=17.1 Hz), 2.67 (t, 2H, J=7.4 Hz), 1.69 (tq, 2H, J=7.4, 7.3 Hz), 0.96 (t, 3H, J=7.3 Hz).

Reference Example 12

(2S)-2-(3-{4-[2-(3-Methoxybenzoyl)-4-phenyl-1H-imidazol-1-yl]butyl}phenoxy)propanoic acid

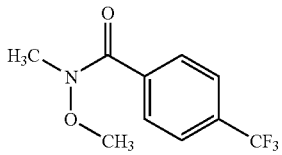

4-(Trifluoromethyl)benzoic acid (20.0 g, 105 mmol) was dissolved in DMF (200 ml), and thereto were added successively N,O-dimethylhydroxylamine hydrochloride (12.3 g, 126 mmol), 1-ethyl-3-(3-dimethylaminopropyl)-carbodiimide hydrochloride (WSC) (24.2 g, 126 mmol), 1-hydroxybenzotriazole (HOBt) (17.1 g, 126 mmol), and triethylamine (11.9 g, 117 mmol) at 0° C. with stirring. The mixture was stirred at room temperature for 2 hours, and water was added thereto. The mixture was extracted with ethyl acetate, and the solvent was evaporated under reduced pressure, and the resulting residue was subjected to azeotropic distillation with toluene to give the title compound (25.3 g, quant.).

$^1$H NMR (CDCl$_3$, 400 MHz) δ 7.79 (d, 2H, J=8.1 Hz), 7.67 (d, 2H, J=8.1 Hz), 3.53 (s, 3H), 3.38 (s, 3H).

Reference Example 13

N,3-Dimethoxy-N-methylbenzamide

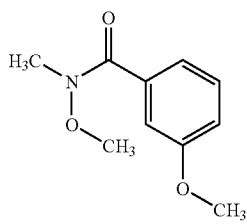

The compound of Reference Example 13 was synthesized in a similar manner to Reference Example 12.

LC-MS (Method A): R.T. 1.83 min., m/z 196 (M+1)

Reference Example 14

N-Methoxy-N-methyl-6-(trifluoromethyl)nicotinamide

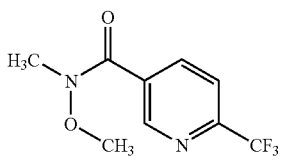

The compound of Reference Example 14 was synthesized in a similar manner to Reference Example 12.

LC-MS (Method A): R.T. 1.91 min., m/z 235 (M+1)

Reference Example 15

(3-Methoxyphenyl)[4-(4-methoxyphenyl)-1H-imidazol-2-yl]methanone

Reference Example 15-1

4-(4-Methoxyphenyl)-1H-imidazole

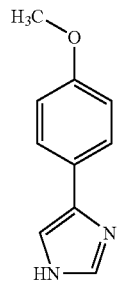

4-Methoxyphenacyl bromide (2.29 g, 10.0 mmol) was dissolved in formamide (45.0 g, 1.00 mol), and the mixture was stirred at 170° C. for 6 hours. The reaction solution was cooled to room temperature, and thereto was added water. The mixture was extracted with ethyl acetate, and the organic layer was washed successively with water and saturated saline, and dried over anhydrous magnesium sulfate. The solvent was evaporated under reduced pressure, and thereto was added a mixture of hexane and ethyl acetate (5:1) (200 ml). The resulting suspension was stirred at 50° C. for 2 hours, and further stirred at room temperature for 5 hours. The precipitated crystals were collected by filtration, and washed with hexane to give the title compound (1.52 g, 87%).

$^1$H NMR (CDCl$_3$, 400 MHz) δ 8.05 (brs, 1H), 7.68 (d, 1H, J=1.1 Hz), 7.63 (d, 2H, J=8.9 Hz), 7.23 (d, 1H, J=1.1 Hz), 6.91 (d, 2H, J=8.9 Hz), 3.81 (s, 3H).

Reference Example 15-2

4-(4-Methoxyphenyl)-N,N-dimethyl-1H-imidazole-1-sulfonamide

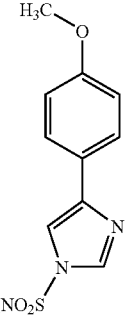

The compound of Reference Example 15-1 (1.02 g, 5.86 mmol) was dissolved in acetonitrile (100 ml), and thereto were added successively potassium carbonate (1.21 g, 8.78 mmol) and dimethylsulfamoyl chloride (1.01 g, 7.03 mmol), and the mixture was stirred at 70° for 7 hours. The reaction solution was cooled to room temperature, and thereto was added water. The mixture was extracted with ethyl acetate, and the organic layer was washed with water and saturated saline, and dried over anhydrous magnesium sulfate. The solvent was evaporated under reduced pressure, and the resulting residue was subjected to azeotropic distillation with toluene three times to give the title compound (1.60 g, 97%).

$^1$H NMR (CDCl$_3$, 400 MHz) δ 7.95 (d, 1H, J=1.2 Hz), 7.72 (d, 2 H, J=8.9 Hz), 7.40 (d, 1H, J=1.2 Hz), 6.95 (d, 2 H, J=8.9 Hz), 3.84 (s, 3 H), 2.90 (s, 6 H).

Reference Example 15-3

2-(3-Methoxybenzoyl)-4-(4-methoxyphenyl)-N,N-dimethyl-1H-imidazole-1-sulfonamide

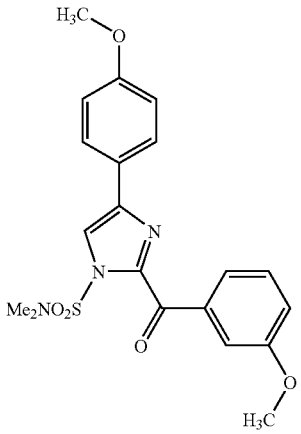

The compound of Reference Example 15-2 (1.60 g, 5.69 mmol) was dissolved in THF (50 ml), and the mixture was stirred at −78° C. To this solution was added n-butyl lithium (1.58 M hexane solution, 4.7 ml, 7.4 mmol), and the mixture was stirred at −78° C. for 30 minutes. Then, thereto was added a solution of the compound of Reference Example 13 in THF (5 ml), and the mixture was warmed to room temperature and stirred overnight. To the reaction solution was added a 2N aqueous ammonium chloride solution, and the mixture was extracted with ethyl acetate. The organic layer was washed with water and saturated saline, and dried over anhydrous magnesium sulfate. The solvent was evaporated under reduced pressure, and the resulting residue was purified by silica gel column chromatography to give the title compound (1.12 g, 48%).

$^1$H NMR (CDCl$_3$, 400 MHz) δ 7.75 (d, 2H, J=8.8 Hz), 7.72 (d, 1H, J=8.0 Hz), 7.69 (s, 1H), 7.40 (dd, 1H, J=8.0, 8.2 Hz), 7.18 (d, 1H, J=8.2 Hz), 6.94 (d, 2H, J=8.8 Hz), 3.87 (s, 3H), 3.84 (s, 3H), 3.13 (s, 6H).

Reference Example 15-4

(3-Methoxyphenyl)[4-(4-methoxyphenyl)-1H-imidazol-2-yl]methanone

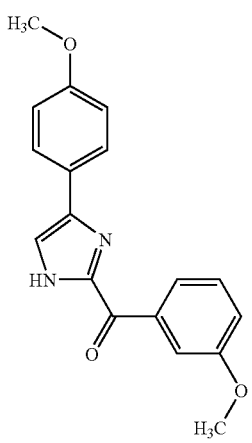

The compound of Reference Example 15-3 (1.12 g, 2.70 mmol) was suspended in ethanol (100 ml), and thereto was added a 4N diluted hydrochloric acid (100 ml), and the mixture was stirred at 70° C. for 3 hours. The solvent was almost evaporated under reduced pressure, and to the residue was added a 2N aqueous sodium hydroxide solution to adjust the pH value of the solution to about pH 4. The precipitated crystals were collected by filtration, and washed with water to give the title compound (832 mg, quant.).

$^1$H NMR (DMSO-d$_6$, 400 MHz) δ 8.11 (d, 1H, J=7.5 Hz), 8.10 (s, 1H), 7.92 (s, 1H), 7.86 (d, 2H, J=8.8 Hz), 7.51 (dd, 1H, J=7.5, 8.2 Hz), 7.26 (d, 1H, J=Hz), 7.01 (d, 2H, J=8.8 Hz), 3.86 (s, 3H), 3.79 (s, 3H).

Reference Example 16

(2-Methoxyphenyl)(4-phenyl-1H-imidazol-2-yl)methanone

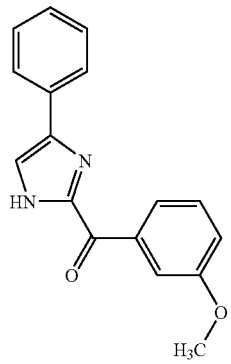

The compound of Reference Example 16 was synthesized in a similar manner to Reference Example 15.

LC-MS (Method A): R.T. 2.37 min., m/z 279 (M+1)

Reference Example 17

(4-Phenyl-1H-imidazol-2-yl)[4-(trifluoromethyl)phenyl]methanone

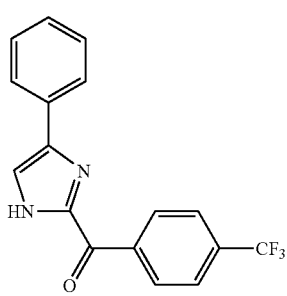

The compound of Reference Example 17 was synthesized in a similar manner to Reference Example 15.

LC-MS (Method A): R.T. 2.59 min., m/z 317 (M+1)

Reference Example 18

(3-Methoxyphenyl)[4-(2-methoxyphenyl)-1H-imidazol-2-yl]methanone

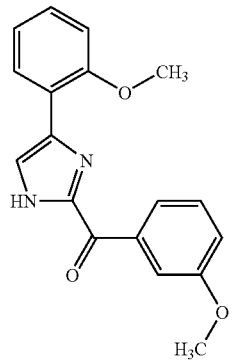

The compound of Reference Example 18 was synthesized in a similar manner to Reference Example 15.
LC-MS (Method A): R.T. 2.42 min., m/z 309 (M+1)

Reference Example 19

(4-Phenyl-1H-imidazol-2-yl)[6-(trifluoromethyl)pyridin-3-yl]methanone

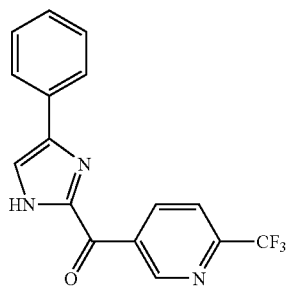

The compound of Reference Example 19 was synthesized in a similar manner to Reference Example 15.
LC-MS (Method A): R.T. 2.45 min., m/z 318 (M+1)

Reference Example 20

(1-But-3-en-1-yl-4-phenyl-1H-imidazol-2-yl)(3-methoxyphenyl)methanone

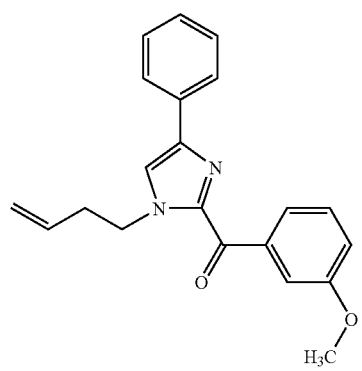

(3-Methoxyphenyl)(4-phenyl-1H-imidazol-2-yl)methanone (278 mg, 1.00 mmol) was dissolved in DMF (3 ml), and thereto were added potassium carbonate (207 mg, 1.50 mmol), 18-crown-6 (26.4 mg, 0.100 mmol), 3-butenyl bromide (162 mg, 1.20 mmol), and the mixture was stirred at 80° C. for 5 hours. The reaction solution was cooled to room temperature, and thereto was added water. The mixture was extracted with ethyl acetate, and the solvent was evaporated under reduced pressure. The resulting residue was subjected to azeotropic distillation with toluene to give the title compound (309 mg, 93%).

$^1$H NMR (CDCl$_3$, 400 MHz) δ 8.07 (d, 1H, J=7.7 Hz), 8.00 (s, 1H), 7.83 (d, 2H, J=8.0 Hz), 7.44 (s, 1H), 7.42 (dd, 1H, J=7.7, 8.2 Hz), 7.40 (dd, 1H, J=7.4, 8.0 Hz), 7.29 (t, 1H, J=7.4 Hz), 7.16 (d, 1H, J=8.2 Hz), 5.88-5.78 (m, 1H), 5.12-5.07 (m, 1H), 4.55 (t, 2H, J=7.1 Hz), 3.90 (s, 3H), 2.66 (dt, 2H, J=7.0, 7.1 Hz).

Reference Example 21

(1-But-3-en-1-yl-4-phenyl-1H-imidazol-2-yl)[4-(trifluoromethyl)phenyl]-methanone

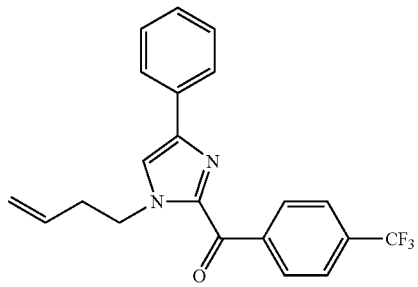

The compound of Reference Example 21 was synthesized in a similar manner to Reference Example 20.
LC-MS (Method A): R.T. 2.82 min., m/z 371 (M+1)

Reference Example 22

(1-But-3-en-1-yl-4-phenyl-1H-imidazol-2-yl)[6-(trifluoromethyl)pyridin-3-yl]-methanone

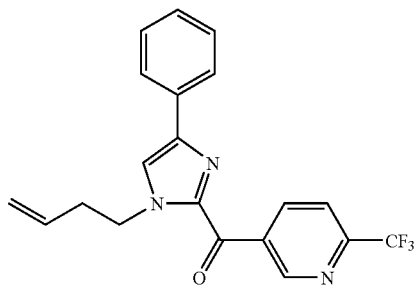

The compound of Reference Example 22 was synthesized in a similar manner to Reference Example 20.
LC-MS (Method A): R.T. 2.67 min., m/z 372 (M+1)

Reference Example 23

(1-Allyl-4-phenyl-1H-imidazole-2-yl)(4-methylphenyl)methanone

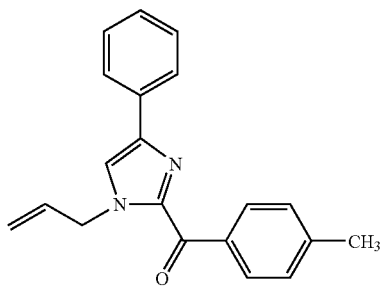

Potassium t-butoxide (2.59 g, 23.1 mmol) was dissolved in DMF (100 ml), and thereto was added 4-phenyl-1H-imidazole (3.00 g, 21 mmol) with stirring. The mixture was stirred at room temperature for 30 minutes, and thereto was added allyl bromide (3.50 g, 31.5 mmol). The mixture was stirred at 40° C. for 4 hours. To the reaction solution was added water, and the mixture was extracted with ethyl acetate. The organic layer was washed with water and saturated saline, dried over anhydrous magnesium sulfate, and the solvent was removed under reduced pressure. The resulting residue was dissolved in pyridine (24 ml), and thereto were added successively triethylamine (17.9 g, 17.7 mmol) and 4-toluoyl chloride (3.7 g, 16.3 mmol), and the mixture was stirred at 60° C. for 5 hours. To the reaction solution was added water (50 ml), and the mixture was extracted with ethyl acetate. The organic layer was washed with water, 1N diluted hydrochloric acid, and saturated saline, and dried over magnesium sulfate. Then, the solvent was evaporated under reduced pressure, and the resulting residue was purified by silica gel column chromatography to give the title compound (760 mg, 30%).

LC-MS (Method A): R.T. 2.51 min., m/z 303(M+1)

Reference Example 24

(1-But-3-en-1-yl-1H-benzimidazol-2-yl)(3-methoxyphenoxy)methanone

Reference Example 24-1

1H-Benzimidazol-2-yl(3-methoxyphenoxy)methanone

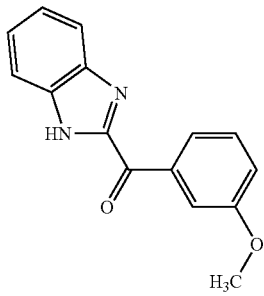

Benzimidazole (3.54 g, 30.0 mmol) was dissolved in pyridine (10 ml), and thereto was added triethylamine (13.3 g, 132 mmol), and the mixture was stirred at room temperature. To the reaction solution was added dropwise manisoyl chloride (15.3 g, 90.0 mmol) over a period of 30 minutes. The mixture was stirred at room temperature for one hour. Then, the reaction mixture was warmed to 50° C., and stirred for 2 hours. Further, to the reaction solution was added a 4N aqueous sodium hydroxide solution (150 ml), and the mixture was stirred at 60° C. for 3 hours. The reaction solution was allowed to cool to room temperature, and water was added thereto, and the mixture was extracted with ethyl acetate. The organic layer was washed successively with water, 1N diluted hydrochloric acid and saturated saline, and dried over magnesium sulfate. Magnesium sulfate was removed by filtration, and the solvent was evaporated under reduced pressure, and the residue was purified by silica gel column chromatography. In addition, the resultant was recrystallized from ethyl acetate to give the title compound (4.60 g, 61%).

$^1$H NMR (CDCl$_3$, 400 MHz) δ 8.39 (d, 1H, J=8.1 Hz), 8.14 (s, 1H), 7.79 (brd, 2 H), 7.48 (dd, 1H, J=8.1, 8.2 Hz), 7.43-7.41 (m, 2 H), 7.21 (d, 1H, J=8.2 Hz), 3.91 (s, 3 H).

Reference Example 24-2

(1-But-3-en-1-yl-1H-benzimidazol-2-yl)(3-methoxyphenoxy)methanone

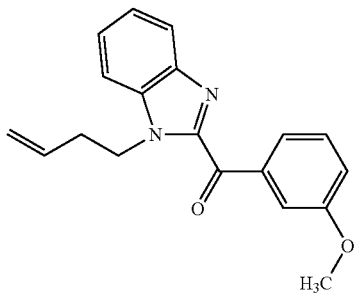

The compound of Reference Example 24-1 (2.52 g, 10.0 mmol) was dissolved in DMF (20 ml), and thereto were added successively potassium carbonate (2.07 g, 15.0 mmol), 18-crown-6-ether (396 mg, 1.50 mmol), 1-bromo-3-butene (2.03 g, 15.0 mmol), and the mixture was stirred at 80° C. for 4 hours. The reaction solution was allowed to cool to room temperature, and thereto was added water, and the mixture was extracted with ethyl acetate. The organic layer was washed successively with water and saturated saline, and dried over magnesium sulfate. Magnesium sulfate was removed by filtration, and the solvent was evaporated under reduced pressure. Further, the resultant was purified by silica gel column chromatography to give the title compound (3.01 g, 98%).

$^1$H NMR (CDCl$_3$, 400 MHz) δ 7.93 (d, 1H, J=8.1 Hz), 7.92-7.90 (m, 1H), 7.79 (s, 1H), 7.48 (dd, 1H, J=8.1, 8.2 Hz), 7.46-7.38 (m, 3H), 7.18 (d, 1H, J=8.2 Hz), 5.82 (ddt, 1H, J=5.1, 15.2, 7.1 Hz), 5.02 (d, 1H, J=15.2 Hz), 5.01 (d, 1H, J=5.1 Hz), 4.67 (t, 2H, J=7.4 Hz), 3.89 (s, 3H), 2.66 (dt, 2H, J=7.1, 7.4 Hz).

Reference Example 25

(1-Allyl-1H-benzimidazol-2-yl)(4-methylphenyl)methanone

Reference Example 25-1

1H-Benzimidazol-2-yl(4-methylphenoxy)methanone

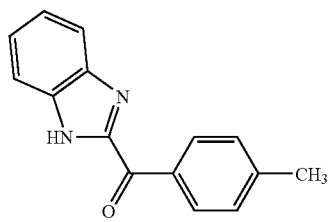

The title compound was synthesized in a similar manner to Reference Example 24-1.
LC-MS (Method B): R.T. 3.38 min., m/z 237 (M+1)

Reference Example 25-2

(1-Allyl-1H-benzimidazol-2-yl)(4-methylphenyl)methanone

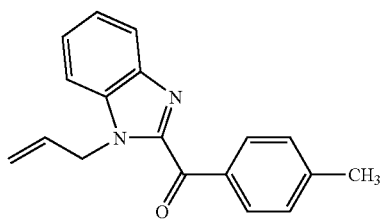

The title compound was synthesized in a similar manner to Reference Example 24-2.
LC-MS (Method B): R.T. 4.38 min., m/z 277 (M+1)

Reference Example 26

(4-Methylphenyl)(1-vinyl-1H-benzimidazol-2-yl)methanone

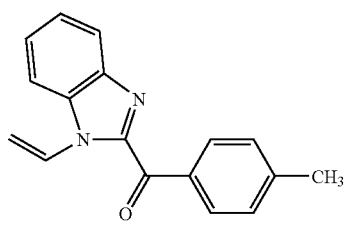

The compound of Example 25-1 (6.25 g, 26.5 mmol) was dissolved in isopropanol (100 ml), and thereto were added potassium carbonate (7.31 g, 52.9 mmol) and 1-chloro-2-bromoethane (19.0 g, 133 mmol), and the mixture was stirred at 70° C. for 16 hours. The reaction solution was allowed to cool to room temperature, and water was added thereto. The mixture was extracted with ethyl acetate. The organic layer was washed with water and saturated saline, dried over magnesium sulfate, and the solvent was evaporated under reduced pressure. The concentrated residue was dissolved in dimethylsulfoxide (30 ml), and thereto was added 1.8-diazabicyclo[5,4,0]undec-7-ene (DBU) (15.2 g, 100 mmol), and the mixture was stirred at 100° C. for 4 hours. To the mixture was added 1N diluted hydrochloric acid, and the mixture was extracted with ethyl acetate. The organic layer was washed with 1N diluted hydrochloric acid, water and saturated saline, and dried over magnesium sulfate. The solvent was evaporated under reduced pressure, and the resultant was purified by silica gel column chromatography to give the title compound (4.23 g, 65%).
LC-MS (Method B):R.T. 4.43 min., 263 m/z (M+1)

Reference Example 27

(1-But-3-en-1-yl-4-tert-butyl-1H-imidazol-2-yl)(4-methylphenoxy)methanone

Reference Example 27-1

4-tert-Butyl-1H-imidazole

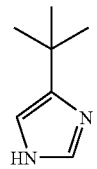

1-Bromo-3,3-dimethyl-2-butanone (5.00 g, 27.9 mmol) was dissolved in formamide (37.7 g, 83.7 mmol), and the mixture was stirred at 160° C. for 5 hours. The reaction solution was allowed to cool to room temperature, and thereto was added water (100 ml), and the aqueous layer was washed with hexane (50 ml). To the resulting aqueous layer was added 2N aqueous sodium hydroxide solution, and the pH value of the mixture was adjusted to about pH 10, and then extracted with chloroform. The organic layer was washed with water and saturated saline, and dried over magnesium sulfate. Then, the solvent was evaporated under reduced pressure to give the title compound (1.67 g, 48%).
$^1$H NMR (CDCl$_3$, 400 MHz) δ 7.56 (d, 1H, J=1.1 Hz), 6.77 (d, 1H, J=1.1 Hz), 1.31 (s, 9H).

Reference Example 27-2

1-But-3-en-1-yl-4-tert-butyl-1H-imidazole

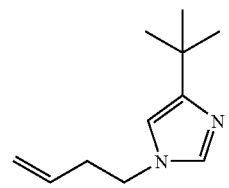

The compound of Reference Example 27-1 (992 mg, 8.00 mmol) was dissolved in DMF (10 ml), and thereto was added potassium t-butoxide (990 mg, 8.80 mmol), and the mixture was stirred at room temperature for 30 minutes. To the reaction solution was added 1-bromo-3-buten (1.62 g, 12.0 mmol), and the mixture was stirred at 80° C. for 2 hours. The reaction solution was allowed to cool to room temperature, and extracted with ethyl acetate. The organic layer was washed with water and saturated saline, and dried over magnesium sulfate. Then, the solvent was evaporated under reduced pressure, and the resultant was purified by silica gel column chromatography to give the title compound (623 mg, 44%).

$^1$H NMR (CDCl$_3$, 400 MHz) δ 7.38 (s, 1H), 6.60 (s, 1H), 5.74 (ddt, 1H, J=5.1, 15.2, 7.4 Hz), 5.09 (d, 1H, J=15.2 Hz), 5.08 (d, 1H, J=5.1 Hz), 3.92 (t, 2H, J=7.2 Hz), 2.51 (dt, 2H, J=7.4, 7.2 Hz), 1.28 (s, 9H).

Reference Example 27-3

(1-But-3-en-1-yl-4-tert-butyl-1H-imidazol-2-yl)(4-methylphenoxy)methanone

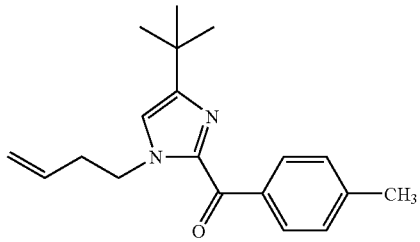

The compound of Reference Example 27-2 (53.5 mg, 0.300 mmol) was dissolved in pyridine (1 ml), and thereto were added successively triethylamine (91.1 mg, 0.900 mmol), 4-toluoyl chloride (139 mg, 0.900 mmol), and the mixture was stirred at 60° C. for 5 hours. The reaction solution was allowed to cool to room temperature, and thereto was added 1N aqueous sodium hydroxide solution (5 ml), and the mixture was stirred at room temperature for 1 hour. To the reaction solution was added water (10 ml), and the mixture was extracted with ethyl acetate. The organic layer was washed with water, 1N diluted hydrochloric acid, and saturated saline, and dried over magnesium sulfate. Then, the solvent was evaporated under reduced pressure, and the resultant was purified by silica gel column chromatography to give the title compound (29.4 mg, 33%).

$^1$H NMR (CDCl$_3$, 400 MHz) δ 8.30 (d, 2H, J=8.3 Hz), 7.27 (d, 2H, J=8.3 Hz), 6.86 (s, 1H), 5.77 (ddt, 1H, J=6.2, 17.1, 7.0 Hz), 5.07 (d, 1H, J=17.1 Hz), 5.06 (d, 1H, J=6.2 Hz), 4.42 (t, 2H, J=7.2 Hz), 2.59 (dt, 2H, J=7.0, 7.2 Hz), 2.42 (s, 3H), 1.32 (s, 9H).

Reference Example 28

(1-Allyl-4,5,6,7-tetrahydro-1H-benzimidazol-2-yl)(4-methylphenyl)methanone

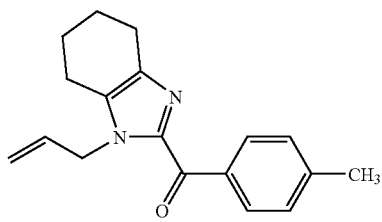

Using 2-chlorohexanone as a starting compound, the compound of Reference Example 28 was synthesized in a similar manner to Reference Example 27.

LC-MS(Method B): R.T. 3.40 min., m/z 281 (M+1)

Reference Example 29

(4-Methylphenyl)(3-vinyl-2-thienyl)methanone

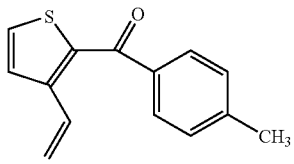

To 3-bromo-thiophene (15.7 g, 97 mmol) was added 4-toluoyl chloride (14.9 g, 97 mmol) in dichloromethane, and thereto was added dropwise tin chloride (IV) (25 g, 11.2 mmol), and the mixture was stirred at room temperature for 4 hours. To this reaction solution was added water, and the mixture was extracted with ethyl acetate. The solvent was evaporated under reduced pressure, and the resultant was purified by silica gel column chromatography to give an acyl compound. To a solution of the acyl compound (880 mg, 3.13 mmol) in toluene (2.27 ml) were added tri-N-butylvinyl tin (2.58 mg, 8.07 mmol) and tetrakis(triphenylphosphine)palladium (774 mg, 6.6 mmol), and the mixture was stirred at 110° C. for 4 hours. To this reaction solution was added water, and the mixture was extracted with ethyl acetate. The solvent was evaporated under reduced pressure, and the resultant was purified by silica gel column chromatography to give the title compound (710 mg).

$^1$H NMR (CDCl$_3$, 400 MHz) δ 7.75 (d, 2 H, J=8.2 Hz), 7.48 (d, 1H, J=5.2 Hz), 7.40 (d, 1H, 5.2 Hz), 7.26 (d, 2H, J=8.2 Hz), 7.13 (dd, 1H, J=11, 17 Hz), 5.73 (dd, 1H, J=1.2, 17 Hz), 5.35 (dd, 1H, J=1.2, 11 Hz), 2.43 (s, 3 H)

Reference Example 30

(1-Allyl-5-methoxy-1H-indol-2-yl)(4-methylphenyl)methanone

Reference Example 30-1

N,5-Dimethoxy-N-methyl-1H-indole-2-carboxamide

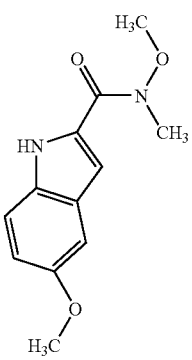

To a solution of 5-methoxyindole-2-carboxylic acid (5 g, 26 mmol) in N,N-dimethylformamide were added N,O-dimethylhydroxyamine hydrochloride (3.04 g, 31.2 mmol) and WSC (5.98 g, 31.2 mmol), 1-hydroxybenzotriazole (4.21 g, 31.2 mmol) and triethylamine (7.24 ml, 52 mmol), and the mixture was stirred for 6 hours. To this reaction solution were added ethyl acetate and 10% (Wt) citric acid, and the organic layer was extracted. The aqueous layer was extracted twice with ethyl acetate, and combined with the organic layer. The mixture was washed with a saturated aqueous sodium hydrogen carbonate solution and saturated saline. The organic layer was separated, and dried over anhydrous sodium sulfate, filtered, and the solvent was evaporated under reduced pressure. The residue was purified by silica gel column chromatography (hexane:ethyl acetate=4:1) to give the title compound (4.5 g, 70%).

$^1$H NMR (CDCl$_3$, 400 MHz) δ 9.23 (brs, 1H), 7.33 (d, 1H, J=9.0 Hz,), 7.16 (d, 1H, J=2.1 Hz), 7.10 (d, 1H, J=2.4 Hz), 6.98 (dd, 1H, J=2.4 Hz, J=9.0 Hz ),3.85 (d, 6H, J=3.9 Hz), 3.42 (s, 3H)

Reference Example 30-2

1-Allyl-N,5-dimethoxy-N-methyl-1H-indol-2-carboxamide

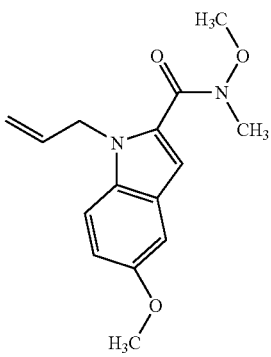

To a solution of the compound of Reference Example 30-1 (1 g, 4.27 mmol) in THF were added potassium t-butoxide (575 mg, 5.12 mmol) and allyl bromide (568 mmol, 4.7 mmol), and the mixture was stirred at room temperature for 3 hours. To this reaction solution were added ethyl acetate and 10% (Wt) citric acid, and the organic layer was extracted. This aqueous layer was extracted twice with ethyl acetate, and the extracts were combined with the organic layer. The mixture was washed with a saturated aqueous sodium hydrogen carbonate solution and saturated saline, and the organic layer was separated. The organic layer was dried over anhydrous sodium sulfate, filtered and the solvent was evaporated under reduced pressure. The resultant was purified by silica gel column chromatography (hexane:ethyl acetate=4:1) to give the title compound (820 mg, 70%).

$^1$H NMR (CDCl$_3$, 400 MHz) δ 7.3 (d, 1H, J=9.0 Hz,), 7.08 (d, 1H, J=2.4 Hz), 7.05 (s, 1H), 6.97 (dd, 1H, J=2.4, 9.0 Hz), 5.98 (m, 1H), 4.97 (m, 3H), 4.90 (dd, 1H, J=1.4, 17 Hz, 3.85 (s, 3 H), 3.67(s, 3H), 3.39 (s, 3H)

Reference Example 30-3

(1-Allyl-5-methoxy-1H-indol-2-yl)(4-methylphenyl)methanone

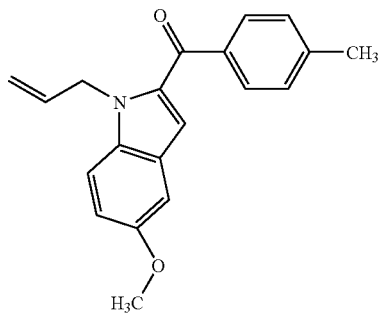

To a solution of the compound of Reference Example 30-2 (300 mg, 1.09 mmol) in THF was added a 1M solution of p-tolylmagnesium bromide in ether (1.31 ml, 1.31 mmol) under ice-cooling, and the mixture was stirred for 3 hours. To the reaction solution were added ethyl acetate and 10% (Wt) citric acid, and the organic layer was extracted. The aqueous layer was extracted twice with ethyl acetate, and the extracts were combined with the organic layer. The mixture was washed with a saturated aqueous sodium hydrogen carbonate solution and saturated saline. The organic layer was separated, and dried over anhydrous sodium sulfate, filtered, and the solvent was evaporated under reduced pressure. The residue was purified by silica gel column chromatography (hexane:ethyl acetate =4:1) to give the title compound (250 mg, 74%).

$^1$H NMR (CDCl$_3$, 400 MHz) δ 7.83 (d, 2H, J=8.2 Hz), 7.31 (m, 4H), 7.06 (m, 2H), 6.94 (s, 1H), 6.05 (ddt, 1H, J=1.3, 5.1, 17 Hz), 5.2 (ddd, 2H, J=1.3, 1.3 Hz, 5.1 Hz), 5.11(dd, 1H, J=1.3, 10 Hz), 4.96 (dd, 1H, J=1.3, 17 Hz), 3.85 (s, 3H), 2.45 (s, 3H)

Reference Example 31

3-{(1E)-3-[2-(4-Methylbenzoyl)-1H-pyrrol-1-yl]prop-1-enyl}benzoic acid

Reference Example 31-1

Ethyl 3-{(1E)-3-[2-(4-Methylbenzoyl)-1H-pyrrol-1-yl]prop-1-enyl}benzoate

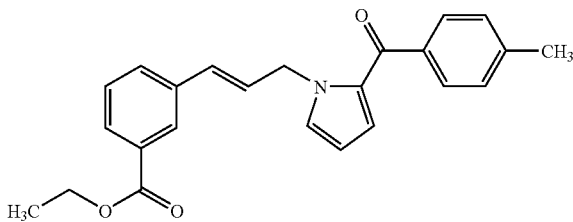

A mixture of ethyl 3-iodobenzoate (1.40 g, 5.07 mmol), the compound of Reference Example 1-3 (1.17 g, 5.19 mmol), sodium hydrogen carbonate (0.89 g, 10.6 mmol), benzyltriethylammonium chloride (1.25 g, 5.49 mmol), palladium acetate (60 mg, 0.27 mmol) in DMF (20 ml) was stirred at 70° C. for 7 hours. To the reaction solution was added a 5% aqueous sodium thiosulfate solution, and the mixture was extracted with a mixture of ethyl acetate and toluene (2/1). The organic layer was washed with water and saturated saline, dried over magnesium sulfate, and the solvent was evaporated under reduced pressure. The resulting residue was purified by silica gel column chromatography (hexane:ethyl acetate=5:1→4:1) to give the title compound (1.94 g).

$^1$H NMR (CDCl$_3$, 400 MHz) δ 8.02 (t, 1H, J=1.4 Hz), 7.90 (dt, 1H, J=7.8, 1.4 Hz), 7.74 (brd, 2H, J=8.1 Hz), 7.54 (dt, 1H, J=7.8, 1.4 Hz), 7.36 (t, 1H, J=7.8 Hz), 7.25 (brd, 2H, J=8.1 Hz), 7.05 (dd, 1H, J=2.6, 1.6 Hz), 6.78 (dd, 1H, J=4.0, 1.6 Hz), 6.47-6.57 (m, 2H), 6.23 (dd, 1H, J=4.0, 2.6 Hz), 5.21-5.25 (m, 2H), 4.37 (q, 2H, J=7.1 Hz), 2.43 (s, 3H), 1.39 (t, 3H, J=7.1 Hz).

Reference Example 31-2

3-{(1E)-3-[2-(4-Methylbenzoyl)-1H-pyrrol-1-yl]prop-1-enyl}benzoic acid

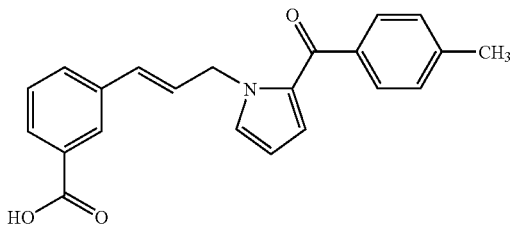

A solution of ethyl 3-{(1E)-3-[2-(4-methylbenzoyl)-1H-pyrrol-1-yl]prop-1-enyl}benzoate (1.94 g) in 1N aqueous lithium hydroxide solution (10 ml), THF (10 ml) and methanol (10 ml) were stirred at 50° C. for 3 hours. Methanol and THF in the reaction solution were evaporated under reduced pressure, and the residue was diluted with water, and washed with diethyl ether. The aqueous layer was acidified with diluted hydrochloric acid solution, and extracted with ethyl acetate. The organic layer was washed with saturated saline, dried over magnesium sulfate, and the solvent was evaporated under reduced pressure to give the title compound (1.66 g, yield for 2 steps: 93%).

$^1$H NMR (CDCl$_3$, 400 MHz) δ 8.07 (t, 1H, J=1.3 Hz), 7.95 (dt, 1H, J=7.8, 1.3 Hz), 7.74 (brd, 2H, J=8.1 Hz), 7.60 (dt, 1H, J=7.8, 1.3 Hz), 7.40 (t, 1H, J=7.8 Hz), 7.26 (brd, 2H, J=8.1 Hz), 7.06 (dd, 1H, J=2.6, 1.7 Hz), 6.79 (dd, 1H, J=4.0, 1.7 Hz), 6.55 (dt, 1H, J=15.9, 4.8 Hz), 6.51 (d, 1H, J=15.9 Hz), 6.23 (dd, 1H, J=4.0, 2.6 Hz), 5.24 (d, 2H, J=4.8 Hz), 2.43 (s, 3H).

Reference Example 32

4-{(1E)-3-[2-(4-Methylbenzoyl)-1H-pyrrol-1-yl]prop-1-en-1-yl}benzoic acid

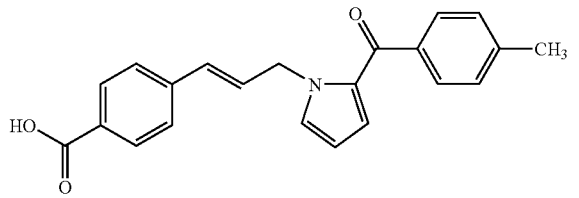

The title compound was synthesized from ethyl 4-iodobenzoate in a similar manner to Reference Example 31.

LC-MS (Method B): R.T. 3.78 min., m/z 346 (M+1)

Reference Example 33

(1-{(2E)-3-[4-(Bromomethyl)phenyl]prop-2-en-1-yl}-1H-pyrrol-2-yl)(4-methyl-phenyl)methanone Reference Example 33-1

(1-{(2E)-3-[4-(Hydroxymethyl)phenyl]prop-2-en-1-yl}-1H-pyrrol-2-yl)(4-methyl-phenyl)methanone

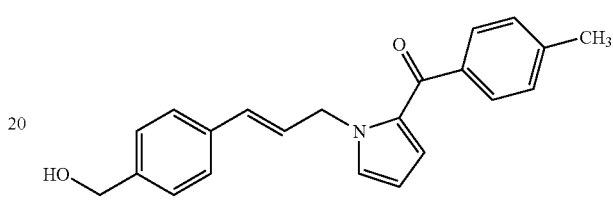

Under nitrogen atmosphere, to a solution of the compound of Reference Example 32 (93.2 g, 269.8 mmol) in THF (700 ml) was added triethylamine (36.6 g, 361.5 mmol), and thereto was added dropwise a solution of ethyl chloro-carbonate (33.7 g, 310.3 mmol) in THF (100 ml) under ice-cooling. The reaction solution was stirred under ice-cooling for 30 minutes, and the precipitated triethylamine hydrochloride was collected by filtration, and washed with THF (300 ml). The filtrate and the washing were combined, and thereto was added dropwise a solution of sodium borohydride (23.5 g, 620.5 mmol) in water (150 ml). The reaction solution was stirred under ice-cooling for 30 minutes. To the reaction solution was added a 1N aqueous potassium hydroxide solution (300 ml), and the mixture was extracted with toluene (500 ml). The resulting organic layer was washed with water (500 ml), a 5% aqueous potassium hydrogen sulfate solution (500 ml), and saturated saline (500 ml). The washed aqueous layers were combined, and extracted again with toluene (500 ml). The resulting organic layers were dried over magnesium sulfate, and the solvent was evaporated under reduced pressure to give the title compound (quant.).

$^1$H NMR (CDCl$_3$, 300 MHz) δ 7.73 (d, 2H, J=8.4 Hz), 7.36 (d, 2H, J=8.4 Hz), 7.28 (d, 2H, J=8.4 Hz), 7.25 (d, 2H, J=8.4 Hz), 7.05 (dd, 1H, J=2.5, 1.8 Hz), 6.77 (dd, 1H, J=4.0, 1.8 Hz), 6.50 (d, 1H, J=16.0 Hz), 6.43 (dt, 1H, J=16.0, 4.9 Hz), 6.21 (dd, 1H, J=4.0, 2.5 Hz), 5.20 (d, 2H, J=4.9 Hz), 4.66 (s, 2H), 2.42 (s, 3H).

Reference Example 33-2

(1-{(2E)-3-[4-(Bromomethyl)phenyl]prop-2-en-1-yl}-1H-pyrrole 2-yl)(4-methyl-phenyl)methanone

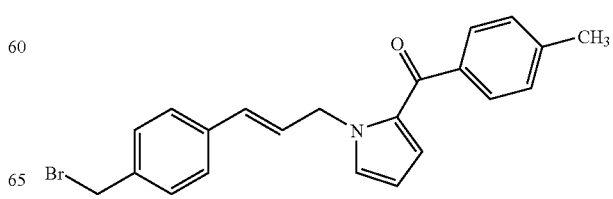

To a solution of the compound of Reference Example 33-1 (539.6 mmol) and triethylamine (82.0 g, 809.4 mmol) in THF (1700 ml) was added dropwise methanesulfonyl chloride (80.2 g, 701.4 mmol) under ice-cooling, and the mixture was stirred for 30 minutes. The mixture was acidified (pH 2) with 1N hydrochloric acid, and thereto was added toluene (200 ml). The organic layer was separated and dried over anhydrous magnesium sulfate. Separately, lithium bromide monohydrate (115 g, 1096.7 mmol) was subjected to azeotropic distillation with toluene twice, and a THF (240 ml) thereof was prepared. This THF solution was added dropwise to the above toluene solution under ice-cooling. The mixture was warmed to room temperature, and stirred for one hour. To the mixture was added water (600 ml), and the organic layer was separated. The organic layer was washed with saturated saline and dried over anhydrous magnesium sulfate. The solvent was evaporated under reduced pressure, and the resulting residue was filtered through silica (solvent: toluene/hexane (1/1)). The filtrate was concentrated under reduced pressure, and the resulting residue was recrystallized from toluene/hexane (1/2). The residue in the mother liquor was further recrystallized to give the title compound (142.72 g, 67%).

$^1$H NMR (CDCl$_3$, 300 MHz) δ 7.73 (d, 2H, J=7.5 Hz), 7.34 (d, 2H, J=9.0 Hz), 7.30 (d, 2H, J=9.0 Hz), 7.25 (d, 2H, J=7.5 Hz), 7.04 (dd, 1H, J=2.6, 1.7 Hz), 6.77 (dd, 1H, J=4.1, 1.7 Hz), 6.52-6.38 (m, 2H), 6.21 (dd, 1H, J=4.1, 2.6 Hz), 5.20 (d, 2H, J=4.4 Hz), 4.47 (s, 2H), 2.42 (s, 3H).

Reference Example 34

(1-{(2E)-3-[3-(Bromomethyl)phenyl]prop-2-en-1-yl}-1H-pyrrol-2-yl) (4-methyl-phenyl)methanone Reference Example 34-1

(1-{(2E)-3-[3-(Hydroxymethyl)phenyl]prop-2-en-1-yl}-1H-pyrrol-2-yl) (4-methyl-phenyl)methanone

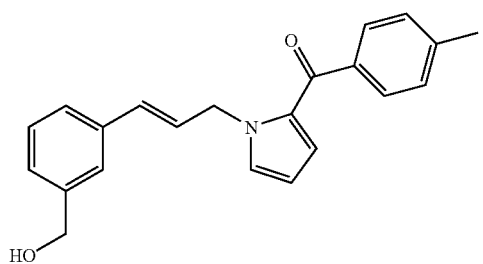

The title compound was synthesized in a similar manner to Reference Example 33-1.

$^1$H NMR (CDCl$_3$, 400 MHz) δ 7.73 (d, 2 H, J=8.1 Hz), 7.37 (s, 1 H), 7.30-7.15 (m, 5 H), 7.04 (dd, 1 H, J=1.7, 2.5 Hz), 6.77 (dd, 1 H, J=1.7, 4.0 Hz), 6.53-6.41 (m, 2 H), 6.20 (dd, 1 H, J=2.5, 4.0 Hz), 5.20 (d, 2 H, J=4.7 Hz), 4.66 (d, 2 H, J=5.9 Hz), 2.42 (s, 3 H), 1.74 (t, 1 H, J=5.9 Hz).

Reference Example 34-2

(1-{(2E)-3-[3-(Bromomethyl)phenyl]prop-2-en-1-yl}-1H-pyrrol-2-yl)(4-methyl-phenyl)methanone

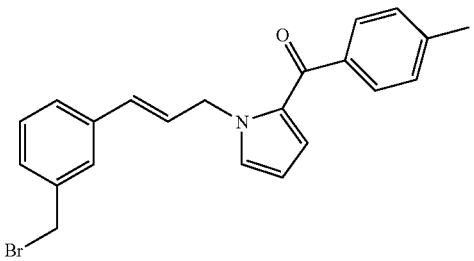

The title compound was synthesized in a similar manner to Reference Example 33-2.

$^1$H NMR (CDCl$_3$, 400 MHz) δ 7.74 (d, 2H, J=8.1 Hz), 7.38 (s, 1H), 7.30-7.24 (m, 5H), 7.04 (dd, 1H, J=1.7, 2.5 Hz), 6.77 (dd, 1H, J=1.7, 4.0 Hz), 6.51-6.43 (m, 2H), 6.21 (dd, 1H, J=2.5, 4.0 Hz), 5.20 (d, 2H, J=4.4 Hz), 4.46 (s, 2H), 2.43 (s, 3H).

Reference Example 35

(1-{2-[3-(Bromomethyl)phenoxy]ethyl}-1H-pyrrol-2-yl)(4-methylphenyl)-methanone

Reference Example 35-1

Methyl[2-(4-methylbenzoyl)-1H-pyrrol-1-yl]acetate

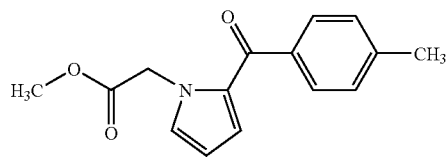

To a solution of the compound of Reference Example 1-2 (220 mg, 1.19 mmol) in THF (3 ml) was added potassium t-butoxide (170 mg, 1.52 mmol), and the mixture was stirred at room temperature for 15 minutes. To this reaction solution was added methyl bromoacetate (215 mg, 1.41 mmol), and the mixture was stirred at room temperature for 6 hours. To the reaction solution was added a 5% aqueous potassium hydrogen sulfate solution, and the mixture was extracted with ethyl acetate. The organic layer was washed with a saturated saline, dried over magnesium sulfate, and the solvent was evaporated under reduced pressure. The resulting residue was separated and purified by silica gel column chromatography (hexane:ethyl acetate=4:1→3:1) to give the title compound (257 mg, 84%).

$^1$H NMR (CDCl$_3$, 400 MHz) δ 7.72 (d, 2H, J=8.1 Hz), 7.25 (d, 2H, J=8.1 Hz), 6.94 (dd, 1H, J=2.5, 1.7 Hz), 6.82 (dd, 1H, J=4.0, 1.7 Hz), 6.25 (dd, 1H, J=4.0, 2.5 Hz), 5.11 (s, 2H), 3.79 (s, 3H), 2.42 (s, 3H).

Reference Example 35-2

[2-(4-Methylbenzoyl)-1H-pyrrol-1-yl]acetic acid

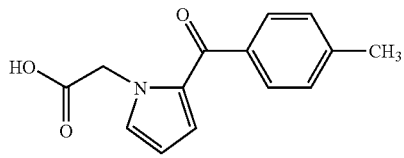

A solution of the compound of Reference Example 35-1 (255 mg, 0.991 mmol) in THF (2 ml), a 1N aqueous lithium hydroxide solution (2 ml) and methanol (2 ml) was stirred at room temperature for 30 minutes. To the reaction solution was added diluted hydrochloric acid, and the mixture was extracted with ethyl acetate. The organic layer was washed with a saturated saline, dried over magnesium sulfate, and the solvent was evaporated under reduced pressure to give the title compound (232 mg, 96%).

$^1$H NMR (CDCl$_3$, 400 MHz) δ 7.77 (d, 2H, J=8.1 Hz), 7.28 (d, 2H, J=8.1 Hz), 7.06 (dd, 1H, J=2.5, 1.7 Hz), 6.86 (dd, 1H, J=4.1, 1.7 Hz), 6.30 (dd, 1H, J=4.1, 2.5 Hz), 5.02 (s, 2H), 2.45 (s, 3H).

Reference Example 35-3

[1-(2-Hydroxyethyl)-1H-pyrrol-2-yl](4-methylphenyl)methanone

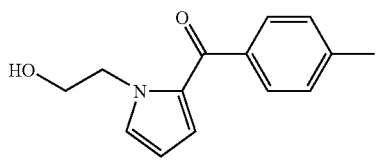

To a solution of the compound of Reference Example 35-2 (1.34 g, 5.51 mmol) in THF (20 ml) were added triethylamine (0.60 g, 5.93 mmol) and ethyl chlorocarbonate (0.90 g, 8.29 mmol) under ice-cooling, and the mixture was stirred at 0° C. for one hour. To the reaction solution was added a solution of sodium borohydride (0.40 g, 10.6 mmol) in water (10 ml), and the mixture was stirred at 0° C. for 1 hour. To the reaction solution was added diluted aqueous hydrochloric acid solution, and the mixture was extracted with ethyl acetate. The organic layer was washed with water, a saturated aqueous sodium hydrogen carbonate solution, and a saturated saline, dried over magnesium sulfate, and the solvent was evaporated under reduced pressure. The resulting residue was purified and separated by silica gel column chromatography (hexane:ethyl acetate=1:1→2:3) to give the title compound (1.04 g, 82%).

$^1$H NMR (CDCl$_3$, 400 MHz) δ 7.73 (dd, 2H, J=8.1 Hz), 7.26 (d, 2H, J=8.1 Hz), 7.06 (dd, 1H, J=2.5, 1.7 Hz), 6.77 (dd, 1H, J=4.1, 1.7 Hz), 6.23 (dd, 1H, J=4.1, 2.5 Hz), 4.53 (t, 2H, J=5.0 Hz), 4.03 (dt, 2H, J=5.0, 5.0 Hz), 3.20 (brt, 1H, J=5.0 Hz), 2.43 (s, 3 H).

Reference Example 35-4

Methyl 3-{2-[2-(4-methylbenzoyl)-1H-pyrrol-1-yl]ethoxy}benzoate

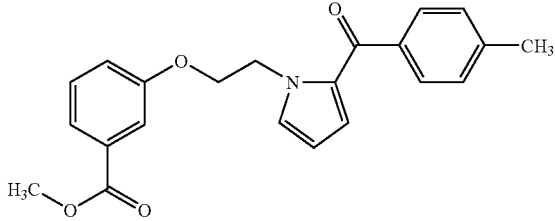

To a solution of the compound of Reference Example 35-3 (100 mg, 0.460 mmol) in THF (5 ml) were added methyl 3-hydroxybenzoate (70 mg, 0.460 mmol), triphenylphosphine (150 mg, 0.572 mmol), diethyl azodicarboxylate (40% toluene solution, 250 mg, 0.574 mmol), and the mixture was stirred at room temperature for 14 hours. This reaction solution was concentrated under reduced pressure, and the resulting residue was purified by silica gel column chromatography (hexane:ethyl acetate=3:1→2:1) to give the title compound (117 mg, 74%).

$^1$H NMR (CDCl$_3$, 400 MHz) δ 7.71 (d, 2H, J=8.1 Hz), 7.62 (ddd, 1H, J=7.7, 1.3, 0.9 Hz), 7.51 (dd, 1H, J=2.7, 1.3 Hz), 7.31 (dd, 1H, J=8.2, 7.7 Hz), 7.25 (d, 2H, J=8.1 Hz), 7.13 (dd, 1H, J=2.5, 1.7 Hz), 7.06 (ddd, 1H, J=8.2,2.7,0.9 Hz), 6.77 (dd, 1H, J=4.0,1.7 Hz), 6.18 (dd, 1H, J=4.0, 2.5 Hz), 4.79 (t, 2H, J=5.0 Hz), 4.41 (t, 2H, J=5.0 Hz), 3.90 (s, 3H), 2.42 (s, 3H).

Reference Example 35-5

(1-{2-[3-(Bromomethyl)phenoxy]ethyl}-1H-pyrrol-2-yl) (4-methylphenyl)-methanone

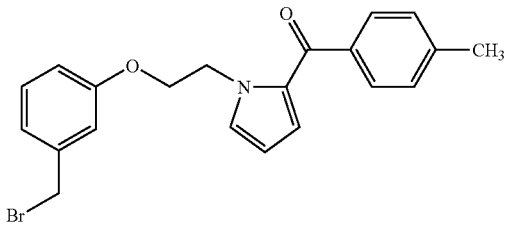

The title compound was synthesized in a similar manner to Reference Example 33-2.
LC-MS (Method A): R.T. 2.66 min., m/z 398 (M+1)

Reference Example 36

[1-(2-{[5-(Hydroxymethyl)pyridin-2-yl]oxy}ethyl)-1H-pyrrol-2-yl](4-methylphenyl)-methanone

Reference Example 36-1

Methyl 6-hydroxynicotinate

To a suspension of 6-hydroxynictonic acid (5.23 g, 37.6 mmol) in methanol (60 ml) was added dropwise thionyl chloride (5.0 g, 42.0 mmol) at 55° C., and the reaction mixture was stirred at 55° C. for one hour. To the reaction mixture was further added thionyl chloride (3.3 g, 27.7 mmol), and the mixture was stirred at 55° C. for 3 hours, and then further stirred at room temperature overnight. The reaction solution was neutralized (around pH 7) with a saturated aqueous sodium hydrogen carbonate solution and a 1N aqueous sodium hydroxide solution, and further it was made a saturated solution with sodium chloride. The reaction mixture was extracted three times with ethyl acetate. The organic layers were combined, and washed with a saturated saline, dried over magnesium sulfate, and the solvent was evaporated under reduced pressure to give the title compound (3.15 g, 55%).

$^1$H-NMR (400 MHz in CDCl$_3$) δ 12.65 (1H, brs), 8.19 (1H, d, J=2.5 Hz), 8.00 (1H, dd, J=9.6, 2.5 Hz), 6.58 (1H, d, J=9.6 Hz), 3.87 (3H, s).

Reference Example 36-2

Methyl 6-{2-[2-(4-methylbenzoyl)-1H-pyrrol-1-yl]ethoxy}nicotinate

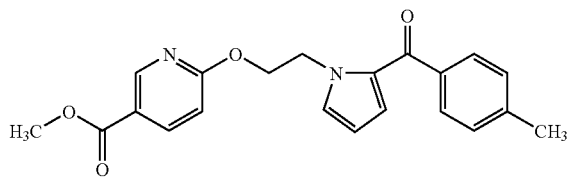

To a suspension of the compound of Reference Example 36-1 (202 mg, 1.32 mmol) and the compound of Reference Example 35-3 (297 mg, 1.30 mmol) in THF (15 ml) were added under ice-cooling triphenylphosphine (0.50 g, 1.91 mmol), a 40% solution of isopropyl azodicarboxylate in toluene (0.90 g, 1.78 mmol), and the reaction solution was stirred at room temperature for 110 hours. The reaction solution was concentrated, and the residue was purified by silica gel column chromatography (hexane:ethyl acetate=4:1→12:1) to give the title compound (352 mg, 74%).

$^1$H-NMR (400 MHz in CDCl$_3$) δ 8.77 (1H, dd, J=2.4, 0.48 Hz), 8.13 (1H, dd, J=8.7, 2.4 Hz), 7.71 (2H, d, J=8.1 Hz), 7.25 (2H, d, J=8.1 Hz), 7.00 (1H, dd, J=2.5, 1.7 Hz), 6.75 (1H, dd, J=4.0, 1.7 Hz), 6.70 (1H, dd, J=8.7, 0.48 Hz), 6.15 (1H, dd, J=4.0, 2.5 Hz), 4.74-4.84 (4H, m), 3.90 (3H, s), 2.43 (3H, s).

Reference Example 36-3

6-{2-[2-(4-Methylbenzoyl)-1H-pyrrol-1-yl]ethoxy}nicotinic acid

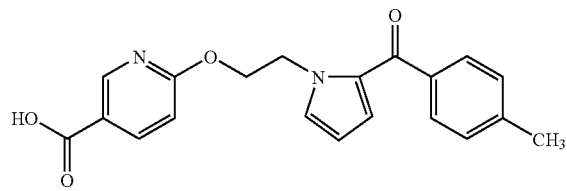

To a solution of the compound of Reference Example 36-2 (251 mg, 0.689 mmol) in THF (5 ml) and methanol (3 ml) was added a 2N aqueous lithium hydroxide solution (5 ml), and the mixture was stirred at room temperature for 16 hours. The pH value of the reaction solution was adjusted to pH 3 with a 5% aqueous potassium hydrogen sulfate solution, and the mixture was extracted with ethyl acetate. The organic layer was washed with saturated saline, dried over magnesium sulfate, and the solvent was evaporated under reduced pressure to give the title compound (243 mg).

$^1$H-NMR (400 MHz in CDCl$_3$) δ 8.84 (1H, dd, J=2.4, 0.48 Hz), 8.16 (1H, dd, J=8.7, 2.4 Hz), 7.71 (2H, d, J=8.1 Hz), 7.26 (2H, d, J=8.1 Hz), 7.01 (1H, dd, J=2.5, 1.7 Hz), 6.76 (1H, dd, J=4.0, 1.7 Hz), 6.73 (1H, dd, J=8.7, 0.48 Hz), 6.15 (1H, dd, J=4.0, 2.5 Hz), 4.76-4.84 (4H, m), 2.43 (3H, s).

Reference Example 36-4

[1-(2-{[5-(Hydroxymethyl)pyridin-2-yl]oxy}ethyl)-1H-pyrrol-2-yl](4-methyl-phenyl)methanone

To a solution of the compound of Reference Example 36-3 (135 mg, 0.385 mmol) in THF (5 ml) were added under ice-cooling triethylamine (47 mg, 0.464 mmol) and ethyl chlorocarbonate (50 mg, 0.461 mmol), and the mixture was stirred at 0° C. for 30 minutes. To this reaction solution was added dropwise under ice-cooling a solution of sodium borohydride (55 mg, 1.45 mg) in water (2 ml), and the mixture was stirred at room temperature for 3 hours. To the reaction solution was added a solution of sodium borohydride (60 mg, 1.59 mg) in water (1 ml), and the mixture was stirred at room temperature for 15 minutes. To the reaction solution was added a 5% aqueous sodium hydrogen sulfate solution, and the mixture was stirred at room temperature for 5 minutes, and neutralized with a saturated aqueous sodium hydrogen carbonate solution, and the mixture was extracted with ethyl acetate. The organic layer was washed with a saturated saline, dried over magnesium sulfate, and the solvent was evaporated under reduced pressure. The residue was purified by silica gel column chromatography (hexane:ethyl acetate=1:1→1:2) to give the title compound (87 mg, 67%).

$^1$H-NMR (400 MHz in CDCl$_3$) δ 8.09 (1H, d, J=2.4 Hz), 7.71 (2H, d, J=8.1 Hz), 7.60 (1H, dd, J=8.5, 2.4 Hz), 7.25 (2H, d, J=8.1 Hz), 7.02 (1H, dd, J=2.5, 1.7 Hz), 6.75 (1H, dd, J=2.5, 1.7 Hz), 6.69 (1H, d, J=8.5 Hz), 6.15 (1H, dd, J=4.0, 2.5 Hz), 4.81 (2H, t, J=5.2 Hz), 4.68 (2H, t, J=5.2 Hz), 4.62 (2H, d, J=5.7 Hz), 2.43 (3H, s), 1.59 (1H, t, J=5.7 Hz).

Reference Example 37

4-Iodobenzyl bromide

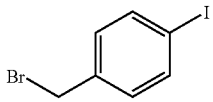

To a solution of 4-iodotoluene (10.0 g, 45.9 mmol) in dichloromethane (70 ml) were added successively bromine (3.6 ml, 69.9 mmol), a 30% solution of hydrogen peroxide solution (5.2 g, 45.9 mmol) in water (70 ml) at room temperature. The reaction solution was warmed, and vigorously stirred under reflux for 10 hours (the bath temperature: 50° C.).

The reaction solution was transferred into a separatory funnel, and thereto were added chloroform (40 ml) and water (20 ml), and the organic layer was washed three times with water (150 ml). The organic layer was washed successively with 0.5% aqueous sodium sodium hydrogen sulfite solution (150 ml) and water (150 ml), and the solvent was evaporated under reduced pressure (the bath temperature: 25° C.). Before the solvent was completely removed, toluene (50 ml) was added thereto, and the concentration procedure was repeated twice. The resultant was concentrated to dryness, and the residue was dried under vacuum to give iodobenzyl bromide (12.1 g).

$^1$H NMR (CDCl$_3$, 400 MHz) δ 7.68 (d, 2H, J=8.3 Hz), 7.13 (d, 2H, J=8.3 Hz), 4.23 (s, 2 H)

Reference Example 38

2-[(4-Iodobenzyl)oxy]-2-methylpropionic acid

Reference Example 38-1

Methyl 2-[(4-iodobenzyl)oxy]-2-methylpropionate

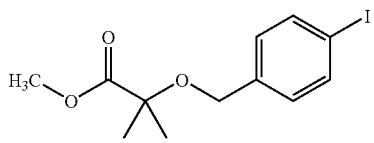

To a suspension of sodium hydride (60% in parafin liquid) (2.22 g, 55.5 mmol) in DMF (25 ml) was added dropwise a solution of methyl 2-hydroxy-isobutyrate (6.44 g, 54.5 mmol) in DMF (12 ml) over a period of 20 minutes (the inner temperature: 20° C.). The reaction solution was stirred at 22-23° C. for 30 minutes (the bath temperature: 23° C.). To this reaction solution was added dropwise a solution of 4-iodobenzyl bromide (15.4 g, 51.9 mmol) in DMF (35 ml) over a period of 20 minutes (the inner temperature: 22-26° C.). This reaction solution was stirred at 22-25° C. for 2.5 hours. To the reaction solution were added toluene (80 ml) and water (50 ml), and the mixture was stirred for 5 minutes. The mixture was transferred into a separatory funnel, and separated. The organic layer was washed with water, and concentrated to give a mixture of methyl ester compounds. A part of the mixture was purified by silica gel column chromatography (hexane:ethyl acetate=5:1) to give the title compound.

$^1$H NMR (CDCl$_3$, 400 MHz) δ 7.66 (d, 2H, J=8.3 Hz), 7.14 (d, 2H, J=8.3 Hz), 4.40 (s, 2H), 3.75 (s, 3H), 1.50 (s, 6H)

Reference Example 38-2

2-[(4-Iodobenzyl)oxy]-2-methylpropionic acid

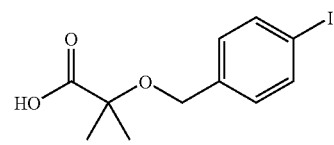

The mixture of Reference Example 38-1 was dissolved in THF (50 ml) and methanol (50 ml), and thereto was added a 3 N aqueous potassium hydroxide solution (40 ml), and the mixture was stirred at 30° C. for one hour. To the reaction solution was added toluene (70 ml), and the mixture was transferred into a separatory funnel (washed with toluene (10 ml) and water (20 ml)), and separated. The aqueous layer was acidified (pH 1-2) with conc. hydrochloric acid (about 17 ml), and the mixture was extracted with toluene (100 ml). The organic layer was washed with water (60 ml), concentrated to dryness, and dried under vacuum to give a mixture of the title compound (12.9 g). The mixture of the title compound (22.7 g) was suspended in toluene (70 ml), and the resulting suspension was warmed to 60° C. and dissolved. The heater for the heating bath was cut off, and the mixture was stirred while it was gradually cooled. Since crystals began to precipitate at 45° C., the mixture was stirred at 50° C. for 10 minutes. To this suspension was added hexane (70 ml), and the mixture was stirred at 50° C. for 10 minutes. The bath for heating was removed, and the mixture was stirred at room temperature for 20 minutes, and then stirred under ice-cooling for 20 minutes. The precipitated crystals were collected by filtration to give the title compound (21.0 g).

$^1$H NMR (CDCl$_3$, 400 MHz) δ 7.67 (d, 2H, J=8.3 Hz), 7.13 (d, 2H, J=8.3 Hz), 4.47 (s, 2H), 1.55 (s, 6H)

Reference Example 39

(2R)-2-[(4-Iodobenzyl)oxy]propionic acid

Reference Example 39-1

(2R)-2-[(4-Iodobenzyl)oxy]propionic acid (1S)-1-phenylethanamine salt

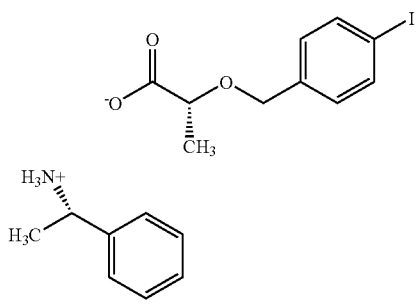

To a solution of methyl (R)-lactate (116 mg, 1.12 mmol) in THF (20 ml) was added sodium hydride (60% in parafin liquid) (45 mg, 1.12 mmol) at 0° C., and the mixture was stirred at room temperature for 15 minutes. To the reaction mixture was added the compound of Reference Example 37 (300 mg, 1.12 mmol), and the mixture was stirred at room temperature for 5 hours. To this reaction solution was added a saturated aqueous ammonium chloride solution, and the mixture was extracted with ethyl acetate. The organic layer was dried over anhydrous sodium sulfate, and the solvent was evaporated under reduced pressure. To the resultant were added a 3N aqueous sodium hydroxide solution (1 ml), THF (1 ml) and methanol (1 ml), and the mixture was stirred at room temperature for 3 hours. Toluene (3 ml) was added thereto, and the aqueous layer was separated, and acidified with 1N hydrochloride acid (pH 2). To the mixture was added toluene (3 ml), and the organic layer was separated, dried over anhydrous sodium sulfate, and the solvent was removed under reduced pressure to give a carboxylic acid compound (210 mg, 67%, 60% ee).

To the resulting carboxylic acid compound (100 mg) was added (S)-1-phenylethylamine (40 mg), and the mixture was dissolved in chloroform (1.75 ml) at 70° C. Hexane (1.75 ml) was added dropwise thereto, and the mixture was cooled to 0° C. over a period of 10 hours. The mixture was further stirred at 0° C. for 3 hours, during which the precipitated white solid was collected by filtration to give the title compound (85 mg, 63%)

$^1$H NMR (CDCl$_3$, 400 MHz) δ 7.61 (d, 2 H, J=8.3 Hz), 7.4-7.2 (m, 5H), 7.00 (d, 2H, J=8.3 Hz), 4.34 (d, 1H, J=12 Hz), 4.15 (d, 1H, J=12 Hz), 4.02 (q, 1H, 6.8 Hz), 3.71 (q, 1H, 6.8 Hz), 1.47 (d, 3H, J=6.8 Hz), 1.2 (d, 3H, J=6.8 Hz).

Results of Analysis; optical purity: 99.5% ee.

(Condition for resolution: 11.8 min, Condition for HPLC: Column: CHIRALCEL OD-RH (5 μm, 6 mmΦ×15 cm), the solvent for elution: Solution A, 0.1% trifluoroacetic acid/water, Solution B, acetonitrile, Solution A:Solutin B=2:1 (constant), Flow rate: 1 ml/min), UV: 254 nm Reference Example 39-2

(2R)-2-[(4-Iodobenzyl)oxy]propionic acid

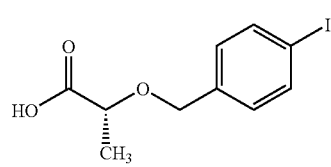

Water was added to the compound of Reference Example 39-1 (500 mg, 1.17 mmol), and the mixture was acidified with 1N hydrochloric acid (pH 2), and thereto was added toluene (1 ml). The organic layer was extracted to give a carboxylic acid (336 mg, 94%, 1.1 mmol).

LC-MS (Method B): r.t. 3.17 min., m/z 306 (M+1)

Reference Example 40

(2S)-2-[(4-Iodobenzyl)oxy]propionic acid

Reference Example 40-1

(2S)-2-[(4-Iodobenzyl)oxy]propionic acid (1R)-1-phenylethanamine salt

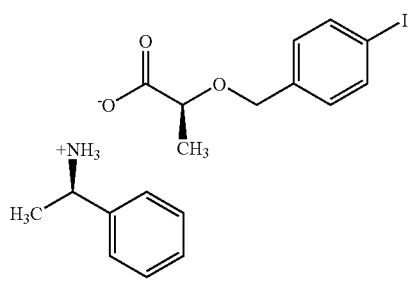

Using methyl (S)-lactate and (R)-1-phenylethylamine, the title compound was synthesized in a similar manner to Reference Example 39-1.

$^1$H NMR (CDCl$_3$, 400 MHz) δ 7.61 (d, 2H, J=8.3 Hz), 7.4-7.2 (m, 5H), 7.00 (d, 2H, J=8.3 Hz), 4.34 (d, 1H, J=12 Hz), 4.15 (d, 1H, J=12 Hz), 4.02 (q, 1H, 6.8 Hz), 3.71 (q, 1H, 6.8 Hz), 1.47 (d, 3H, J=6.8 Hz), 1.2 (d, 3H, J=6.8 Hz).

Results of Analysis: optical purity: 99.5% ee.

(Conditions for Resolution: 12.9 min; Conditions for HPLC: column, CHIRALCEL OD-RH (5 μm, 6 mmΦ×15 cm)

Solvent for elution: Solution A, 0.1% trifluoroacetic acid/water, Solution B, acetonitrile, Solution A:Solution B=2:1 (constant), Flow rate: 1 ml/min), UV: 254 nm)

Reference Example 40-2

(2S)-2-[(4-Iodobenzyl)oxy]propionic acid

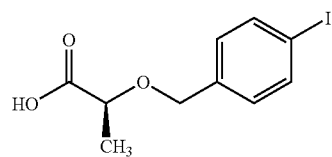

The title compound was synthesized in a similar manner to Reference Example 39-2.

LC-MS (Method B): r.t. 3.17 min., m/z 306 (M+1)

Reference Example 41

1-(1-Bromoethyl)-4-iodobenzene

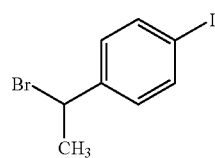

To a solution of iodoacetophenone (1 g, 4.06 mmol) in THF (2 ml) was added dropwise a solution of sodium borohydride (356 mg, 9.41 mmol) in water (2 ml) under ice-cooling, and the mixture was stirred at room temperature for 3 hours. To the reaction solution was added a 5% aqueous sodium hydrogen sulfate solution, and the mixture was stirred at room temperature for 5 minutes. The mixture was neutralized with a saturated aqueous sodium hydrogen carbonate solution, and extracted with ethyl acetate. The organic layer was washed with saturated saline, dried over magnesium sulfate, and the solvent was removed under reduced pressure. The residue was purified by silica gel column chromatography (hexane: ethyl acetate=5:1) to give an alcohol compound (690 mg, yield: 68%). To a solution of the alcohol compound (350 mg, 1.41 mol) in dichloromethane (5 ml) were added NBS (376 mg, 2.12 mmol) and triphenylphosphine (480 mg, 1.83 mmol) under ice-cooling, and the mixture was stirred at room temperature for 3 hours. To the reaction solution was added a 5% aqueous sodium hydrogen sulfate solution, and the mixture was stirred at room temperature for 5 minutes. The mixture was neutralized with a saturated aqueous sodium hydrogen carbonate solution, and extracted with ethyl acetate. The organic layer was washed with saturated saline, dried over magnesium sulfate, and the solvent was evaporated under reduced pressure. The residue was purified by silica gel column chromatography (hexane:ethyl acetate=5:1) to give the title compound (690 mg, yield: 80%).

$^1$H NMR (CDCl$_3$, 400 MHz) δ 7.61 (d, 2H, J=8.5 Hz), 7.18 (d, 2H, J=8.5 Hz), 5.14 (c, 1H, J=6.9 Hz), 2.01 (d, 3H, J=6.9 Hz)

Reference Example 42

Ethyl 2-[1-(4-iodophenyl)ethoxy]propanoate

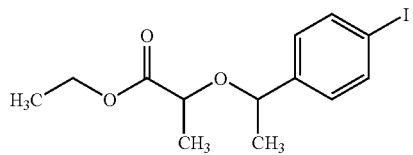

To a solution of ethyl (±)-lactate (64.8 mg, 0.549 mmol) in dimethyl-formamide (1 ml) was added sodium hydride (60% in parafin liquid) (22 mg, 0.549 mmol) at 0° C., and the mixture was stirred at room temperature for 15 minutes. To the mixture was added 3-bromobenzyl bromide (170 mg, 0.549 mmol), and the mixture was stirred at room temperature for 12 hours. To the reaction solution were added ethyl acetate and a saturated aqueous ammonium chloride solution, and the organic layer was separated. The aqueous layer was extracted twice with ethyl acetate, and the extracts were combined with the organic layer. The organic layer was collected, dried over anhydrous sodium sulfate, filtered, and the solvent was evaporated under reduced pressure. The resultant was purified by silica gel column chromatography (hexane:ethyl acetate=10:1) to give the title compound (10 mg, 5.2%).

$^1$H NMR (CDCl$_3$, 400 MHz) δ 7.67 (d, 2H, J=8.3 Hz), 7.04 (d, 2H, J=8.3 Hz), 4.45 (c, 1H, J=6.5 Hz), 4.5-4.2 (m, 2H), 3.79 (c, 1H, J=6.9 Hz), 1.47 (d, 3H, J=6.5 Hz), 1.33 (d, 3H, J=6.9 Hz), 1.28 (d, 3H, J=7.1 Hz)

Reference Example 43

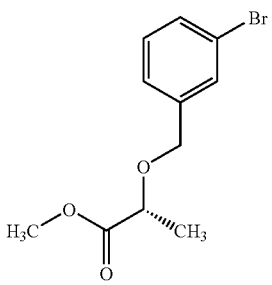

Using methyl (R)-lactate and 3-bromobenzyl bromide, the title compound was synthesized in a similar manner to Reference Example 42.

LC-MS (Method A): r.t. 2.27 min., m/z 273 (M+1)

Reference Example 44

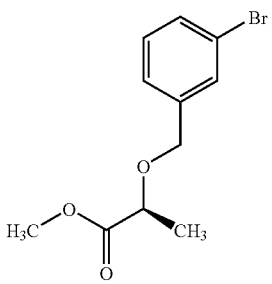

Using methyl (S)-lactate and 3-bromobenzyl bromide, the title compound was synthesized in a similar manner to Reference Example 42.

LC-MS (Method A): r.t. 2.27 min., m/z 273 (M+1)

Reference Example 45

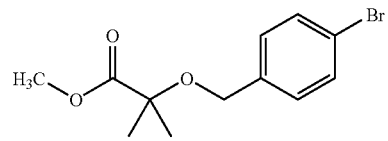

Using methyl 2-hydroxyisobutyrate and 3-bromobenzyl bromide, the title compound was synthesized in a similar manner to Reference Example 42.

LC-MS (Method A): r.t. 2.37 min., m/z 287 (M+1)

Reference Example 46

Ethyl 2-[2-(4-bromophenyl)ethoxy]-2-methylpropionate

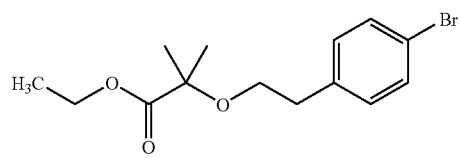

To a solution of 2-(4-bromophenyl)ethanol (1 g, 5 mmol) in THF (15 ml) was added sodium hydride (60% in parafin liquid) (220 mg, 5.5 mmol) at 0° C., and the mixture was stirred at room temperature for 15 minutes. To the mixture was added ethyl 2-bromoisobutyrate (1.08 g, 5.5 mmol), and the mixture was stirred at room temperature for 12 hours. To this reaction solution were added ethyl acetate and a saturated aqueous ammonium chloride solution, and the organic layer was separated. The aqueous layer was extracted twice with ethyl acetate, and the extracts were combined with the organic layer. The organic layer was collected, dried over anhydrous sodium sulfate, filtered, and the solvent was evaporated under reduced pressure. The resultant was purified by silica gel column chromatography (hexane:ethyl acetate=10:1) to give the title compound (240 mg, 15%).

LC-MS (Method A): r.t. 2.55 min., m/z 315 (M+1)

Example 1A

Methyl 2-methyl-2-[(3-{(1-E)-3-[2-(4-methylbenzoyl)-1H-pyrrol-1-yl]prop-1-en-1-yl}benzyl)oxy]propionate 1A-1

Methyl 2-(3-bromobenzyloxy)-2-methylpropionate

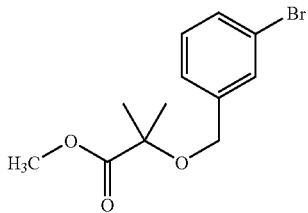

To a solution of methyl 2-hydroxyisobutyrate (1 g, 4.0 mmol) in THF (20 ml) was added sodium hydride (60% in parafin liquid) (115 mg, 4.8 mmol) at 0° C., and the mixture was stirred at room temperature for 15 minutes. To the mixture was added 3-bromobenzyl bromide (567 mg, 4.8 mmol), and the mixture was stirred at 50° C. for 12 hours. To the reaction solution was added a saturated aqueous ammonium chloride solution, and the mixture was extracted with ethyl acetate. The organic layer was dried over anhydrous sodium sulfate, and the solvent was evaporated under reduced pressure. The resulting residue was purified by silica gel column chromatography (hexane:ethyl acetate=10:1) to give the title compound (520 mg, 52%).

$^1$H NMR (CDCl$_3$, 400 MHz) δ 7.56 (s, 1H), 7.40 (d, 1H, J=7.9 Hz), 7.29 (d, 1H, J=7.9 Hz), 7.20 (dd, 1H, J=7.9, 7.9 Hz), 4.44 (s, 2H), 3.76 (s, 3H), 1.56 (s, 6H)

LC-MS (Method A): r.t. 2.30 min., m/z 287 (M+1)

1A-2

Methyl 2-methyl-2-[(3-{(1E)-3-[2-(4-methylbenzoyl)-1H-pyrrol-1-yl]prop-1-en-1-yl}benzyl)oxy]propionate A solution of the compound of Example 1A-1 (300 mg, 1.05 mmol), the compound of Reference Example 1-3 (325 mg, 1.56 mmol), bis(tri-t-butyl-phosphine)palladium (20 mg, 0.039 mmol) and N,N-dicyclohexylmethylamine (409 mg, 2.1 mmol) in dioxane (1 ml) was stirred at 65° C. for 6 hours. To the reaction solution was added a 5% aqueous sodium thiosulfate solution, and the mixture was extracted with ethyl acetate. The organic layer was washed with water and saturated saline, dried over magnesium sulfate, and the solvent was evaporated under reduced pressure. The resulting residue was separated by silica gel column chromatography (hexane:ethyl acetate=10:1) to give the title compound (250 mg, 55%).

LC-MS (method A) r.t. 2.63 min., m/z 432 (M+1)

Example 1B

2-Methyl-2-[(3-{(1E)-3-[2-(4-methylbenzoyl)-1H-pyrrol-1-yl]prop-1-en-1-yl}-benzyl)oxy]propionic acid

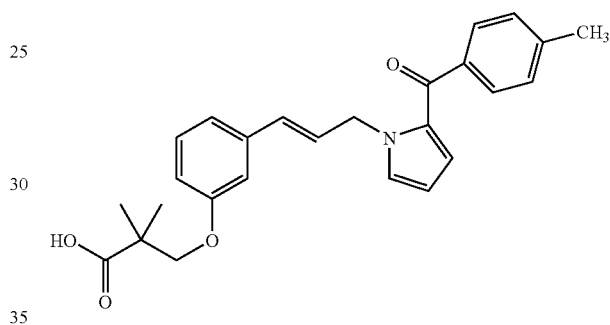

The compound of Example 1A-2 (242 mg) was dissolved in THF (1 ml), and to the resulting THF solution were added methanol (1 ml) and a 3N aqueous sodium hydroxide solution (1 ml), and the mixture was stirred at room temperature for 3 hours. The reaction solution was diluted with water, and washed with diethyl ether. To the aqueous layer was added a 5% aqueous potassium hydrogen sulfate solution to make it weakly acidic (pH 4), and the mixture was extracted with ethyl acetate. The organic layer was washed with a saturated saline, dried over magnesium sulfate, and concentrated under reduced pressure to give the title compound (195 mg, 80%).

$^1$H NMR (CDCl$_3$, 400 MHz) δ 7.73 (d, 2H, J=8.1 Hz), 7.35 (s, 1H), 7.29-7.24 (m, 5H), 7.05 (dd, 1H, J=2.4, 1.7 Hz), 6.77 (dd, 1H, J=4.0, 1.7 Hz), 6.51 (d, 1H, J=16.0 Hz), 6.45 (dt, 1H, J=16.0, 5.0 Hz), 6.21 (dd, 1H, J=4.0, 2.4 Hz), 5.20 (d, 2H, J=5.0 Hz), 4.49 (s, 2H), 2.42 (s, 3H), 1.56 (s, 6H)

LC-MS (Method A): r.t. 2.44 min., m/z 418 (M+1)

In a similar manner to Example 1A, 1B, the compounds of Example 2A, 2B to 10 were synthesized.

Example 2A

Methyl [(3-{(1E)-3-[2-(4-methylbenzoyl)-1H-pyrrol-1-yl]prop-1-en-1-yl}benzyl)-oxy](phenyl)acetate LC-MS (method A): r.t. 2.66 min., m/z 480 (M+1)

Example 2B

[(3-{(1E)-3-[2-(4-Methylbenzoyl)-1H-pyrrol-1-yl]prop-1-en-1-yl}benzyl)oxy]-(phenyl)acetic acid

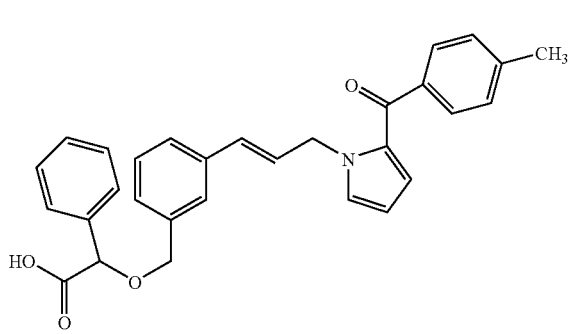

LC-MS (Method A): r.t. 2.56 min., m/z 466 (M+1)

Example 3A

Methyl 2-methyl-2-[(4-{(1E)-3-[2-(4-methylbenzoyl)-1H-pyrrol-1-yl]prop-1-en-1-yl}benzyl)oxy]propionate $^1$H NMR (CDCl$_3$, 400 MHz) δ 7.73 (d, 2H, J=8.0 Hz), 7.40-7.20 (m, 6H), 7.05 (dd, 1H, J=2.4, 1.7 Hz), 6.77 (dd, 1H, J=4.0, 1.7 Hz), 6.51 (d, 1H, J=16.0 Hz), 6.45 (dt, 1H, J=16.0, 5.0 Hz), 6.21 (dd, 1H, J=4.0, 2.4 Hz), 5.20 (d, 2H, J=5.0 Hz), 4.49 (s, 2H), 3.76 (s, 3H), 2.42 (s, 3H), 1.56 (s, 6H), LC-MS (method A): r.t. 2.71 min., m/z 432 (M+1)

Example 3B

2-Methyl-2-[(4-{(1E)-3-[2-(4-methylbenzoyl)-1H-pyrrol-1-yl]prop-1-en-1-yl}-benzyl)oxy]propionic acid

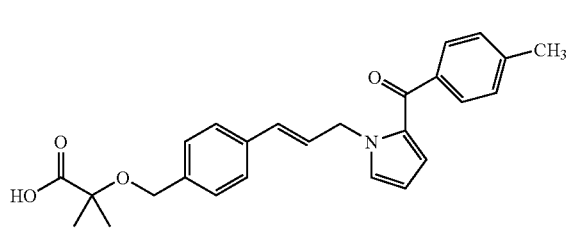

$^1$H NMR (CDCl$_3$, 400 MHz) δ 7.73 (d, 2H, J=8.0 Hz), 7.40-7.20 (m, 6H), 7.05 (dd, 1H, J=2.4, 1.7 Hz), 6.77 (dd, 1H, J=4.0, 1.7 Hz), 6.51 (d, 1H, J=16.0 Hz), 6.45 (dt, 1H, J=16.0, 5.0 Hz), 6.21 (dd, 1H, J=4.0, 2.4 Hz), 5.20 (d, 2H, J=5.0 Hz), 4.49 (s, 2H), 2.42 (s, 3H), 1.56 (s, 6H)

LC-MS (Method A): r.t. 2.53 min., m/z 418 (M+1)

Example 4

[(3-{(1E)-3-[2-(4-Methylbenzoyl)-1H-pyrrol-1-yl]prop-1-en-1-yl}benzyl)oxy]acetic acid

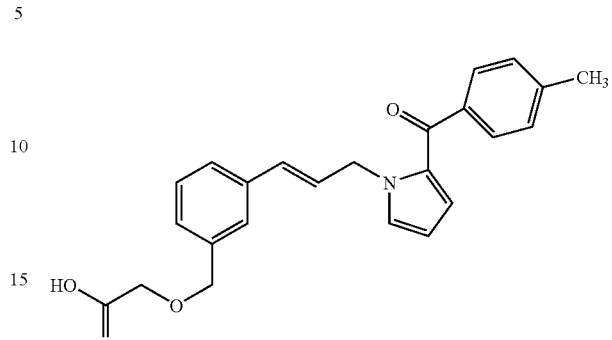

LC-MS (Method A): r.t. 2.35 min., m/z 390 (M+1)

Example 5A

Methyl (2R)-2-[(3-{(1E)-3-[2-(4-methylbenzoyl)-1H-pyrrol-1-yl]prop-1-en-1-yl}-benzyl)oxy]propionate LC-MS (method A): r.t. 2.54 min., m/z 418 (M+1)

Example 5B (2R)-2-[(3-{(1E)-3-[2-(4-Methylbenzoyl)-1H-pyrrol-1-yl]prop-1-en1-yl}benzyl)-oxy]propionic acid

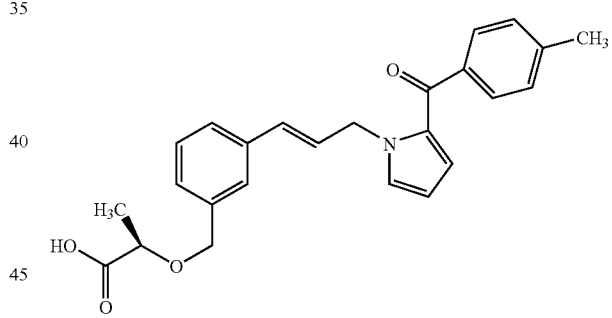

$^1$H NMR (CDCl$_3$, 400 MHz) δ 7.73 (d, 2H, J=8.1 Hz), 7.34-7.20 (m, 6H), 7.05 (dd, 1H, J=2.4, 1.7 Hz), 6.77 (dd, 1H, J=4.0, 1.7 Hz), 6.50 (d, 1H, J=16 Hz), 6.45 (dt, 1H, J=16, 4.8 Hz), 6.21 (dd, 1H, J=4.0, 2.4 Hz), 5.20 (d, 2H, J=4.8 Hz), 4.63 (d, 1H, J=11.5 Hz), 4.51 (d, 1H, J=11.5 Hz) 4.08 (q, 1H, J=6.8 Hz), 2.42 (s, 3H), 1.48 (d, 3H, J=6.8 Hz).

Example 6A

Methyl (2R)-2-[(4-{(1E)-3-[2-(4-methylbenzoyl)-1H-pyrrol-1-yl]prop-1-en-1-yl}-benzyl)oxy]propionate $^1$H NMR (CDCl$_3$, 400 MHz) δ 7.75 (d, 2H, J=8.1 Hz), 7.34 (d, 2H, J=8.1 Hz), 7.29-7.24 (m, 4H), 7.05 (dd, 1H, J=2.4, 1.7 Hz), 6.77 (dd, 1H, J=4.0, 1.7 Hz), 6.50 (d, 1H, J=16 Hz), 6.45(dt, 1H, J=4.8 Hz), 6.20 (dd, 1H, J=4.0, 2.4 Hz), 5.20 (d, 2H, J=4.8 Hz), 4.65(d, 1H, J=12 Hz), 4.42 (d, 1H, J=12 Hz) 4.08 (q, 1H, J=6.8 Hz), 3.75 (s, 3H), 2.42 (s, 3H), 1.46 (d, 3H, J=6.8 Hz)

Example 6B (2R)-2-[(4-{(1E)-3-[2-(4-Methylbenzoyl)-1H-pyrrol-1-yl]prop-1-ene-1-yl}benzyl)-oxy]propionic acid

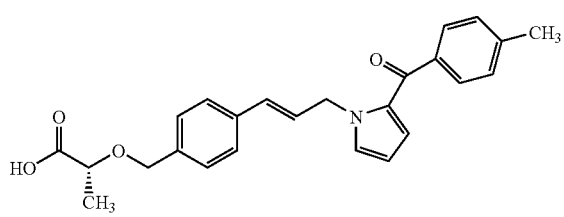

$^1$H NMR (CDCl$_3$, 400 MHz) δ 7.73 (d, 2H, J=8.1 Hz), 7.35 (d, 2H, J=8.2 Hz), 7.28 (d, 2H, J=8.2 Hz), 7.25 (d, 2H, J=8.1 Hz), 7.05 (dd, 1H, J=2.4, 1.7 Hz), 6.77 (dd, 1H, J=4.0, 1.7 Hz), 6.49 (d, 1H, J=16 Hz), 6.45 (dt, 1H, J=16, 4.9 Hz), 6.21 (dd, 1H, J=4.0, 2.4 Hz), 5.20 (d, 2H, J=4.9 Hz), 4.65 (d, 1H, J=11.7 Hz), 4.52 (d, 1H, J=11.7 Hz) 4.08 (q, 1H, J=6.8 Hz), 2.42 (s, 3H), 1.46 (d, 3H, J=6.8 Hz)

Example 7A

Methyl (2S)-2-[(3-{(1E)-3-[2-(4-methylbenzoyl)-1H-pyrrol-1-yl]prop-1-yl}benzyl)oxy]propionate LC-MS (method A): r.t. 2.54 min., m/z 418 (M+1)

Example 7B (2S)-2-[(3-{(1E)-3-[2-(4-Methylbenzoyl)-1H-pyrrol-1-yl]prop-1-en-1yl}benzyl)-oxy]propionic acid

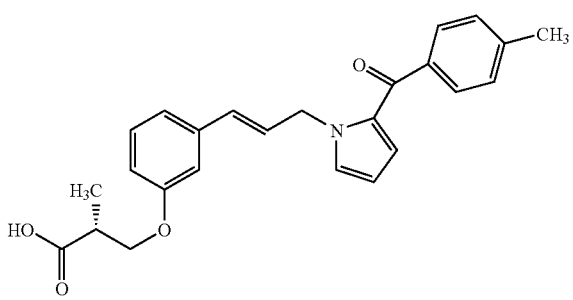

$^1$H NMR (CDCl$_3$, 400 MHz) δ 7.73 (d, 2H, J=8.1 Hz), 7.34-7.20 (m, 6H), 7.05 (dd, 1H, J=2.4, 1.7 Hz), 6.77 (dd, 1H, J=4.0, 1.7 Hz), 6.50 (d, 1H, J=16 Hz), 6.45 (dt, 1H, J=16, 4.8 Hz), 6.21 (dd, 1H, J=4.0, 2.4 Hz), 5.20 (d, 2H, J=4.8 Hz), 4.63 (d, 1H, J=11.5 Hz), 4.51 (d, 1H, J=11.5 Hz) 4.08 (q, 1H, J=6.8 Hz), 2.42 (s, 3H), 1.48 (d, 3H, J=6.8 Hz).

Example 8A

Methyl (2S)-2-[(4-{(1E)-3-[2-(4-methylbenzoyl)-1H-pyrrol-1-yl]prop-1-en-1-yl}benzyl)oxy]propionate $^1$H NMR (CDCl$_3$, 400 MHz) δ 7.75 (d, 2H, J=8.1 Hz), 7.34 (d, 2H, J=8.1 Hz), 7.29-7.24 (m, 4H), 7.05 (dd, 1H, J=2.4 Hz, 1.7 Hz), 6.77 (dd, 1H, J=4.0 Hz, 1.7 Hz), 6.50 (d, 1H, J=16 Hz), 6.45(dt, 1H, J=4.8 Hz), 6.20 (dd, 1H, J=4.0, 2.4 Hz), 5.20 (d, 2H, J=4.8 Hz), 4.65(d, 1H, J=12 Hz), 4.42 (d, 1H, J=12 Hz) 4.08 (q, 1H, J=6.8 Hz), 3.75 (s, 3H), 2.42 (s, 3H), 1.46 (d, 3H, J=6.8 Hz)

Example 8B (2S)-2-[(4-{(1E)-3-[2-(4-Methylbenzoyl)-1H-pyrrol-1-yl]prop-1-en-1yl}benzyl)-oxy]propionic acid

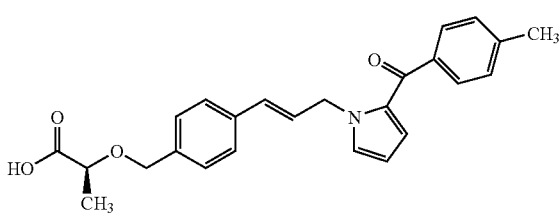

$^1$H NMR (CDCl$_3$, 400 MHz) δ 7.73 (d, 2H, J=8.1 Hz), 7.35 (d, 2H, J=8.2 Hz), 7.28 (d, 2H, J=8.2 Hz), 7.25 (d, 2H, J=8.1 Hz), 7.05 (dd, 1H, J=2.4, 1.7 Hz), 6.77 (dd, 1H, J=4.0, 1.7 Hz), 6.49 (d, 1H, J=16 Hz), 6.45 (dt, 1H, J=16, 4.9 Hz), 6.21 (dd, 1H, J=4.0, 2.4 Hz), 5.20 (d, 2H, J=4.9 Hz), 4.65 (d, 1H, J=11.7 Hz), 4.52 (d, 1H, J=11.7 Hz) 4.08 (q, 1H, J=6.8 Hz),- 2.42 (s, 3H), 1.46 (d, 3H, J=6.8 Hz)

Example 9A

Ethyl 2-[(3-{(1E)-3-[2-(4-methylbenzoyl)-1H-pyrrol-1-yl]prop-1-en-1-yl}benzyl)-oxy]butyrate LC-MS (method A): r.t. 2.69 min., m/z 446 (M+1)

Example 9B

2-[(3-{(1E)-3-[2-(4-methylbenzoyl)-1H-pyrrol-1-yl]prop-1-en-1-yl}benzyl)oxy]-butyric acid

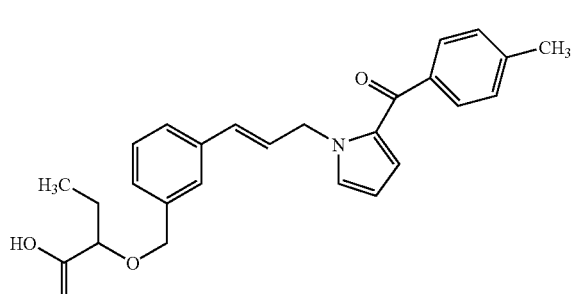

LC-MS (Method A): r.t. 2.43 min., m/z 418 (M+1)

Example 10

1-[(3-{(1E)-3-[2-(4-Methylbenzoyl)-1H-pyrrol-1-yl]-prop-1-en-1yl}-benzyloxy)]-cyclobutyric acid

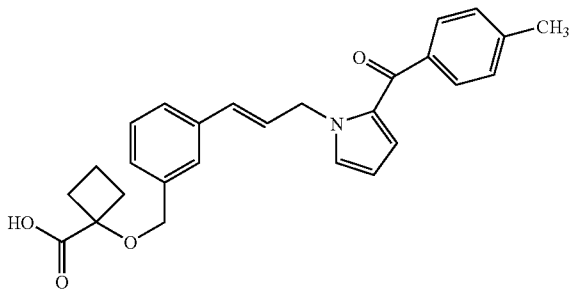

LC-MS (Method A): r.t. 2.51 min., m/z 430 (M+1)

Example 11

(2S)-2-[(4-{(1E)-3-[2-(4-Methylbenzoyl)-1H-pyrrol-1-yl]prop-1-en-1-yl}benzyl)-oxy]propionic acid 1,3-dihydroxy-2-(hydroxymethyl)propan-2-aminium salt

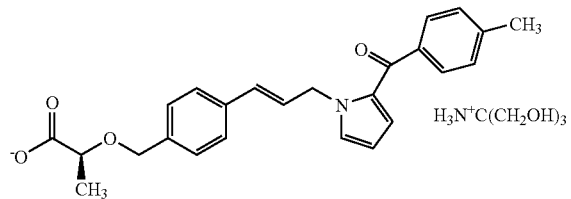

To a solution of the compound of Example 8B (400 mg, 0.99 mmol) in isopropanol (5 ml) was added tris(hydroxymethyl)aminomethane (120 mg, 0.99 mmol), and the mixture was stirred at 70° C. for one hour. This mixture was cooled to room temperature over a period of 6 hours for crystallization to give white crystals. The obtained crystals were collected by filtration to give the title compound (200 mg, 39%).

$^1$H NMR (DMSO-$d_6$, 400 MHz) δ 7.66 (d, 2H, J=8.1 Hz), 7.37 (dd, 1H, J=2.5, 1.7 Hz), 7.34 (d, 2H, J=8.2 Hz), 7.31 (d, 2H, J=8.1 Hz), 7.25 (d, 2H, J=8.2 Hz), 6.69 (dd, 1H, J=4.0, 1.7 Hz), 6.47 (dt, 1H, J=15.9, 5.5 Hz), 6.38 (d, 1H, J=15.9 Hz), 6.23 (dd, 1H, J=4.0, 2.5 Hz), 5.16 (brd, 2H, J=5.5 Hz), 4.57 (d, 1H, J=12.0 Hz), 4.27 (d, 1H, J=12.0 Hz), 3.72 (q, 1H, J=6.8 Hz), 3.39 (s, 6 H), 2.43 (s, 3H), 1.21 (d, 3H, J=6.8 Hz)

Results of Analysis: 99.5% ee.

(Conditions for resolution: 20.4 min; Conditions for HPLC: Column, CHIRALCEL OD-RH (5 μm, 6 mmΦ×15 cm), Solvent for elution: Solution A, 0.1% trifluoroacetic acid/water, Solution B, acetonitrile, Solution A: Solution B=1:1 (constant), Flow rate: 1 ml/min), UV: 254 nm)

Example 12

(2R)-2-[(4-{(1E)-3-[2-(4-Methylbenzoyl)-1H-pyrrol-1-yl]prop-1-en-1yl}benzyl)-oxy]propionic acid 1,3-dihydroxy-2-(hydroxymethyl)propan-2-aminium salt

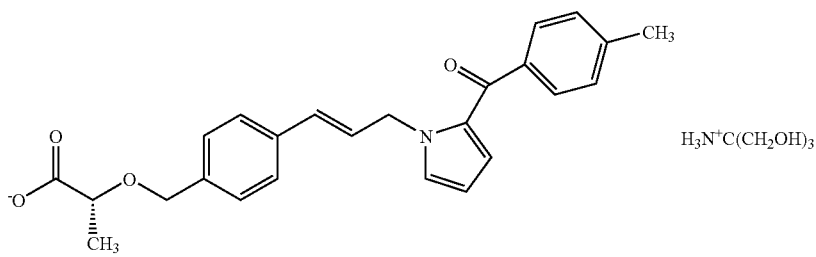

Using the compound of Example 6B, the title compound was synthesized in a similar manner to Example 11.

$^1$H NMR (DMSO-$d_6$, 400 MHz) δ 7.66 (d, 2H, J=8.1 Hz), 7.37 (dd, 1H, J=2.5, 1.7 Hz), 7.34 (d, 2H, J=8.2 Hz), 7.31 (d, 2H, J=8.1 Hz), 7.25 (d, 2H, J=8.2 Hz), 6.69 (dd, 1H, J=4.0, 1.7 Hz), 6.47 (dt, 1H, J=15.9, 5.5 Hz), 6.38 (d, 1H, J=15.9 Hz), 6.23 (dd, 1H, J=4.0, 2.5 Hz), 5.16 (brd, 2H, J=5.5 Hz), 4.57 (d, 1H, J=12.0 Hz), 4.27 (d, 1H, J=12.0 Hz), 3.72 (q, 1H, J=6.8 Hz), 3.39 (s, 6 H), 2.43 (s, 3H), 1.21 (d, 3H, J=6.8 Hz)

Results of Analysis: optical purity, 99.5% ee.

(Conditions for resolution: 24.7 min, Conditions for HPLC: Column: CHIRALCEL OD-RH (5 μm, 6 mmΦ×15 cm), elution solvent: Solution A, 0.1% trifluoroacetic acid/water, Solution B, acetonitrile, Solution A:Solution B=1:1 (constant), Flow rate: 1 ml/min, UV: 254 nm)

Example 13

(2R)-2-[(4-{3-[2-(4-Methylbenzoyl)-1H-pyrrol-1-yl]propyl}benzyl)oxy]propionic acid

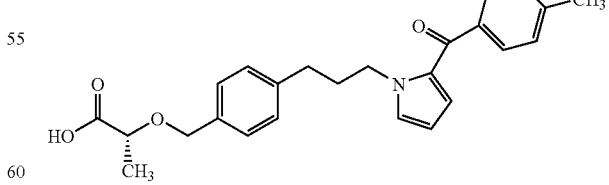

The compound of Example 6B (200 mg, 0.496 mmol) was dissolved in methanol (4 ml), and thereto was added a 10% palladium-carbon (50% wet, 20 mg), and the mixture was stirred at room temperature under atmospheric pressure of hydrogen for 3 hours. The mixture was filtered, and the filtrate was concentrated under reduced pressure to give the title compound (200 mg, 99%).

¹H NMR (CDCl₃, 400 MHz) δ 7.70 (d, 2H, J=8.1 Hz), 7.28-7.23 (m, 4H), 7.17 (d, 2H, J=8.1 Hz), 6.95 (dd, 1H, J=2.4, 1.7 Hz), 6.73 (dd, 1H, J=4.0, 1.7 Hz), 6.16 (dd, 1H, J=4.0, 2.4 Hz), 4.60 (d, 2H, J=11 Hz), 4.40(t, 2H, J=7.2 Hz), 4.06(q, 1H, J=7.0 Hz), 2.63 (t, 1H, J=7.5 Hz), 2.42 (s, 3H), 2.11 (dt, 2H, J=7.2, 7.5 Hz), 1.45 (d, 3H, J=7.0 Hz)

LC-MS (method A): r.t. 2.42 min., m/z 406 (M+1)

Example 14

2-[(6-{2-[2-(4-Methylbenzoyl)-1H-pyrrol-1-yl]ethoxy}pyridin-3-yl)methoxy]-propionic acid

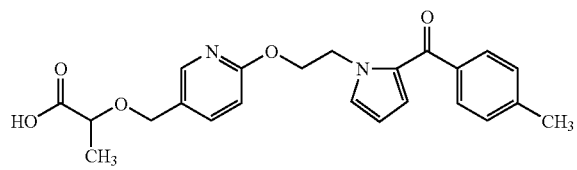

To a solution of the compound of Reference Example 36 (86 mg, 0.256 mmol) in THF (6 ml) were added under ice-cooling triethylamine (33 mg, 0.326 mmol) and methanesulfonyl chloride (38 mg, 0.332 mmol), and the reaction solution was stirred at 0° C. for 20 minutes. The reaction solution was filtered, and the insoluble materials were removed to give Filtrate A.

Separately, to a suspension of sodium hydride (60% in parafin liquid) (30 mg, 0.75 mmol) in DMF (4 ml) was added a solution of ethyl (±)-lactate (80 mg, 0.677 mmol) in DMF (1 ml) under ice-cooling, and the reaction solution was stirred at room temperature for 30 minutes. Under ice-cooling, to the reaction solution was added dropwise the above Filtrate A, and the reaction mixture was stirred at room temperature for one and half hour. To the reaction solution was added a saturated aqueous sodium hydrogen carbonate solution, and the mixture was extracted with ethyl acetate. The organic layer was washed with water and saturated saline, dried over magnesium sulfate, and the solvent was evaporated under reduced pressure. The residue was purified by silica gel column chromatography (hexane:ethyl acetate=3:2→2:3) to give a mixture of the ethyl ester compound of the title compound (7 mg).

The resulting mixture of the ethyl ester compound (7 mg) was dissolved in THF (2 ml), and thereto were added a 2N aqueous lithium hydroxide solution (2 ml) and methanol (2 ml), and the reaction solution was stirred at room temperature for one hour. The reaction solution was diluted with water and washed with diethyl ether. The pH value of the aqueous layer was adjusted to around pH 6 with a 5% aqueous potassium hydrogen sulfate solution and a saturated aqueous sodium hydrogen carbonate solution, and the mixture was extracted with ethyl acetate. The organic layer was washed with water and saturated saline, dried over magnesium sulfate and the solvent was evaporated under reduced pressure to give the title compound (5.5 mg, Yield for 2 steps: 5%).

¹H-NMR (400 MHz in CDCl₃) δ 8.09 (d, 1H, J=2.4 Hz), 7.71 (d, 2H, J=8.1 Hz), 7.60 (dd, 1H, J=8.5, 2.4 Hz), 7.25 (d, 2H, J=8.1 Hz), 7.03 (dd, 1H, J=2.5, 1.7 Hz), 6.75 (dd, 1H, J=4.0, 1.7 Hz), 6.69 (d, 1H, J=8.5 Hz), 6.15 (dd, 1H, J=4.0, 2.5 Hz), 4.77-4.84 (m,2H), 4.64-4.71 (m, 2H), 4.59 (d, 1H, J=11.3 Hz), 4.47 (d, 1H, J=11.3 Hz), 4.09 (q, 1H, J=6.9 Hz), 2.42 (s,3H,), 1.48 (d, 3H, J=6.9 Hz).

Using the compounds of Reference Example 33-2, 34-2, the compounds of Example 1A, 1B to 10, 16 to 19 can be synthesized in a similar manner to Example 14.

Example 15

(2S)-2-[(4-{(1E)-3-[2-(4-Methylbenzoyl)-1H-pyrrol-1-yl]prop-1-en-1-yl}benzoyl)oxy]-N-(methylsulfonyl)propanamide

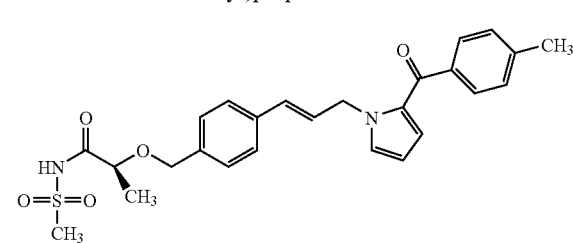

The compound of Example 8 (500 mg, 1.24 mmol) was stirred at 90° C. in a solution 1,1-carbonylbis-1H-imidazole (302 mg, 1.86 mmol), methanesulfonyl-amide (130 mg, 1.36 mmol) and 1.8-diazabicyclo[5,4,0]undeca-7-ene (283 mg, 1.86 mmol) in DMF for 2 hours. Water was added to the reaction solution, and the mixture was extracted with ethyl acetate. The organic layer was washed with water and saturated saline, dried over magnesium sulfate, and the solvent was evaporated under reduced pressure. The resulting residue was separated by silica gel column chromatography (chloroform: methanol=20: 1) to give the title compound (210 mg, 35%).

LC-MS (method B): r.t. 3.98 min., m/z 481(M+1)

The compounds of Examples 16 to 54 were synthesized in a similar manner to Examples 1A and 1B.

TABLE 7

| Ex. No. | Structure | ¹H-NMR Data, LC-MC data |
|---|---|---|
| 16 | ![structure] | LC-MS (method B): r.t. 4.82 min., m/z 446(M + 1) |

TABLE 7-continued

| Ex. No. | Structure | ¹H-NMR Data, LC-MC data |
|---|---|---|
| 17 | 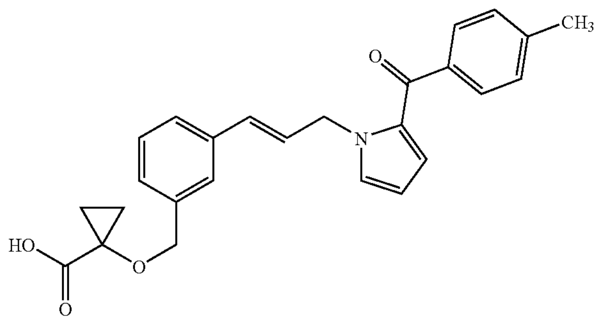 | ¹H NMR (CDCl3, 400 MHz) δ 7.74 (d, 2H, J=8.1 Hz), 7.34-7.20 (m, 6H), 7.05 (dd, 1H, J= 2.4, 1.7 Hz), 6.77 (dd, 1H, J= 4.0, 1.7 Hz), 6.47 (dt, 2H, J= 16, 4.8 Hz), 6.21 (dd, 1H, J= 4.0, 2.4 Hz), 5.20 (d, 2H, J= 4.8 Hz), 4.64 (s, 2H), 2.41 (s, 3H), 1.45-1.42(m, 2H), 1.33-1.29(m, 2H), LC-MS (method B): r.t. 4.51 min., m/z 416 (M + 1) |
| 18 | 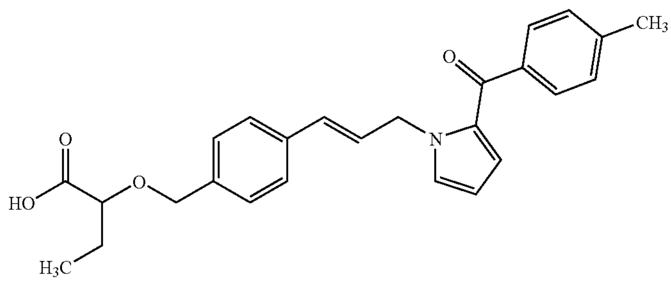 | LC-MS (method B): r.t. 4.55 min., m/z 418 (M + 1) |
| 19 | 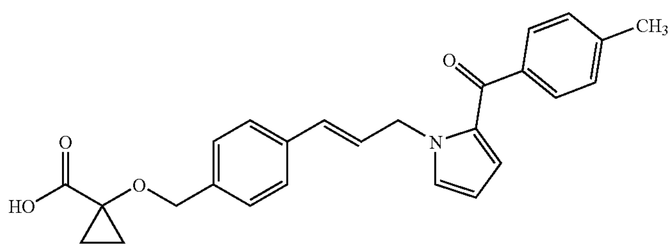 | LC-MS (method B): r.t. 4.49 min., m/z 416 (M + 1) |
| 20 | 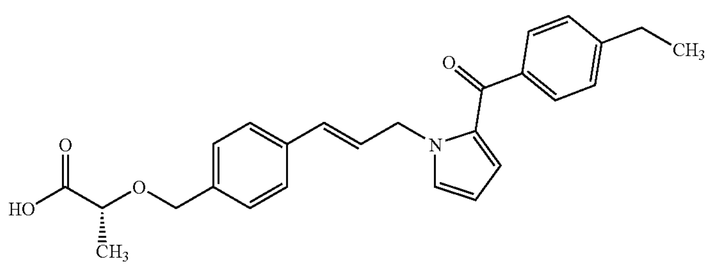 | LC-MS (method B): r.t. 4.59 min., m/z 418 (M + 1) |

TABLE 8

| Ex. No. | Structure | ¹H-NMR Data, LC-MC data |
|---|---|---|
| 21 | 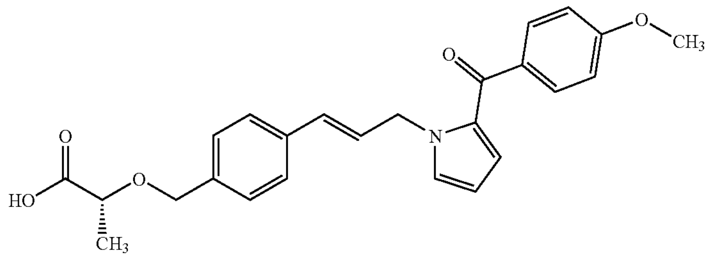 | LC-MS (method B): r.t. 4.24 min., m/z 420 (M + 1) |
| 22 | 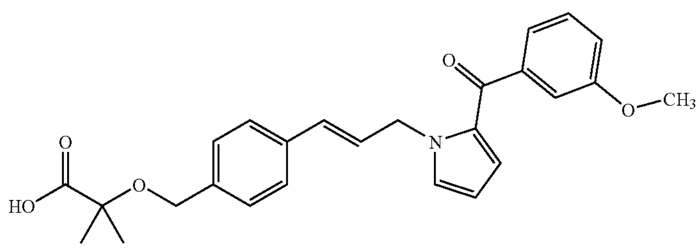 | LC-MS (method B): r.t. 4.43 min., m/z 434 (M + 1) |
| 23 | 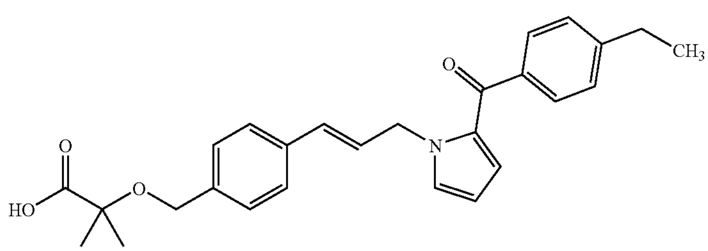 | ¹H NMR (CDCl₃, 400 MHz) δ 7.75 (d, 2H, J=8.2 Hz), 7.35 (d, 2H, J=8.2 Hz), 7.27 (d, 4H, J=8.1 Hz), 7.05 (dd, 1H, J=2.4, 1.7 Hz), 6.77 (dd, 1H, J=4.0, 1.7 Hz), 6.48 (dt, 2H, J=16, 5.0 Hz), 6.21 (dd, 1H, J =4.0, 2.4 Hz), 5.20 (d, 2H, J=5.0 Hz), 4.49 (s, 2H), 2.72 (q, 2H, J=7.6 Hz), 1.51 (s, 6H), 1.28 (t, 3H, J= 7.6 Hz), LC-MS (method B): r.t. 4.72 min., m/z 432 (M + 1) |
| 24 | 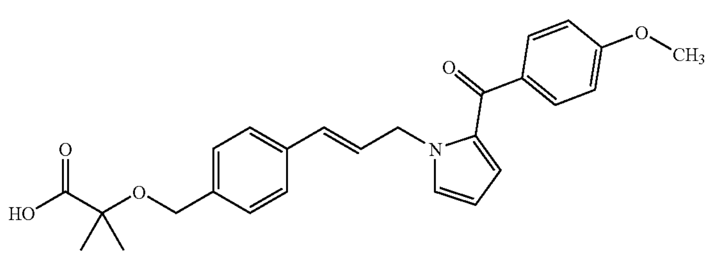 | LC-MS (method B): r.t. 4.38 min., m/z 434 (M + 1) |
| 25 | 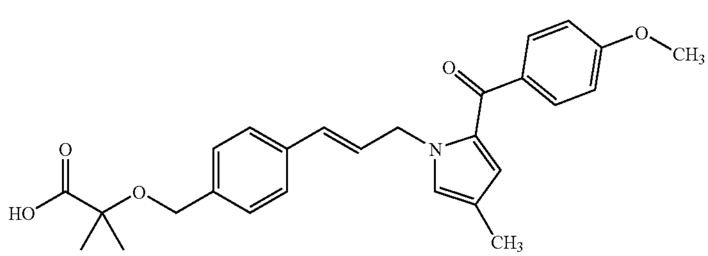 | ¹H NMR (CDCl₃, 400 MHz) δ 7.83 (d, 2H, J=8.8 Hz), 7.34 (d, 2H, J=8.2 Hz), 7.27 (d, 2H, J=8.2 Hz), 6.94 (d, 2H, J=8.8 Hz), 6.83 (s, 1H) , 6.50 (s, 1H) , 6.43 (dt, 2H, J=16, 5.5 Hz), 5.12 (d, 2H, J =5.5 Hz), 4.48 (s, 2H), 3.87 (s, 3H), 2.09 (s, 3H), 1.54 (s, 6H), LC-MS (method B): r.t. 4.53 min., m/z 448 (M + 1) |

TABLE 9

| Ex. No. | Structure | ¹H-NMR Data, LC-MC data |
|---|---|---|
| 26 | (structure) | LC-MS (method B): r.t. 4.72 min., m/z 432 (M + 1) |
| 27 | (structure) | ¹H NMR (CDCl3, 400 MHz) δ 8.17 (d, 2H, J=8.2 Hz), 7.36 (d, 2H, J=8.2 Hz), 7.28 (d, 2H, J=8.2 Hz), 7.27-7.26 (m, 3H), 7.22(s, 1H), 6.55 (a, 1H, J= 16 Hz), 6.43 (dt, 1H, J=16, 6.2 Hz), 5.23 (d, 2H, J= 6.2 Hz), 4.61 (d, 1H, J=11 Hz), 4.53 (d, 1H, J=11 Hz), 4.07 (q, 1H, J =6.9 Hz), 2.42 (s, 3H), 1.46 (a, 3H, J=6.9 Hz), LC-MS (method B) r.t. 3.74 min., m/z 405 (M + 1) |
| 28 | (structure) | LC-MS (method B) r.t. 3.90 min., m/z 419 (M + 1) |
| 29 | (structure) | ¹H NMR (CDCl3, 400 MHz) δ 8.32 (d, 2H, J =9.0 Hz), 7.36 (d, 2H, J=8.2 Hz), 7.29 (d, 2H, J=8.2 Hz), 7.26 (s, 1H), 7.21 (s, 1H), 6.97 (d, 2H, J= 9.0 Hz), 6.56 (d, 1H, J= 16 Hz), 6.43 (dt, 1H, J=16, 6.2 Hz), 5.20 (d, 2H, J=6.2 Hz), 4.65 (d, 1H, J =11 Hz), 4.51 (d, 1H, J=11 Hz), 4.08 (q, 1H, J=6.9 Hz), 3.87 (s, 3H), 1.46 (d, 3H, J=6.9 Hz), LC-MS (method B): r.t. 3.57 min., m/z 421 (M + 1) |

TABLE 10

| Ex. No. | Structure | ¹H-NMR Data, LC-MC data |
|---|---|---|
| 30 | 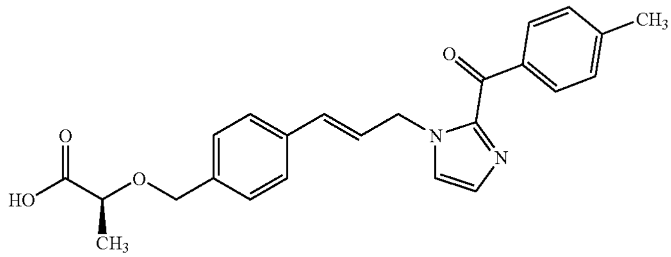 | ¹H NMR (CDC13, 400 MHz) δ 8.17 (d, 2H, J=8.2 Hz), 7.36 (d, 2H, J=8.2 Hz), 7.28 (d, 2H, J=8.2 Hz), 7.27-7.26 (m, 3H), 7.22(s, 1H), 6.55 (d, 1H, J=16 Hz), 6.43 (dt, 1H, J=16, 6.2 Hz), 5.23 (d, 2H, J=6.2 Hz), 4.61 (d, 1H, J=11 Hz), 4.53 (d, 1H, J=11 Hz), 4.07 (q, 1H, J=6.9 Hz), 2.42 (s, 3H), 1.46 (d, 3H, J=6.9 Hz), LC-MS (method B) r.t. 3.74 min., m/z 405 (M + 1) |
| 31 | 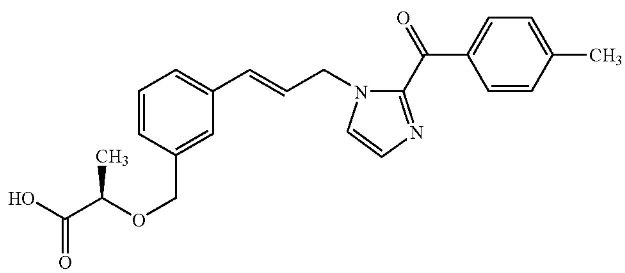 | LC-MS (method B): r.t. 3.78 min., m/z 405 (M + 1) |
| 32 | 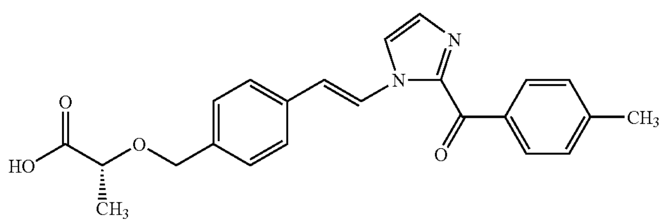 | LC-MS (method B): r.t. 4.07 min., m/z 391 (M + 1) |
| 33 | 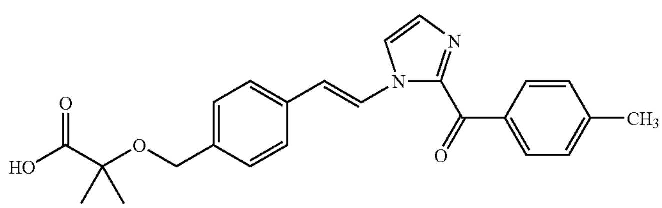 | LC-MS (method B): r.t. 4.22 min., m/z 405 (M + 1) |
| 34 | 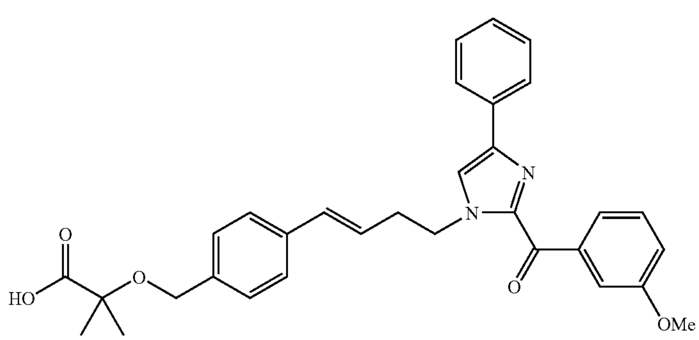 | LC-MS (method B): r.t. 4.80 min., m/z 525 (M + 1) |

TABLE 10-continued

| Ex. No. | Structure | ¹H-NMR Data, LC-MC data |
|---|---|---|
| 35 | 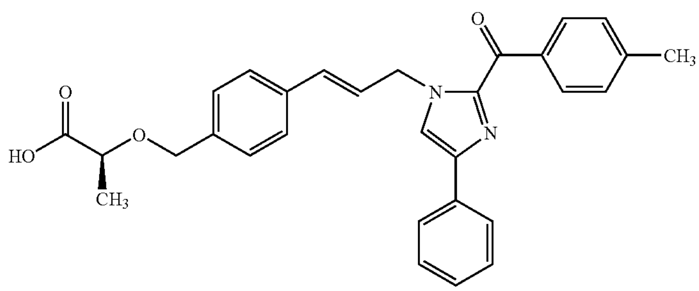 | LC-MS (method B): r.t. 4.72 min., m/z 481 (M + 1) |

TABLE 11

| Ex. No. | Structure | ¹H-NMR Data, LC-MC data |
|---|---|---|
| 36 | 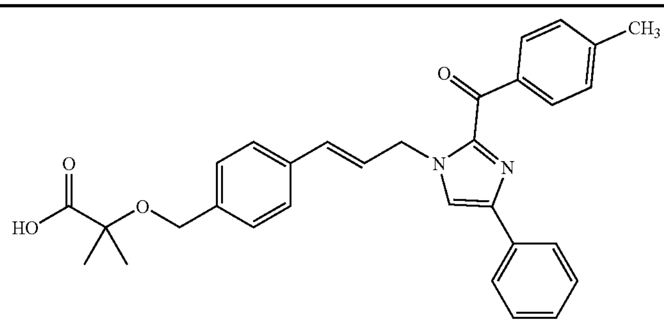 | ¹H NMR (CDCl3, 400 MHz) δ 8.36(d, 2H, J=8.2 Hz), 7.84 (d, 2H, J=8.2 Hz), 7.51 (s, 1H), 7.41-7.26 (m, 9H), 6.61 (d, 1H, J= 16 Hz), 6.46 (dt, 1H, J=16, 6.2 Hz), 5.27 (d, 2H, J= 6.2 Hz), 4.50 (s, 2H), 2.45 (s, 3H), 1.55 (s, 6H), LC-MS (method B): r.t. 4.88 min., m/z 495 (M + 1) |
| 37 | 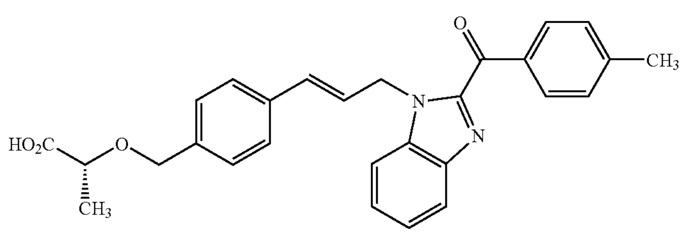 | LC-MS (method B) r.t. 4.36 min., m/z 455 (M + 1) |
| 38 | 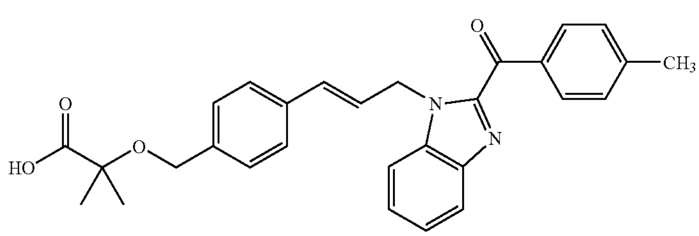 | LC-MS (method B): r.t. 4.53 min., m/z 469 (M + 1) |
| 39 | 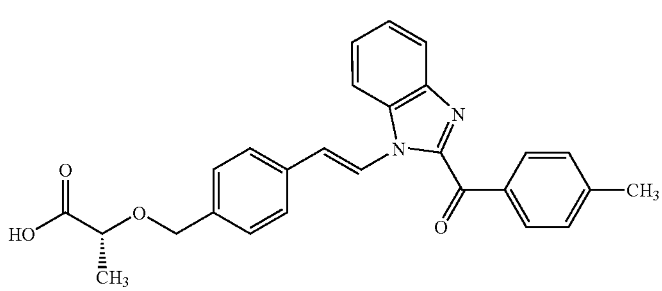 | LC-MS (method B): r.t. 4.30 min., m/z 441 (M + 1) |

TABLE 11-continued

| Ex. No. | Structure | ¹H-NMR Data, LC-MC data |
|---|---|---|
| 40 | 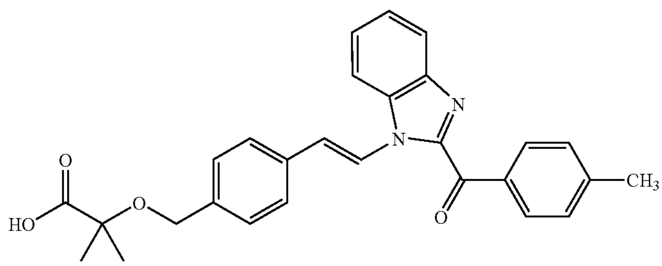 | LC-MS (method B): r.t. 4.66 min., m/z 455 (M + 1) |

TABLE 12

| Ex. No. | Structure | ¹H-NMR Data, LC-MC data |
|---|---|---|
| 41 | 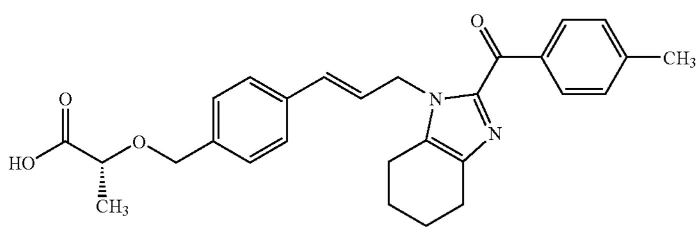 | LC-MS (method B) r.t. 3.72 min., m/z 459 (M + 1) |
| 42 | 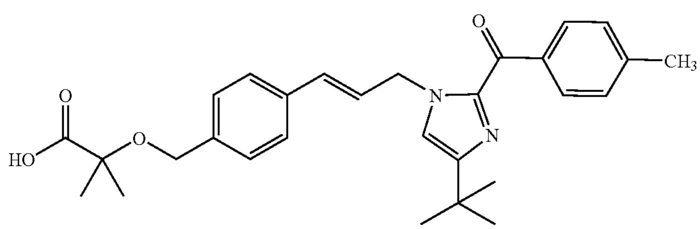 | LC-MS (method B): r.t. 4.36 min., m/z 475 (M + 1) |
| 43 | 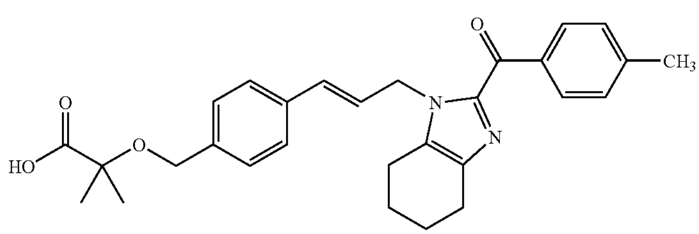 | LC-MS (method B): r.t. 3.80 min., m/z 473 (M + 1) |
| 44 | 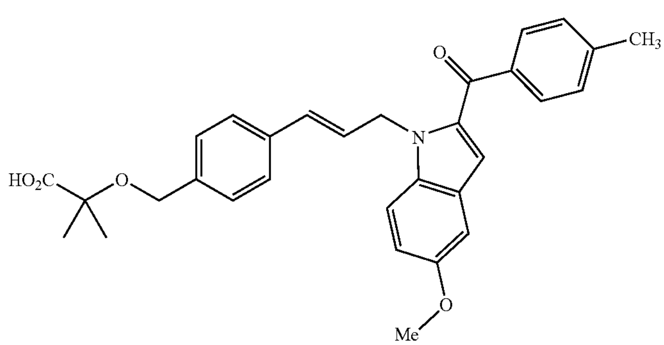 | LC-MS (method B): r.t. 4.35 min., m/z 498 (M + 1) |

TABLE 12-continued

| Ex. No. | Structure | ¹H-NMR Data, LC-MC data |
|---|---|---|
| 45 | 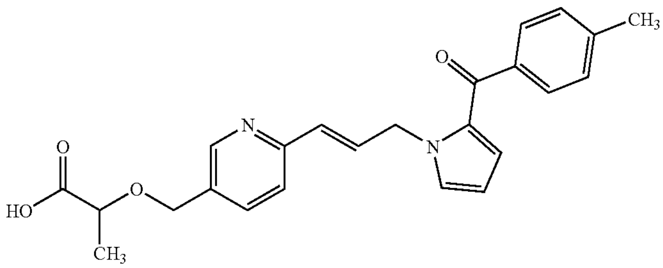 | LC-MS (method B): r.t. 3.32 min., m/z 405 (M + 1) |

TABLE 13

| Ex. No. | Structure | ¹H-NMR Data, LC-MC data |
|---|---|---|
| 46 | 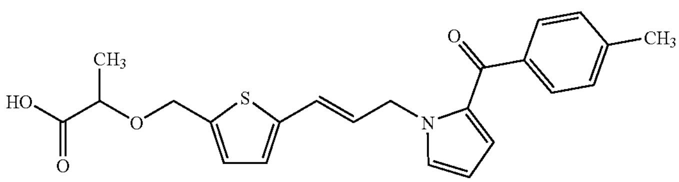 | LC-MS (method B): r.t. 4.28 min., m/z 410 (M + 1) |
| 47 | 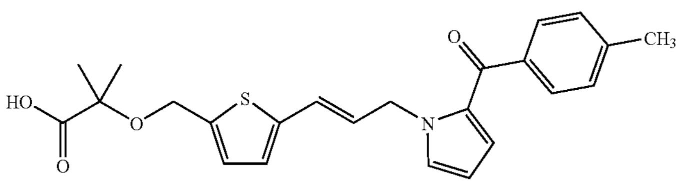 | LC-MS (method B): r.t. 4.30 min., m/z 424 (M + 1) |
| 48 | 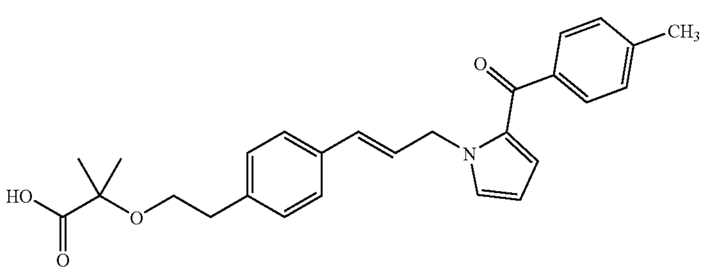 | LC-MS (method B): r.t. 4.05 min., m/z 432 (M + 1) |
| 49 | 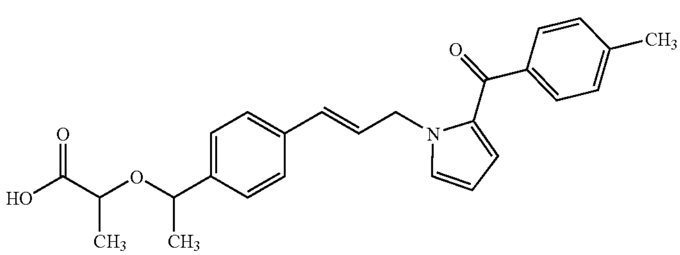 | LC-MS (method B): r.t. 3.97 min., m/z 418 (M + 1) |

TABLE 13-continued

| Ex. No. | Structure | ¹H-NMR Data, LC-MC data |
|---|---|---|
| 50 | 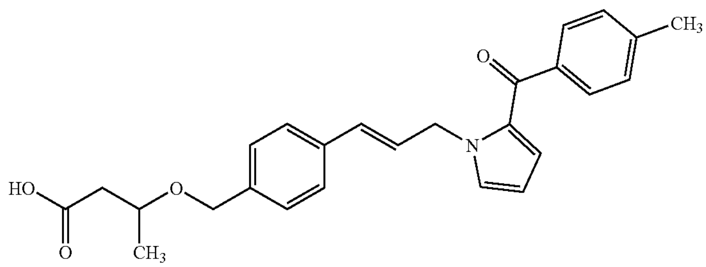 | LC-MS (method B): r.t. 4.01 min., m/z 418 (M + 1) |

TABLE 14

| Ex. No. | Structure | ¹H-NMR Data, LC-MC data |
|---|---|---|
| 51 | 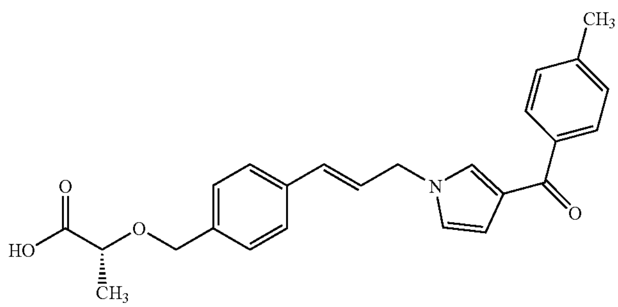 | LC-MS (method B): r.t. 3.57 min., m/z 404 (M + 1) |
| 52 | 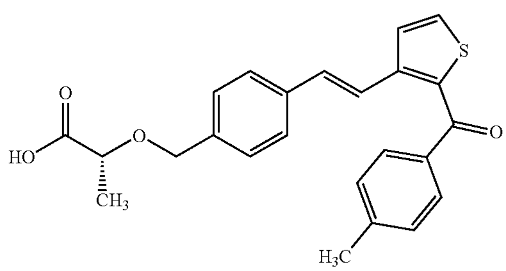 | LC-MS (method B): r.t. 3.95 min., m/z 407 (M + 1) |
| 53 | 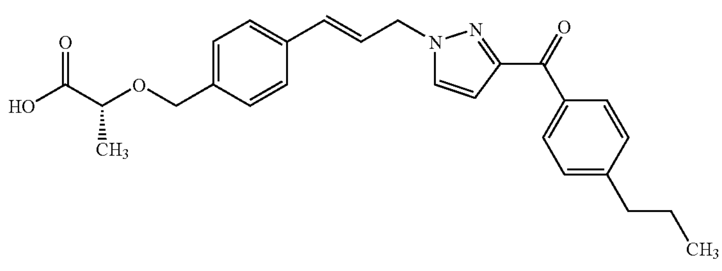 | LC-MS (method B): r.t. 4.49 min., m/z 433 (M + 1) |
| 54 | 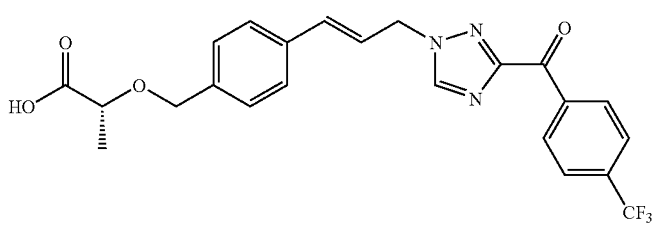 | LC-MS (method B): r.t. 4.09 min., m/z 460 (M + 1) |

The compounds of Examples 55-64 were synthesized in a similar manner to Example 13.
TABLE 15
| Ex. No. | Structure | ¹H-NMR Data, LC-MC data |
|---|---|---|
| 55 | 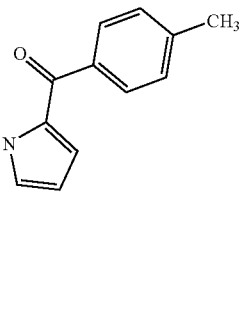 | LC-MS (method B): r.t. 4.45 min., m/z 406 (M + 1) |
| 56 | 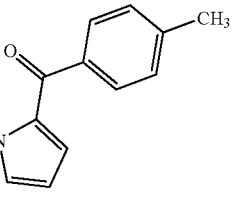 | ¹H NMR (CDCl₃, 400 MHz) δ 7.70 (d, 2H, J=8.1 Hz), 7.28-7.23 (m, 4H), 7.17 (d, 2H, J=8.1 Hz),, 7.05 (dd, 1H, J=2.4, 1.7 Hz), 6.73 (dd, 1H, J=4.0, 1.7 Hz), 6.15 (dd, 1H, J=4.0, 2.4 Hz), 4.48 (s, 2H), 4.39 (t, 2H, J=7.2 Hz), 2.65 (t, 2H, J=7.5 Hz), 2.42 (s, 3H), 2.19-2.10 (m, 2H), 1.54 (s, 6H), LC-MS (method B): r.t. 4.61 min., m/z 420 (M + 1) |
| 57 | 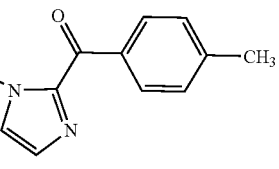 | LC-MS (method B): r.t. 3.72 min., m/z 407 (M + 1) |
| 58 | 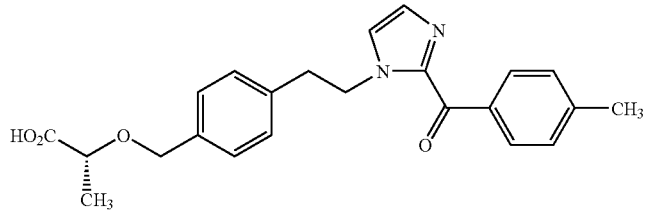 | LC-MS (method B): r.t. 3.51 min., m/z 393 (M + 1) |
| 59 | 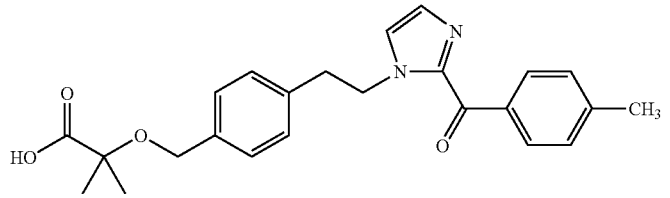 | LC-MS (method B): r.t. 3.65 min., m/z 407 (M + 1) |

TABLE 16

| Ex. No. | Structure | ¹H-NMR Data, LC-MC data |
|---|---|---|
| 60 | 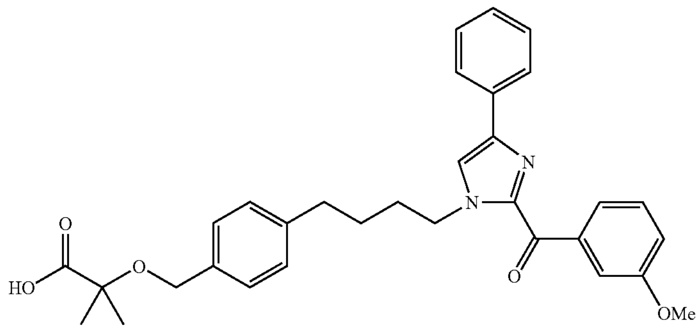 | LC-MS (method B): r.t. 4.88 min., m/z 527 (M + 1) |
| 61 | 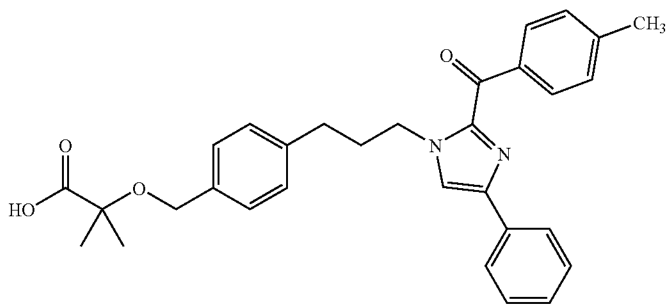 | LC-MS (method B): r.t. 4.88 min., m/z 497 (M + 1) |
| 62 | 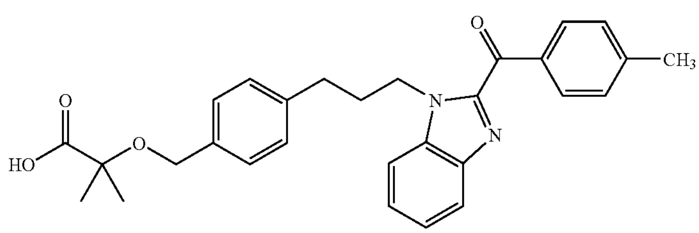 | LC-MS (method B): r.t. 4.55 min., m/z 471 (M + 1) |
| 63 | 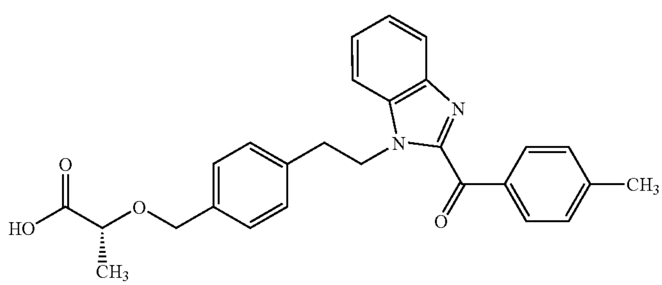 | LC-MS (method B): r.t. 4.22 min., m/z 443 (M + 1) |
| 64 | 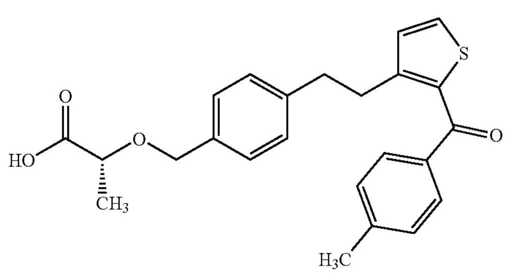 | LC-MS (method B): r.t. 3.95 min., m/z 409 (M + 1) |

The compounds of Examples 65-66 were synthesized in a similar manner to Example 14.

TABLE 17

| Ex. No. | Structure | ¹H-NMR Data, LC-MC data |
|---|---|---|
| 65 | 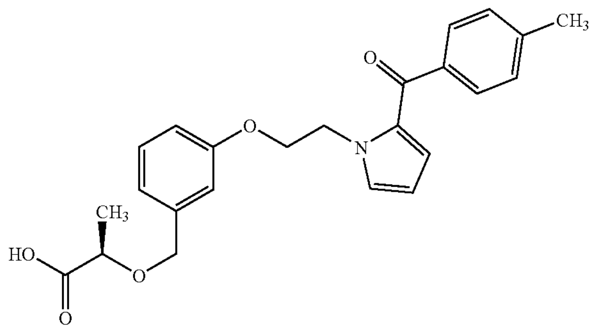 | ¹H NMR (CDCl₃, 400 MHz) δ 7.70 (d, 2H, J=8.1 Hz), 7.26-7.25 (m, 3H), 7.14 (dd, 1H, J=2.4, 1.7 Hz), 6.93-6.89 (m, 2H), 6.77 (dd, 1H, J=7.5, 1.8 Hz), 6.77 (dd, 1H, J=4.0, 1.7 Hz), 6.18 (dd, 1H, J=4.0, 2.4 Hz), 4.77 (t, 2H, J=5.1 Hz), 4.57 (d, 1H, J=12 Hz), 4.54 (d, 1H, J=12 Hz), 4.37 (t, 2H, J=5.1 Hz), 4.07 (q, 1H, J=6.9 Hz), 2.42 (s, 3H), 1.47 (d, 3H, J=6.9 Hz), LC-MS (method B): r.t. 4.30 min., m/z 408 (M + 1) |
| 66 | 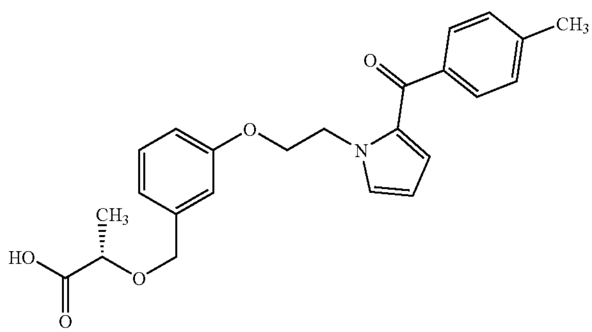 | ¹H NMR (CDCl₃, 400 MHz) δ 7.70 (d, 2H, J=8.1 Hz), 7.26-7.25 (m, 3H), 7.14 (dd, 1H, J=2.4, 1.7 Hz), 6.93-6.89 (m, 2H), 6.77 (dd, 1H, J=7.5, 1.8 Hz), 6.77 (dd, 1H, J=4.0, 1.7 Hz), 6.18 (dd, 1H, J=4.0, 2.4 Hz), 4.77 (t, 2H, J=5.1 Hz), 4.57 (d, 1H, J=12 Hz), 4.54 (d, 1H, J=12 Hz), 4.37 (t, 2H, J=5.1 Hz), 4.07 (q, 1H, J=6.9 Hz), 2.42 (s, 3H), 1.47 (d, 3H, J=6.9 Hz), LC-MS (method B): r.t. 4.30 min., m/z 408 (M + 1) |

Example 67

2-Methyl-2-[(4-{(1E)-2-methyl-3-[2-(4-methylbenzoyl)-1H-pyrrol-1-yl]prop-1-yl}benzyl)oxy]propionic acid

Example 67-1

(4-Methylphenyl)[1-(2-methylprop-2-en-1-yl)-1H-pyrrol-2-yl]methanone

The title compound was synthesized in a similar manner to Reference Example 1-3.

¹H NMR (CDCl₃, 400 MHz) δ 7.71 (d, 2 H, J=8.0 Hz), 7.24 (d, 2 H, J=8.0 Hz), 6.96 (dd, 1 H, J=2.5, 1.7 Hz), 6.73 (dd, 1 H, J=4.0, 1.7 Hz), 6.19 (dd, 1 H, J=4.0, 2.5 Hz), 4.98 (s, 2 H), 4.83 (s, 1 H), 4.51 (s, 1 H), 2.42 (s, 3 H), 1.74 (s, 3 H).

Example 67-2

2-Methyl-2-[(4-{(1E)-2-methyl-3-[2-(4-methylbenzoyl)-1H-pyrrol-1-yl]1-yl}benzyl)oxy]propionic acid The title compound was synthesized in a similar manner to Example 1A and 1B ¹H NMR (CDCl₃, 400 MHz) δ 7.72 (d, 2 H, J=8.1 Hz), 7.28 (d, 2 H, J=8.1 Hz), 7.24 (d, 2 H, J=8.1 Hz), 7.19 (d, 2 H, J=8.1 Hz), 7.04 (dd, 1 H, J=2.5, 1.7 Hz), 6.76 (dd, 1 H, J=4.0, 1.7 Hz), 6.22 (dd, 1 H, J=4.0, 2.5 Hz), 6.14 (s, 1 H), 5.15 (s, 2 H), 4.50 (s, 2 H), 2.42 (s, 3 H), 1.56 (s, 6 H).

Example 68

(2R)-3-Hydroxy-2-[(4-{(1E)-3-[2-(4-methylbenzoyl)-1H-pyrrol-1-yl]prop-1-en-1-yl}benzyl)oxy]propionic acid

Example 68-1

Methyl (2R)-2,3-dihydroxypropionate

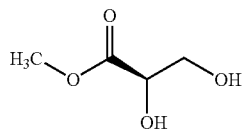

Methyl α,β-isopropyliden-L-glycerate (1 g, 6.24 mmol) was dissolved in acetic acid (14 ml) and water (6 ml), and the mixture was stirred at room temperature for 18 hours. The solvent was evaporated under reduced pressure, and the resulting residue was subjected to azeotropic distillation with toluene three times to give the title compound (610.6 mg, 81%).

$^1$H NMR (CDCl$_3$, 400 MHz) δ 4.29 (dd, 1 H, J=3.8, 3.3 Hz), 3.91 (dd, 1 H, J=11.7, 3.3 Hz), 3.85 (dd, 1 H, J=11.7, 3.8 Hz), 3.84 (s, 3 H).

Example 68-2

Methyl (2R)-3-{[tert-butyl(dimethyl)silyl]oxy}-2-hydroxypropionate

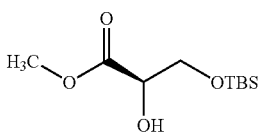

The compound of Example 68-1 (308 mg, 2.57 mmol) was dissolved in methylene chloride (10 ml), and thereto were added triethylamine (704 mg, 6.95 mmol), 4-dimethylaminopyridine (33 mg, 0.27 mmol), and t-butyldimethylsilyl chloride (524 mg, 3.48 mmol). The mixture was stirred at room temperature for 2 hours, and thereto was added a saturated aqueous ammonium chloride solution. The mixture was extracted with ethyl acetate, and the organic layer was washed with water and saturated saline, and dried over anhydrous magnesium sulfate. The solvent was evaporated under reduced pressure, and the resulting residue was purified by silica gel column chromatography to give the title compound (356 mg, 57%).

$^1$H NMR (CDCl$_3$, 400 MHz) δ 4.22 (ddd, 1 H, J=8.1, 3.1, 3.1 Hz), 3.93 (dd, 1 H, J=10.4, 3.1 Hz), 3.86 (dd, 1 H, J=10.4, 3.1 Hz), 3.79 (s, 3 H), 3.02 (d, 1 H, J=8.1 Hz), 0.87 (s, 9 H), 0.06 (s, 3 H), 0.04 (s, 3 H).

Example 68-3

Methyl (2R)-3-{[tert-butyl(dimethyl)silyl]oxy}-2-[(4-iodobenzyl)oxy]propionate

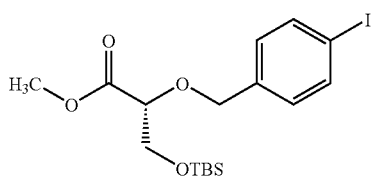

Using the compound of Example 68-2, the title compound was synthesized in a similar manner to Reference Example 42.

LC-MS (method B): r.t. 4.74 min., m/z 451 (M+1)

Example 68-4

Methyl (2R)-3-{[tert-butyl(dimethyl)silyl]oxy}-2-[(4-{(1E)-3-[2-(4-methylbenzoyl)-1H-pyrrol-1-yl]prop-1-en-1-yl}benzyl)oxy]propionate

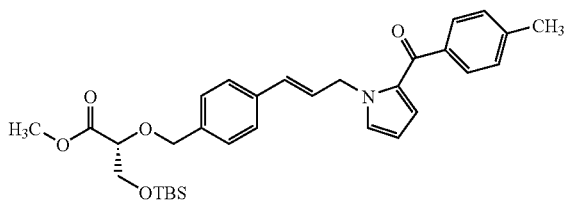

Using the compound of Example 68-3, the title compound was synthesized in a similar manner to Example 1A.

LC-MS (method B): r.t. 4.97 min., m/z 548 (M+1)

Example 68-5

Methyl (2R)-3-hydroxy-2-[(4-{(1E)-3-[2-(4-methylbenzoyl)-1H-pyrrol-1-yl]prop-1-en-1-yl}benzyl)oxy]propionate

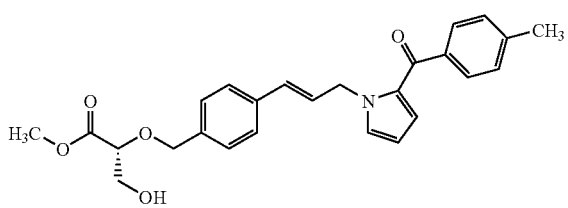

The compound of Example 68-4 (260 mg, 0.48 mmol) was dissolved in THF (5 ml), and thereto was added n-tetrabutylammonium fluoride (1 mol/liter in THF) (1.5 ml, 0.72 mmol) under ice-cooling. Under ice-cooling, the mixture was stirred for one hour, and thereto was added water, and the mixture was extracted with ethyl acetate. The organic layer was washed with water and saturated saline, and dried over anhy-

Example 68-6

(2R)-3-Hydroxy 2-[(4-{(1E)-3-[2-(4-methylbenzoyl)-1H-pyrrol-1-yl]prop-1-en-1-yl}benzyl)oxy] propionic acid

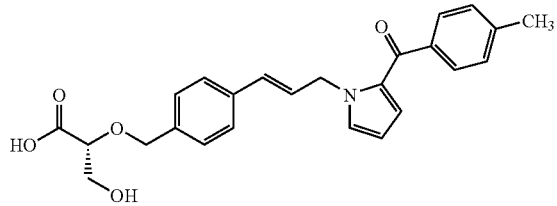

Using the compound of Example 68-5, the title compound was synthesized in a similar manner to Example 1B
LC-MS (method B): r.t. 3.84 min., m/z 420 (M+1)

Example 69

(2R)-2-Hydroxy-3-[(4-{(1E)-3-[2-(4-methylbenzoyl)-1H-pyrrol-1-yl]prop-1-en-1-yl}benzyl)oxy] propionic acid

Example 69-1

Ethyl (2R)-2-hydroxy-3-[(4-{(1E)-3-[2-(4-methylbenzoyl)-1H-pyrrol-1-yl]prop-1-en-1-yl}benzyl)oxy] propionic acid

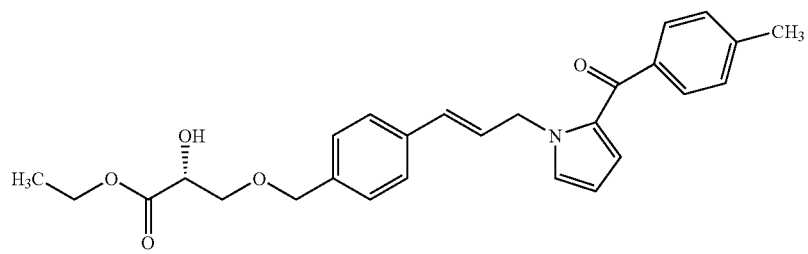

To the compound of Reference Example 33 (36 mg, 0.11 mmol) and (R)-(+)-ethylglycidate (25 mg, 0.22 mmol) was added lithium perchlorate (14 mg, 0.13 mmol), and the mixture was warmed to 60° C., and stirred for 3 hours. The mixture was cooled to room temperature, and water was added thereto. The mixture was extracted with diethyl ether, and the organic layer was washed with water, and dried over anhydrous magnesium sulfate. The solvent was evaporated under reduced pressure to give the title compound.

LC-MS (method B): r.t. 3.97 min., m/z 448 (M+1)

drous magnesium sulfate. The solvent was evaporated under reduced pressure to give the title compound.
LC-MS (method B): r.t. 3.99 min., m/z 434 (M+1)

Example 69-2

(2R)-2-Hydroxy-3-[(4-{(1E)-3-[2-(4-methylbenzoyl)-1H-pyrrol-1-yl]prop-1-en-1-yl}benzyl)oxy] propionic acid

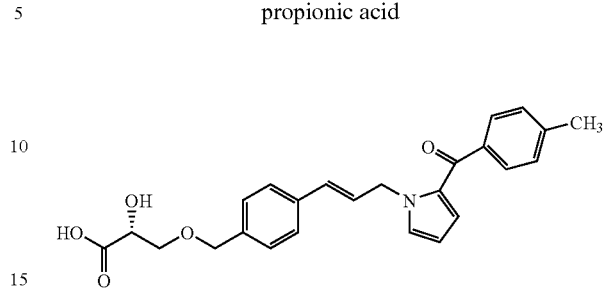

Using the compound of Example 69-1, the title compound was obtained in a similar manner to Example 1B.
LC-MS (method B): r.t. 3.76 min., m/z 420 (M+1)

Example 70

(2R)-2-Methoxy-3 -[(4-{(1E)-3 -[2-(4-methylbenzoyl)-1H-pyrrol-1-yl]prop-1-en-1-yl}benzyl)oxy] propionic acid

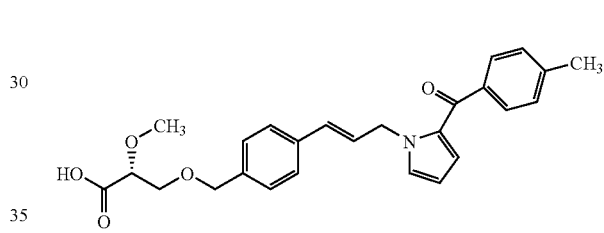

The compound of Example 69-2 (24 mg, 0.05 mmol) was dissolved in THF (1 ml), and thereto was added sodium hydride (5 mg, 0.11 mmol) under ice-cooling. The mixture was warmed to room temperature, and stirred for 30 minutes, and thereto was added methyl iodide (15 mg, 0.11 mmol). The mixture was stirred at room temperature for 2 hours, and thereto was added a 5% aqueous potassium hydrogen sulfate solution, and the mixture was extracted with ethyl acetate. The organic layer was washed with saturated saline, dried over anhydrous magnesium sulfate, and the solvent was evaporated under reduced pressure to give the title compound.

LC-MS (method B): r.t. 3.78 min., m/z 434 (M+1)

Example 71

Evaluation of PPARα or γ agonistic activity

Construction of Reporter Plasmid

By inserting a gene fragment encoding the ligand binding domain of human PPARα (including amino acid residues 167-468) or a gene fragment encoding the ligand binding domain of human PPARγ (including amino acids residue 204-505) into a multicloning site of expressing vector pM containing DNA binding domain of yeast GAL4 protein (Clonetech), a vector plasmid expressing a fused protein of GAL4 protein DNA binding domain and human PPARα or γ ligand binding domain.

As a reporter plasmid, pGL3-Basic Vector containing firefly luciferase gene (Promega Corporation) was used wherein Gal4-responsive sequence UAS and rabbit β-globin promoter were inserted.

For the modification of genetic transformation efficiency, a plasmid containing lacZ gene, pβgal control (Clonetech), was used.

Luciferase Assay

COS-1 cells were cultured in the phenol red free Dulbecco's Modified Eagles Medium (DMEM) (Gibco) supplemented with 5% activated carbon/dextran stripped fetal bovine serum at 37° C. with 5% carbon dioxide. The COS-1 cells were plated at a concentration of $5 \times 10^4$ cells/well into a 24-well plate, and the plate was incubated overnight. The medium was replaced with a fresh medium supplemented without 5% activated carbon/dextran treated fetal bovine serum. Further, the cells were transfected using Lipofectamine plus reagent (Gibco) with plasmid GAL4-PPARα- or γ-expressing plasmid (5 ng), the reporter plasmid (50 ng), pβgal control (350 ng) per well. After incubation for 4 hours, the medium was changed with a fresh medium supplemented with 5% activated carbon/dextran treated fetal bovine serum. Then, the compound of the present invention was added thereto in such an amount that the final concentration thereof is 1 µM or 10 µM. After the cultivation for 24 hours, the cells were lysed with a solution for cell lysis accompanied to the Luciferase Assay System (Promega Corporation). The luciferase activity therein was measured by a luminometer using the reagent for measuring luciferase which was also accompanied to said System. The β-galactosidase activity was measured using a β-galactosidase enzyme assay system (Promega Corporation) to correct the generic transfection efficiency.

The PPARα- or γ-agonistic activity was expressed as a relative activity where the luciferase activity in the well to which the vehicle (DMSO) was added as control was regarded as 1. The PPARα-agonistic activity and the PPARγ-agonistic activity at each 10 pM are shown in the following Table 18.

TABLE 18

| Test Comp. (Example No.) | PPARα-agonistic activity (10 µM) | PPARγ-agonistic activity (10 µM) | Test Comp. (Example No.) | PPARα-agonistic activity (10 µM) | PPARγ-agonistic activity (10 µM) |
|---|---|---|---|---|---|
| 1B | 8.0 | 4.7 | 5B | 11.6 | 5.4 |
| 2B | 7.8 | 5.6 | 6B | 10.1 | 5.5 |
| 3B | 12.6 | 7.5 | 7B | 10.8 | 2.9 |
| 4B | 12.6 | 3.4 | 9B | 8.6 | 5.3 |
| 27 | 16.2 | 9.9 | 29 | 12.5 | 7.3 |
| 38 | 11.6 | 4.7 | 51 | 17.7 | 8.9 |

Example 72

The test compounds as disclosed in Examples were dissolved or suspended in a 0.5% carbomethyl cellulose solution, and orally administered to male db/db mice (7 to 8 weeks old) at a final dose of 30 mg/kg once a day for 2 weeks. On the last day, the blood was taken at the tail vein, and immediately thereafter, perchloric acid was added for removing proteins, and the blood glucose level was measured by Glucolse CII Test Wako (Wako Pure Industries, Ltd.). The results are shown in the following Table 19.

In addition, the hypoglycemic activity was calculated by the following equation.

$$\text{Hypoglycemic Activity}(\%) = \frac{\text{Blood Glucose Level in Vehicle (on Last day)} - \text{Blood Glucose Level in test compound-treated group (on Last day)}}{\text{Blood Glucose Level in Vehicle (on Last day)}} \times 100$$

TABLE 19

| Test Comp. (Example No.) | Hypoglycemic Activity (%) |
|---|---|
| Example 1B | 21.2 |
| Example 3B | 17.8 |
| Example 6B | 63.3 |
| Example 11 | 64.4 |
| Example 27 | 51.0 |
| Example 29 | 43.0 |
| Example 38 | 18.2 |

INDUSTRIAL APPLICABILITY

The novel heteroaryl derivatives (1) of the present invention or a pharmaceutically acceptable salt thereof can be used as an agent for treatment or prophylaxis of diabetic mellitus or as a blood glucose regulator.

The invention claimed is:

1. A heteroaryl derivative of the formula (1):

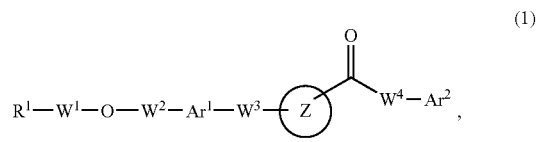

or a pharmaceutically acceptable salt thereof, wherein $R^1$ is a carboxyl group;

$W^1$ and $W^2$ are an optionally substituted lower alkylene;

$Ar^1$ is an optionally substituted phenylene, an optionally substituted pyridine-diyl, or an optionally substituted thiophene-diyl;

$W^3$ is a lower alkenylene;
$W^4$ is a single bond;
$Ar^2$ is an optionally substituted phenyl;
Ring Z is selected from the following formulae (2):

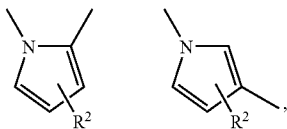

(2)

in which the number of $R^2$ may be one or more, and each is independently selected from a hydrogen atom, a halogen atom, an optionally substituted alkyl, an optionally substituted aryl, an optionally substituted heteroaryl, and an optionally substituted thiol, and either of the binding direction of these groups may be acceptable;

wherein the heteroaryl is a heteromonocyclic aryl or heterobicyclic aryl having 1 to 3 heteroatoms selected from a nitrogen atom, an oxygen atom and a sulfur atom, which is a 5-membered monocyclic heteroaryl, a 6-membered monocyclic heteroaryl or a bicyclic heteroaryl;

the optionally substituted aryl, the optionally substituted heteroaryl, the optionally substituted phenylene, the optionally substituted pyridine-diyl and the optionally substituted thiophene-diyl may have 1 to 5 substituents at any substitution available position, said substituent being a member selected from an optionally substituted lower alkyl, a lower alkenyl, an aryl, a substituted aryl, a heteroaryl, a substituted heteroaryl, an optionally substituted non-aromatic heterocyclic group, a halogen atom, an optionally substituted amino, an optionally substituted acyl, an optionally substituted hydroxy, an optionally substituted thiol, an alkylsulfonyl, cyano, nitro, and a carbamoyl group optionally substituted by an alkyl;

the lower alkyl of the optionally substituted lower alkyl is a straight chain or branched chain $C_1$-$C_8$ alkyl, or a $C_1$-$C_8$ alkyl having a cyclic structure, the substituent of said optionally substituted lower alkyl being a member selected from hydroxy, oxo, amino, a $C_1$-$C_8$ monoalkylamino, a $C_2$-$C_{12}$ dialkylamino, a $C_1$-$C_8$ alkoxy, a halogen atom, a $C_1$-$C_8$ haloalkoxy, a non-aromatic heterocyclic group, an aryl, and a heteroaryl;

the lower alkenyl is a straight chain or branched chain $C_2$-$C_8$ alkenyl or a $C_2$-$C_8$ alkenyl having a cyclic structure;

the aryl is phenyl, 1-naphthyl, or 2-naphthyl;

the non-aromatic heterocyclic group is one having as the ring-forming atoms 2 to 6 carbon atoms and 1 to 3 heteroatoms selected from an oxygen atom, a sulfur atom and a nitrogen atom in addition to the carbon atoms;

the substituent of said substituted aryl, substituted heteroaryl, optionally substituted non-aromatic heterocyclic group is a member selected from a $C_1$-$C_8$ alkyl, a $C_1$-$C_8$ alkoxy, a halogen atom, and a $C_1$-$C_8$ haloalkoxy;

the optionally substituted amino is amino, or an amino optionally substituted by one or two groups selected from a $C_1$-$C_8$ alkyl, a $C_1$-$C_8$ acyl, an aryl, and a heteroaryl;

the acyl is formyl, a group combining a carbonyl group and a $C_1$-$C_8$ alkyl, an aryl, or a heteroaryl, said acyl group having optionally 1 to 3 substituents at any substitution possible position, which are a member selected from a straight chain or branched chain $C_1$-$C_3$ alkyl, a straight chain or branched chain $C_1$-$C_3$ alkoxy, a halogen atom, hydroxy, and amino;

the optionally substituted hydroxy group is a hydroxy, an optionally substituted alkoxy, an optionally substituted aralkyloxy, an optionally substituted aryloxy, or an optionally substituted acyloxy;

the alkoxy of the optionally substituted alkoxy is a $C_1$-$C_8$ alkoxy, and when an alkyl or an alkoxy exists adjacently, then said group may combine together with an adjacent group to form a ring having a substituent;

the aralkyloxy of the optionally substituted aralkyloxy is a phenyl-($C_1$-$C_4$alkyl)oxy;

the aryloxy of the optionally substituted aryloxy is phenyloxy, or 1-naphthyloxy;

the acyloxy of the optionally substituted acyloxy is acetyloxy or propionyloxy;

the substituent of the above-mentioned optionally substituted alkoxy, optionally substituted aralkyloxy, optionally substituted aryloxy, or optionally substituted acyloxy is a member selected from a halogen atom, a straight chain or branched chain $C_1$-$C_3$ alkoxy, a straight chain or branched chain $C_1$-$C_3$ alkyl, trifluoromethyl, and trifluoromethoxy;

the optionally substituted thiol is thiol, an alkylthio, an aralkylthio, an arylthio, or a heteroarylthio, wherein the alkylthio is methylthio, ethylthio, 2-propylthio, or cyclopentylthio, the aralkylthio is a phenyl-($C_1$-$C_8$ alkyl)thio, the arylthio is phenylthio or 1-naphthylthio, and the heteroarylthio is pyridylthio or imidazolylthio;

the alkylsulfonyl is a straight chain or branched chain $C_1$-$C_8$ alkylsulfonyl;

the carbamoyl group optionally substituted by an alkyl is carbamoyl, a straight chain or branched chain $C_1$-$C_6$ monoalkylaminocarbonyl, or a straight chain or branched chain $C_2$-$C_{12}$ dialkylaminocarbonyl;

the lower alkenylene is a $C_2$-$C_8$ alkenylene;

the lower alkylene of the optionally substituted lower alkylene is a straight chain $C_1$-$C_{10}$ alkylene or an alkylene of the following formulae (14):

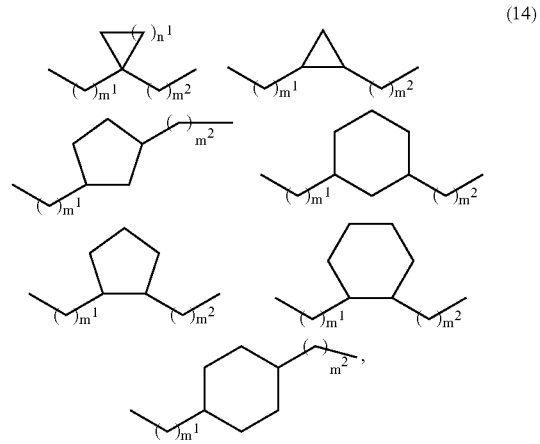

(14)

wherein $m^1$, $m^2$ are integer of 0 to 2, and $n^1$ is an integer of 1 to 4, and the substituent of the optionally substituted lower alkylene is a member selected from an optionally substituted alkyl, an optionally substituted aryl, an optionally substituted heteroaryl, a halogen atom, an optionally substituted amino, an optionally substituted acyl, an optionally substituted thiol, an optionally substituted hydroxy, and an oxo;

the alkyl of the optionally substituted alkyl is a straight chain or branched chain $C_1$-$C_8$ alkyl, or a $C_1$-$C_8$ alkyl having a cyclic structure;

the aryl of the optionally substituted aryl is phenyl, 1-naphthyl or 2-naphthyl; and the substituent of the optionally substituted alkyl, optionally substituted aryl, optionally substituted heteroaryl is a member selected from a halogen atom, a straight chain or branched chain $C_1$-$C_3$ alkoxy, a straight chain or branched chain $C_1$-$C_3$ alkyl, trifluoromethyl, and trifluoromethoxy.

2. The heteroaryl derivative according to claim 1, wherein $W^3$ is a $C_2$-$C_5$ alkenylene, or a pharmaceutically acceptable salt thereof.

3. The heteroaryl derivative according to claim 1 or 2, wherein $W^1$ and $W^2$ are an optionally substituted straight chain $C_1$-$C_3$ alkylene, or an optionally substituted $C_3$-$C_6$ alkylene containing a cyclic structure, or a pharmaceutically acceptable salt thereof.

4. The heteroaryl derivative according to claim 1 or 2, wherein $W^1$ and $W^2$ are an optionally substituted methylene or ethylene, $W^3$ is a $C_3$-$C_4$ alkenylene, or a pharmaceutically acceptable salt thereof.

5. The heteroaryl derivative according to claim 1, wherein $Ar^1$ is an optionally substituted phenylene, and the binding position of $W^2$ is at meta-position or para-position with respect to the binding position of $W^3$, or a pharmaceutically acceptable salt thereof.

6. The heteroaryl derivative according to claim 1, wherein Ring Z is a group of the formula (3):

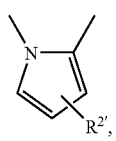

(3)

in which the number of $R^2$, may be one or more, and each is independently selected from a hydrogen atom, methyl, an optionally substituted phenyl, and an optionally substituted heteroaryl, $W^1$ and $W^2$ are an optionally substituted methylene or ethylene, $Ar^1$ is an optionally substituted phenylene, $W^3$ is a $C_3$-$C_4$ alkenylene, or a pharmaceutically acceptable salt thereof.

7. The heteroaryl derivative according to claim 1, wherein Ring Z is a group of the formula (7):

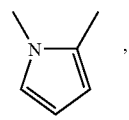

(7)

$W^1$ is an optionally substituted methylene, $W^2$ is methylene, $Ar^1$ is phenylene, $W^3$ is propenylene or propylene, or a pharmaceutically acceptable salt thereof.

8. The heteroaryl derivative according to claim 1, wherein Ring Z is a group of the formula (7):

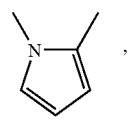

(7)

$W^1$ is a methylene optionally substituted by an alkyl having 1 to 3 carbon atoms, $W^2$ is methylene, $Ar^1$ is phenylene, $W^3$ is propenylene or propylene, $Ar^2$ is a phenyl optionally substituted by an alkyl having 1 to 3 carbon atoms or an alkoxy having 1 to 3 carbon atoms, or a pharmaceutically acceptable salt thereof.

9. The heteroaryl derivative according to claim 1, which is a compound selected from the following formulae (10):

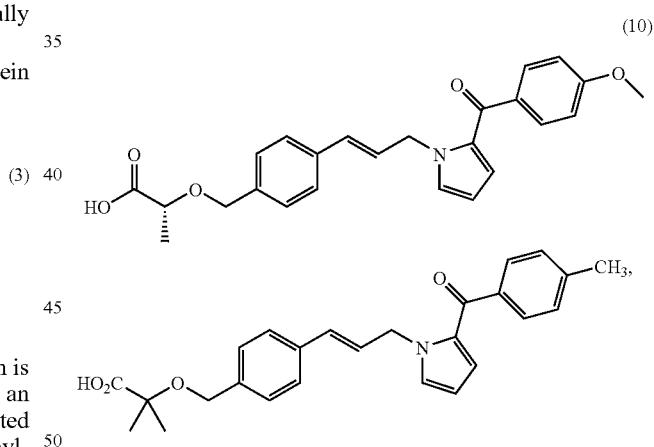

(10)

or a pharmaceutically acceptable salt thereof.

* * * * *